(12) United States Patent
Wei et al.

(10) Patent No.: US 11,851,649 B2
(45) Date of Patent: Dec. 26, 2023

(54) GENERATING MAMMALIAN T CELL ACTIVATION INDUCIBLE SYNTHETIC PROMOTERS (SYN+PRO) TO IMPROVE T CELL THERAPY

(71) Applicant: Seattle Children's Hospital, Seattle, WA (US)

(72) Inventors: Jia Wei, Redmond, WA (US); Michael C. Jensen, Bainbridge Island, WA (US)

(73) Assignee: Seattle Children's Hospital, Seattle, WA (US)

( * ) Notice: Subject to any disclaimer, the term of this patent is extended or adjusted under 35 U.S.C. 154(b) by 1014 days.

(21) Appl. No.: 16/613,025

(22) PCT Filed: May 15, 2018

(86) PCT No.: PCT/US2018/032800
§ 371 (c)(1),
(2) Date: Nov. 12, 2019

(87) PCT Pub. No.: WO2018/213332
PCT Pub. Date: Nov. 22, 2018

(65) Prior Publication Data
US 2020/0095573 A1    Mar. 26, 2020

Related U.S. Application Data

(60) Provisional application No. 62/507,565, filed on May 17, 2017.

(51) Int. Cl.
*A61K 39/00* (2006.01)
*C12N 5/06* (2006.01)
*C12N 15/10* (2006.01)

(52) U.S. Cl.
CPC .................. *C12N 15/1051* (2013.01)

(58) Field of Classification Search
None
See application file for complete search history.

(56) References Cited

U.S. PATENT DOCUMENTS

| | | |
|---|---|---|
| 2003/0108877 A1 | 6/2003 | Blais et al. |
| 2011/0165568 A1* | 7/2011 | Vatta ............... C12Q 1/689 536/23.1 |
| 2014/0349402 A1 | 11/2014 | Cooper et al. |
| 2015/0024482 A1 | 1/2015 | Frigault et al. |
| 2015/0306141 A1 | 10/2015 | Jensen et al. |
| 2017/0073423 A1 | 3/2017 | Juillerat et al. |
| 2017/0073426 A1 | 3/2017 | Ohtomo et al. |

FOREIGN PATENT DOCUMENTS

| WO | WO 16/164731 | 10/2016 |
|---|---|---|
| WO | WO 16/176639 | 11/2016 |

OTHER PUBLICATIONS

Examination Report dated Jul. 11, 2022 for Australian Application No. 2018270156, 3 pgs.
Office Action dated Dec. 19, 2022 for Australian Application No. 2018270156, 2 pages.
Office Action dated Nov. 14, 2022 for Chinese Application No. 20188004 7704.0, 15 pages.
Extended European Search Report dated Jan. 26, 2021 for European Application No. 18803169.4, 7 pages.
Examination Report dated Mar. 23, 2022 European Application No. 18803169.4, 7 pgs.
Notice of Reasons of Refusal dated Apr. 5, 2022 for Japanese Application No. 2019-563586, 19 pages.
Baumann et al., Mar. 2003, An unexpected role for FosB in activation-induced cell death of T cells, Oncogene, 22(9):1333-1339.
Best et al., Apr. 2013, Transcriptional insights into the CD8+ T cell response to infection and memory T cell formation, Nat Immunol., 14(4):404-412.
Brown et al., Feb. 2014, Synthetic promoters for CHO cell engineering, Biotechnology and Bioengineering.
Fiering et al., Oct. 1990, Single cell assay of a transcription factor reveals a threshold in transcription activated by signals emanating from the T-cell antigen receptor, Genes Dev, 4(10):1823-1834.
Shaw et al., Jul. 8, 1988, Identification of a putative regulator of early T cell activation genes, Science, 241(4862):202-205.
Crist, et al., "Structure/Function analysis of the Murine CD95L Promoter Reveals the Identification of a Novel Transcriptional Repressor and Functional CD28 Response Element" Journal of Biological Chemistry, Jul. 2003, pp. 35950-35958, vol. 278.
Frigault, Matthew J. et al., "Identification of chimeric antigen receptors that mediate constitutive or inducible proliferation of T cells" Cancer Immunology Research, Apr. 2015, pp. 356-367, vol. 3, No. 4.
Roybal, Kole T. et al., "Engineering T Cells with Customized Therapeutic Response Programs Using Synthetic Notch Receptors" Cell, Oct. 2016, pp. 419-432. vol. 167.
International Search Report for PCT/US2018/032800 dated Aug. 8, 2018.
Office Action dated May 19, 2023 for Chinese Application No. 201880047704.0, a foreign counterpart of U.S. Appl. No. 16/613,025, 4 pages.

* cited by examiner

*Primary Examiner* — Maria G Leavitt
(74) *Attorney, Agent, or Firm* — C. Rachal Winger; Lee & Hayes, PC

(57) ABSTRACT

Aspects of the invention described herein relate to methods of making and using inducible promoters for transgene expression. The inducible promoters are derived from the NFAT-RE inducible system and are used to improve or enhance T cell survival and proliferation.

20 Claims, 37 Drawing Sheets

Specification includes a Sequence Listing.

DNA Seq Result Summary

| Sample | Total # Pairs | Total # Paired Reads | % Paired Reads | Total # Unique Conting | Total # Most Abundant Contig | % Most Abundant Contig | Most Abundant Promoter Sequence |
|---|---|---|---|---|---|---|---|
| S1 | 1826076 | 1023557 | 61.66 | 115035 | 40806 | 3.99 | 2f7r8f11r5r1f5r7f3f8f7r8f |
| S2 | 1506812 | 817484 | 59.68 | 88825 | 60320 | 7.38 | 6f3f7r8r7f5r8r8f8f3r2f1r4f |
| S3 | 1522386 | 884653 | 63.92 | 91955 | 34295 | 3.88 | 5r7r8f1f8f10r3r5f5f6r8r8f5r |
| S4 | 1507421 | 892453 | 65.12 | 110787 | 31072 | 3.48 | 8f8r11r1f6f3r7f8f8f1r6f8f11r5f7f |
| S5 | 2185959 | 1058756 | 53.28 | 63144 | 159200 | 15.04 | 2r11r4f1117r3r2r7r11f2r9f8r8r |
| S6 | 2441189 | 1258036 | 56.69 | 88523 | 116010 | 9.22 | 6r11r9f6r6f7r8f3f9f6r1f6f |
| S7 | 2075802 | 1142991 | 60.57 | 88841 | 184563 | 16.15 | 5r7r8f1f8f10r3r5f5f6r8r8f5r |

GENERATING MAMMALIAN T CELL ACTIVATION INDUCIBLE SYNTHETIC PROMOTERS (SYN+PRO) TO IMPROVE T CELL THERAPY

CROSS REFERENCE TO RELATED APPLICATIONS

This application is a U.S. National Phase Application of PCT International Application Number PCT/US2018/032800, filed on May 15, 2018, designating the United States of America and published in the English language, which is an International Application of and claims the benefit of priority to U.S. Provisional Application No. 62/507,565, filed on May 17, 2017. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-152NP.txt, created Nov. 6, 2019, which is 19 kb in size. The information in the electronic format of the Sequence Listing is incorporated herein by reference in its entirety

FIELD OF THE INVENTION

Described herein are methods of making and using inducible promoters for transgene expression. The inducible promoters are derived from an NFAT-RE inducible system and are used to improve or enhance T cell survival and proliferation.

BACKGROUND OF THE INVENTION

Many different inducible promoters have been used in T cell therapy. There remains a continued need for promoters that exhibit a strong signal and, in particular, the need for promoters that exhibit a high signal to noise ratio and, which can be repetitively turned on, is manifest.

SUMMARY

In a first aspect, a method of making an inducible synthetic promoter library is provided, wherein the method comprises screening promoters, wherein the promoters are screened for being activated following CAR T cell activation, thereby producing a set of screened promoters, screening transcription factor response elements, thereby producing a set of screened transcription factor response elements, making an inducible synthetic promoter library comprising promoters that are activated following CAR T cell activation of transcription factor response elements and synthesizing oligonucleotides, wherein the oligonucleotides comprise a first sequence encoding a screened transcription factor response element and a second sequence encoding a screened promoter.

In a second aspect, an inducible synthetic promoter is provided. The inducible synthetic promoter comprises a first sequence encoding a transcription factor response element and a second sequence encoding a promoter sequence, optionally, wherein said inducible synthetic promoter comprises one or more of SEQ ID. NOs: 1-33. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-$CD^3$/anti-CD28 antibodies. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-33. In some alternatives, the transcription factor response element is E2F1, EGR1, HIF1A, NFAT, LEF1, SP1, PU.1, NFKB, JUN, FOS, and/or STAT4.

In a third aspect, a cell for molecule expression is provided, wherein the cell comprises a vector, wherein the vector comprises the inducible synthetic promoter any of the alternatives described above, a gene encoding a molecule and a sequence encoding a chimeric antigen receptor. The inducible synthetic promoter can comprise a first sequence encoding a transcription factor response element and a second sequence encoding a promoter sequence, optionally, wherein said inducible synthetic promoter comprises one or more of SEQ ID. NOs: 1-33. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-$CD^3$/anti-CD28 antibodies. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-33. In some alternatives, the transcription factor response element is E2F1, EGR1, HIF1A, NFAT, LEF1, SP1, PU.1, NFKB, JUN, FOS, and/or STAT4. In some alternatives, the molecule is a protein, an antibody or binding fragment thereof, pro-proliferation molecule or a molecule that can eradicate tumors. In some alternatives, the cell is a hematopoietic stem cell. In some alternatives, the chimeric antigen receptor is specific for CD19. In some alternatives, the cell is CD8+ or CD4+. In some alternatives, expression of the molecule is inducible. In some alternatives, the CAR comprises a signaling domain. In some alternatives, the signaling domain is 1G, 2G or 3G. In some alternatives, the vector is a lentiviral vector, a transposase based minicircle or a nanoplasmid. In some alternatives, the cell further comprises a TCR knock out system for CAR specific activation. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

In a fourth aspect, a method of regulating gene expression in CAR T cell therapy is provided, the method comprises providing the cell of any one of the alternatives herein and introducing the cell into a subject in need of a CAR T cell therapy. The cell comprises a vector, wherein the vector comprises the inducible synthetic promoter any of the alternatives described herein, a gene encoding a molecule and a sequence encoding a chimeric antigen receptor. The inducible synthetic promoter can comprise a first sequence encoding a transcription factor response element and a second sequence encoding a promoter sequence, optionally, wherein said inducible synthetic promoter comprises one or more of SEQ ID. NOs: 1-33. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-CD³/anti-CD28 antibodies. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-33. In some alternatives, the transcription factor response element is E2F1, EGR1, HIF1A, NFAT, LEF1, SP1, PU.1, NFKB, JUN, FOS, and/or STAT4. In some alternatives, the molecule is a protein, an antibody or binding fragment thereof, pro-proliferation molecule or molecule that can eradicate tumors. In some alternatives, the cell is a hematopoietic stem cell. In some alternatives, the chimeric antigen receptor is specific for CD19. In some alternatives, the cell is CD8+ or CD4+. In some alternatives, expression of the molecule is inducible. In some alternatives, the CAR comprises a signaling domain. In some alternatives, the signaling domain is 1G, 2G or 3G. In some alternatives, the vector is a lentiviral vector, a transposase based minicircle or a nanoplasmid. In some alternatives, the cell further comprises a TCR knock out system for CAR specific activation. In some alternatives, the molecule is Chimeric Cytokine Receptors such as CCR (CD122, CD127, and CD360), CASTAT5, and PD1 chimeras such as PD1:CD28, dnSHP1/2, IL-12 and/or a miRNA such as miRNA155. In some alternatives, the method of regulating gene expression in CAR T cell therapy further comprises monitoring the subject for a response to the molecule expressed under control of the inducible synthetic promoter. In some alternatives, of the method of regulating gene expression in CAR T cell therapy, the subject is further monitored for expression of the molecule expressed under control of the inducible synthetic promoter. In some alternatives, of the method of regulating gene expression in CAR T cell therapy, the molecule is a protein, an antibody or binding fragment thereof, a cytokine, and/or an anti-cancer therapeutic. In some alternatives, of the method of regulating gene expression in CAR T cell therapy, the method further comprises inducing expression of the molecule. In some alternatives, the inducing is performed by administering PMA or Ionomycin. In some alternatives, the inducing step is performed prior to administering the cells to the subject in need, and wherein the cells are exposed to anti-CD³/anti-CD28 beads prior to administering of the cells. In some alternatives, the subject is suffering from or has been diagnosed as having a cancer. In some alternatives, the molecule is Chimeric Cytokine Receptors such as CCR (CD122, CD127, and CD360), CASTAT5, and PD1 chimeras such as PD1:CD28, dnSHP1/2, IL-12 and/or a miRNA such as miRNA155. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

In a fifth aspect, a method of ameliorating, inhibiting, or treating a disease, such as a cancer (e.g., any one or more of leukemia, breast cancer, stomach cancer, esophageal cancer, brain cancer, uterine cancer, prostate cancer, bone cancer, liver cancer, pancreatic cancer, ovarian cancer, lung cancer, colon cancer, kidney cancer, bladder cancer, uterine cancer or thyroid cancer), in a subject in need is provided, wherein the method comprises providing a vector to a cell, wherein the cell comprises the inducible synthetic promoter of any one of the alternatives described herein and wherein the cell comprises a chimeric antigen receptor, administering the cell to the subject in need and inducing expression of a molecule. The vector comprises the inducible synthetic promoter any of the alternatives described herein, a gene encoding a molecule and a sequence encoding a chimeric antigen receptor. The inducible synthetic promoter can comprise a first sequence encoding a transcription factor response element and a second sequence encoding a promoter sequence, optionally, wherein said inducible synthetic promoter comprises one or more of SEQ ID. NOs: 1-33. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-CD³/anti-CD28 antibodies. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-33. In some alternatives, the transcription factor response element is E2F1, EGR1, HIF1A, NFAT, LEF1, SP1, PU.1, NFKB, JUN, FOS, and/or STAT4. In some alternatives, the molecule is a protein, an antibody or binding fragment thereof, pro-proliferation molecule or molecule that can eradicate tumors. In some alternatives, the cell is a hematopoietic stem cell. In some alternatives, the chimeric antigen receptor is specific for CD19. In some alternatives, the cell is CD8+ or CD4+. In some alternatives, expression of the molecule is inducible. In some alternatives, the CAR comprises a signaling domain. In some alternatives, the signaling domain is 1G, 2G or 3G. In some alternatives, the vector is a lentiviral vector, a transposase based minicircle or a nanoplasmid. In some alternatives, the cell further comprises a TCR knock out system for CAR specific activation. In some alternatives, the molecule is CCR (CD122), CASTAT5, and PD1:CD28 and/or a miRNA. In some alternatives, the cell is from the subject. In some alternatives of the method of ameliorating, inhibiting, or treating a disease in a subject in need, the method further comprises monitoring the subject for a response to the molecule expressed under control of the inducible synthetic promoter. In some alternatives, the molecule is a protein, an antibody, a cytokine or an anti-cancer therapeutic. In some alternatives, the method further comprises inducing expression of the molecule. In some alternatives, the inducing is performed by administering PMA or Ionomycin. In some alternatives, the inducing step is performed prior to administering the cells to the subject in need, wherein the cells are exposed to anti-CD³/anti-CD28 antibodies conjugated onto beads prior to administering of the cells. In some alternatives, the subject is suffering from cancer. In some alternatives, the molecule is CCR (CD122), CASTAT5, PD1:CD28 and/or a miRNA. In some alternatives, the subject is selected for a therapy for cancer. In some alternatives, the cancer is leukemia, breast cancer, stomach cancer, esophageal cancer, brain cancer, uterine cancer, prostate cancer, bone cancer, liver cancer, pancreatic cancer, ovarian cancer, lung cancer, colon cancer, kidney cancer, bladder cancer, uterine cancer or thyroid cancer. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

DETAILED DESCRIPTION

Figure 1:
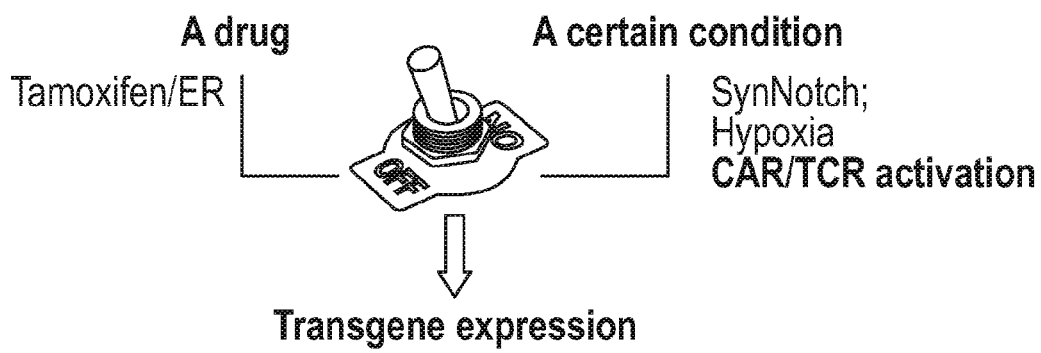
FIG. 1 shows a schematic of regulated gene expression in CAR T cell therapy.
Figure 2:
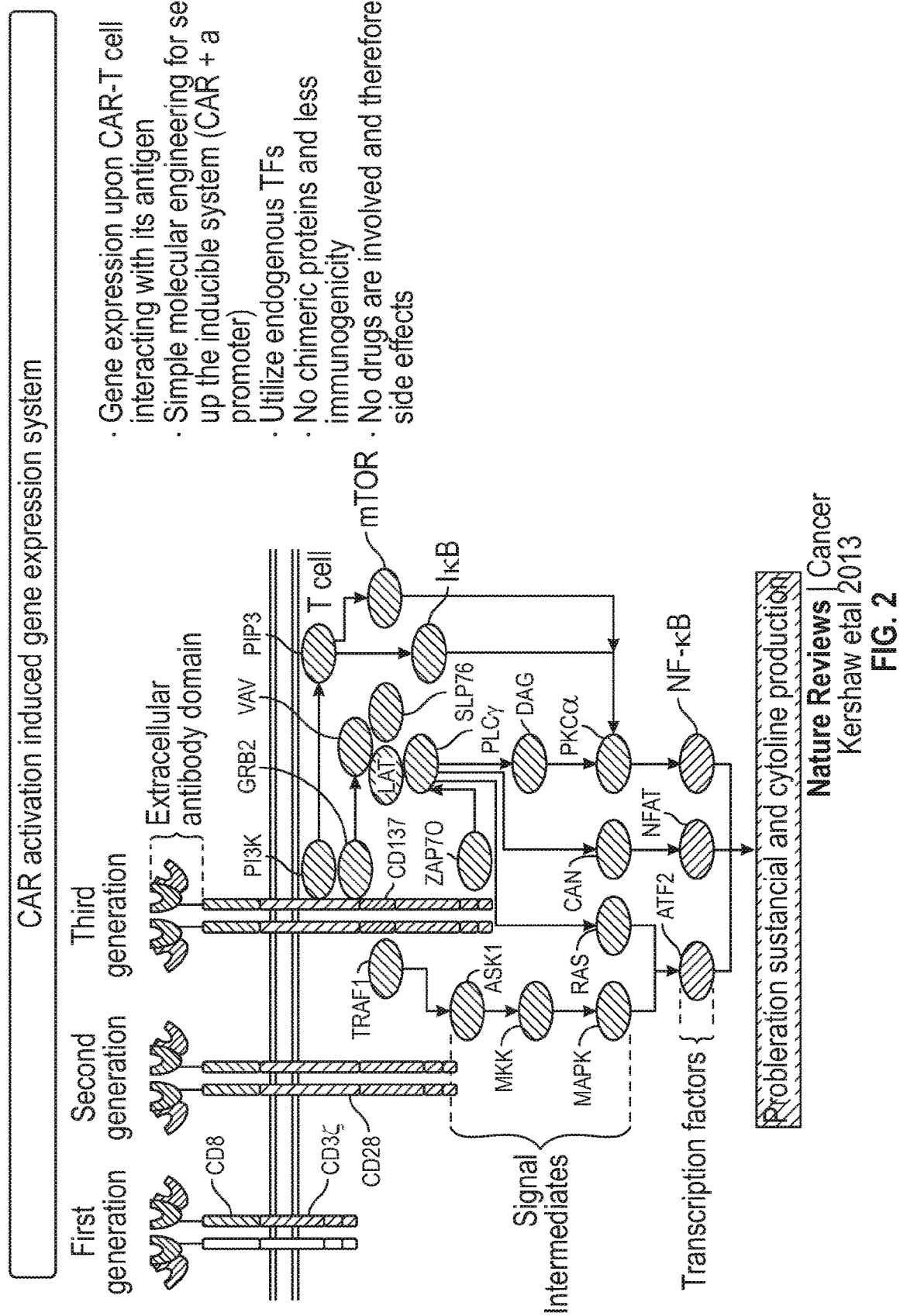
FIG. 2 shows a schematic of CAR activation induced gene expression system.

"Conditional" or "Inducible" as used herein have their plain and ordinary meaning when read in light of the specification, and may include but is not limited to, for example, a nucleic acid construct that includes a promoter that provides for gene expression in the presence of an inducer and does not substantially provide for gene expression in the absence of the inducer. Without being limiting, examples of inducible promoters for mammalian expression constructs include tetracycline, ecdysone, streptogramins, macrolides or doxycycline inducible promoters. Without being limiting, examples of inducible promoters for bacterial expression constructs include but are not limited to a T7 promoter, lac promoter, trc promoter, tac promoter, tetA promoter, araBAD promoter or a rhaPBAD promoters. Without being limiting, insect-derived promoters include but are not limited to pB2 and polyhedrin promoters. In some alternatives herein, a promoter is provided, wherein the promoter is an inducible promoter for mammalian protein expression. In some alternatives, the promoter is an inducible synthetic promoter. In some alternatives, the promoter is selected to be activated following CAR T cell activation.

A "promoter" has its plain and ordinary meaning when read in light of the specification, and may include but is not limited to, for example, nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. It is a region of DNA that initiates transcription of a particular gene. Promoters are located near the transcription start sites of genes, on the same strand and upstream on the DNA (towards the 5' region of the sense strand). Promoters can be about 100, 200, 300, 400, 500, 600, 700, 800, or 1000 base pairs long or within a range defined by any two of the aforementioned lengths. As used herein, a promoter can be constitutively active, repressible or inducible. If a promoter is an inducible promoter, then the rate of transcription increases in response to an inducing agent. In some alternatives, the promoter is a synthetic promoter.

As used herein, "nucleic acid" or "nucleic acid molecule" have their plain and ordinary meaning when read in light of the specification, and may include but is not limited to, for example, polynucleotides or oligonucleotides such as deoxyribonucleic acid (DNA) or ribonucleic acid (RNA), oligonucleotides, fragments generated by the polymerase chain reaction (PCR), and fragments generated by any of ligation, scission, endonuclease action, exonuclease action, and by synthetic generation. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded. They can also be referred to as "oligonucleotides."

"Transcription factor response elements," have their plain and ordinary meaning when read in light of the specification, and may include but is not limited to, for example, short sequences of DNA within a gene promoter region that are able to bind specific transcription factors and regulate transcription of genes. Under conditions of stress, a transcription activator protein binds to the response element and stimulates transcription. They may also be a short (50-1500 bp) region of DNA that can be bound by proteins (activators) to increase or promote or enhance the likelihood that transcription of a particular gene will occur or the level of transcription that takes place. These activator proteins are usually referred to as transcription factors. Enhancers are generally cis-acting, located up to 1 Mbp (1,000,000 bp) away from the gene and can be upstream or downstream from the start site, and either in the forward or backward direction. An enhancer may be located upstream or downstream of the gene it regulates. A plurality of enhancer domains may be used in some embodiments to generate greater transcription e.g., multimerized activation binding domains can be used to further enhance or increase the level of transcription. Furthermore, an enhancer doesn't need to be located near the transcription initiation site to affect transcription, as some have been found located in several hundred thousand base pairs upstream or downstream of the start site. Enhancers do not act on the promoter region itself, but are bound by activator proteins. These activator proteins interact with the mediator complex, which recruits polymerase II and the general transcription factors, which then begin transcribing the genes. Enhancers may also be found within introns. An enhancer's orientation may even be reversed without affecting its function. Additionally, an enhancer may be excised and inserted elsewhere in the chromosome, and still affect gene transcription. An example of an enhancer binding domain is the TCR alpha enhancer. In some alternatives, the enhancer domain in the alternatives described herein is a TCR alpha enhancer.

"Transcriptional activator domains" or "Transcriptional activation domain" have their plain and ordinary meaning when read in light of the specification, and may include but is not limited to, for example, specific DNA sequences that can be bound by a transcription factor, in which the transcription factor can thereby control the rate of transcription of genetic information from DNA to messenger RNA. Specific transcription factors can include but is not limited to SP1, AP1, C/EBP, heat shock factor, ATF/CREB, c-Myc, Oct-1 and/or NF-1.

A "chimeric antigen receptor" (CAR) described herein, also known as chimeric T-cell receptor, has its plain and ordinary meaning when read in light of the specification, and may include but is not limited to, for example, an artificial T-cell receptor or a genetically engineered receptor, which grafts a desired specificity onto an immune effector cell. A CAR may be a synthetically designed receptor comprising a ligand binding domain of an antibody or other protein sequence that binds to a molecule associated with the disease or disorder and is linked via a spacer domain to one or more intracellular signaling domains of a T-cell or other receptors, such as a costimulatory domain. In some alternatives, a cell, such as a mammalian cell, is manufactured wherein the cell comprises a chimeric antigen receptor. These receptors can be used to graft the specificity of a monoclonal antibody or a binding portion thereof onto a T-cell, for example. In some alternatives herein, the genetically engineered cell further comprises a sequence that encodes a chimeric antigen receptor. In some alternatives, the chimeric antigen receptor is specific for a molecule on a tumor cell. A chimeric antigen receptor or an engineered cell expressing a T cell receptor can be used to target a specific tissue.

"Ligand" as described herein, refers to a substance that can form a complex with a biomolecule. By way of example and not of limitation, ligands can include substrates, proteins, small molecules, inhibitors, activators, nucleic acids and neurotransmitters. Binding can occur through intermolecular forces, for example ionic bonds, hydrogen bonds, and van der walls interactions. Ligand binding to a receptor protein can alter the three dimensional structure and determine its functional state. The strength of binding of a ligand is referred to as the binding affinity and can be determined by direct interactions and solvent effects. A ligand can be bound by a "ligand binding domain." A ligand binding domain, for example, can refer to a conserved sequence in a structure that can bind a specific ligand or a specific epitope on a protein. The ligand binding domain or ligand binding portion can comprise an antibody or binding fragment thereof or scFv, a receptor ligand or mutants thereof, peptide, and/or polypeptide affinity molecule or binding partner. Without being limiting, a ligand binding domain can be a specific protein domain or an epitope on a protein that is specific for a ligand or ligands.

"PMA" or "phorbol 12-myristate 13-acetate" is a diester of phorbol and a potent tumor promoter often employed in biomedical research to activate the signal transduction enzyme protein kinase C (PKC). In the alternatives, herein, PMA is used to induce a inducible synthetic promoter.

"Ionomycin" is an ionophore produced by the bacterium *Streptomyces conglobatus*. It is used in research to raise the intracellular level of calcium (Ca2+) and as a research tool to understand Ca2+ transport across biological membranes. It is also used to stimulate the intracellular production of the following cytokines; interferon, perforin, IL-2, and/or IL-4—usually in conjunction with PMA. In the alternatives herein, the Ionomycin is used to induce an inducible synthetic promoter.

A "minimal promoter" is used to get a low amount of transcription of a target gene. They have key sequences to specify the transcription start site, but only weakly activates transcription because it does not recruit RNA Polymerase or transcription factors strongly. In the alternatives herein, the minimal promoter sequence is an IL2-minimal promoter sequence which is a fragment of IL2 promoter (−70 to +47) containing a TATA box. Prior to construction and use of an IL-2minimal promoter, a commercial minimal promoter from an inducible gene expression construct was tested. The commercially available minimal promoter was shown to work in cell lines but not in primary T cells.

A "protein" is a macromolecule comprising one or more polypeptide chains. A protein can also comprise non-peptide components, such as carbohydrate groups. Carbohydrates and other non-peptide substituents can be added to a protein by the cell in which the protein is produced, and will vary with the type of cell. Proteins are defined herein in terms of their amino acid backbone structures; substituents such as carbohydrate groups are generally not specified, but can be present nonetheless. In some alternatives, a cell is provided wherein the cell comprises a vector, wherein the vector comprises a gene encoding a protein, an antibody or binding fragment thereof, pro-proliferation molecule or molecule that can eradicate tumors.

An "antibody" as described herein refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain about 70-110 amino acids and are classified into different categories according to their size and function.

"Pro-proliferation molecule," as described herein, refer to chimeric cytokine receptors such as CCR(CD122), CCR (CD127), CCR(CD360), caSTAT5, miRNA such as miRNA155, dnSHP1, dnSHP2, PD1 chimeras such as PD1: MyD88 and PD1:CD28, CD200:CD28. In some alternatives herein, the inducible synthetic promoter drives the synthesis of a pro-proliferation molecule.

"Inducible synthetic promoter library, as used herein has its plain and ordinary meaning when read in light of the specification, and may include but is not limited to, for example, CAR activation inducible promoter library, T cell exhaustion inducible promoter library, tumor micro-environment inducible promoter library, hypoxia inducible promoter library.

"Inducible synthetic promoter" (iSynPro) as used herein has its plain and ordinary meaning when read in light of the specification, and may include but is not limited to, for example, a CAR activation inducible promoter library, T cell exhaustion inducible promoter library, tumor micro-environment inducible promoter library, hypoxia inducible promoter library.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development, they become double-positive thymocytes (CD4$^+$CD8$^+$), and finally mature to single positive (CD4$^+$ CD8$^-$ or CD4$^-$CD8$^+$) thymocytes that are then released from the thymus to peripheral tissues.

CD19 as used herein has its plain and ordinary meaning when read in light of the specification, and may include but is not limited to, for example, a protein that is found on the surface of white blood cells and can assemble with the antigen receptor of B lymphocytes in order to decrease the threshold for antigen receptor-dependent stimulation. CD19 is expressed on follicular dendritic cells and B cells. CD19 is present on B cells from earliest recognizable B-lineage cells during development to B-cell blasts but is lost on maturation to plasma cells. CD19 primarily acts as a B cell co-receptor in conjunction with CD21 and CD81. Upon activation, the cytoplasmic tail of CD19 becomes phosphorylated, which leads to binding by Src-family kinases and recruitment of P1-3 kinase. As on T-cells, several surface molecules form the antigen receptor and form a complex on B lymphocytes.

Mutations in CD19 are associated with severe immunodeficiency syndromes characterized by diminished antibody production. For example, aberrant expression of CD19 is a marker of monocytic lineage in acute myelogenous leukemia. Since CD19 is a hallmark of B-cells, the protein can be used to diagnose cancers that arise from this type of cell, notably B-cell lymphomas. Since 2011, therapies targeting CD19 have begun to enter clinical trials. Most current experimental anti-CD19 drugs in development work by exploiting the presence of CD19 to direct the therapy specifically towards B-cell cancers. However, it is now emerging that the protein plays an active role in driving the growth of these cancers, by stabilizing the concentrations of the MYC oncoprotein. Thus, CD19 and its downstream signaling can be attractive therapeutic targets.

"Subject" or "patient," as described herein, refers to any organism upon which the alternatives described herein may be used or administered, e.g., for experimental, diagnostic, prophylactic, and/or therapeutic purposes. Subjects or patients include, for example, animals. In some alternatives, the subject is mice, rats, rabbits, non-human primates, and/or humans. In some alternatives, the subject is a cow, sheep, pig, horse, dog, cat, primate or a human.

"Cytokines" as described herein, refers to small proteins (5-25 kDa) that are important in cell signaling. Cytokines are released by cells and affect the behavior of other cells, and sometimes the releasing cell itself, such as a T-cell. Cytokines can include, for example, chemokines, interferons, interleukins, lymphokines, and/or tumor necrosis factor. Cytokines can be produced by a broad range of cells, which can include, for example, immune cells like macrophages, B lymphocytes, T lymphocytes and/or mast cells, as well as, endothelial cells, fibroblasts, and/or various stromal cells.

Cytokines can act through receptors, and are important in the immune system as the cytokines can modulate the balance between humoral and cell-based immune responses, and they can regulate the maturation, growth, and responsiveness of particular cell populations. Some cytokines enhance or inhibit the action of other cytokines in complex ways. Without being limiting, cytokines can include, for example, Acylation stimulating protein, Adipokine, Albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, Chemokine, Colony-stimulating factor, CX3CL1, CX3 CR1, CXCL1, CXCL10, CXCL11, CXCL13, CXCL14, CXCL15, CXCL16, CXCL17, CXCL2, CXCL3, CXCL5, CXCL6, CXCL7, CXCL9, Erythropoietin, Gc-MAF, Granulocyte colony-stimulating factor, Granulocyte macrophage colony-stimulating factor, Hepatocyte growth factor, IL 10 family of cytokines, IL 17 family of cytokines, IL1A, IL1B, Inflammasome, Interferome, Interferon, Interferon beta 1a, Interferon beta 1b, Interferon gamma, Interferon type I, Interferon type II, Interferon type III, Interleukin, Interleukin 1 family, Interleukin 1 receptor antagonist, Interleukin 10, Interleukin 12, Interleukin 12 subunit beta, Interleukin 13, Interleukin 15, Interleukin 16, Interleukin 2, Interleukin 23, Interleukin 23 subunit alpha, Interleukin 34, Interleukin 35, Interleukin 6, Interleukin 7, Interleukin 8, Interleukin 36, Leukemia inhibitory factor, Leukocyte-promoting factor, Lymphokine, Lymphotoxin, Lymphotoxin alpha, Lymphotoxin beta, Macrophage colony-stimulating factor, Macrophage inflammatory protein, Macrophage-activating factor, Monokine, Myokine, Myonectin, Nicotinamide phosphoribosyltransferase, Oncostatin M, Oprelvekin, Platelet factor 4, Proinflammatory cytokine, Promegapoietin, RANKL, Stromal cell-derived factor 1, Talimogene laherparepvec, Tumor necrosis factor alpha, Tumor necrosis factors, XCL1, XCL2, GM-CSF, and/or XCR1.

"Interleukins" or IL as described herein, are cytokines that the immune system depends largely upon. Examples of interleukins, which can be utilized herein, for example, include IL-1, IL-2, IL-3, IL-4, IL-5, IL-6, 11-7, IL-8/CXCL8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. Contacting T-cells with interleukins can have effects that promote, support, induce, or improve engraftment fitness of the cells. IL-1, for example can function in the maturation & proliferation of T-cells. IL-2, for example, can stimulate growth and differentiation of T-cell response. IL-3, for example, can promote differentiation and proliferation of myeloid progenitor cells. IL-4, for example, can promote proliferation and differentiation. IL-7, for example, can promote differentiation and/or proliferation of lymphoid progenitor cells, involved in B, T, and NK cell survival, development, and/or homeostasis. IL-15, for example, can induce production of natural killer cells. IL-21, for example, co-stimulates activation and/or proliferation of CD8+ T-cells, augments NK cytotoxicity, augments CD40-driven B cell proliferation, differentiation and/or isotype switching, and/or promotes differentiation of Th17 cells.

"Vector," "Expression vector" or "construct" is a nucleic acid used to introduce heterologous nucleic acids into a cell that has regulatory elements to provide expression of the heterologous nucleic acids in the cell. Vectors include but are not limited to plasmid, minicircles, yeast, and/or viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. In some alternatives, wherein the vector is a lentiviral vector, a transposase based minicircle or a nanoplasmid.

"Combination therapy" as described herein, refers to a therapy that uses more than one medication or modality for a therapeutic application. Combination therapy, for example can also refer to multiple therapies to treat a single disease, and often all the therapies are pharmaceutical product combinations. Combination therapy can also involve prescribing and administering separate drugs in which the dosage can also have more than one active ingredient. In some alternative, a combination therapy is provided. In some alternatives, the combination therapy can further comprise administering a CAR bearing T-cell to a subject in need e.g., a human.

"Chemotherapeutic drugs" are category of anti-cancer medicaments that can use, for example, chemical substances, such as anti-cancer drugs (chemotherapeutic agents) that can be given as part of a standardized chemotherapy regimen. Chemotherapeutic drugs can be given with a curative intent, or it can aim to prolong life or to reduce symptoms (palliative chemotherapy). Additional chemotherapies can also include hormonal therapy and targeted therapy, as it is one of the major categories of medical oncology (pharmacotherapy for cancer). These modalities are often used in conjunction with other cancer therapies, such as radiation therapy, surgery, and/or hyperthermia therapy. In few cases, cancer has been known to spread due to surgery. In some alternatives, a genetically modified immune cell is administered to the tumor site prior to or after a surgical procedure.

Some newer anticancer drugs (for example, various monoclonal antibodies, humanized versions thereof and/or binding fragments thereof) are not indiscriminately cytotoxic, but rather target proteins that are abnormally expressed in cancer cells and that are essential for their growth. Such therapies are often referred to as targeted therapy (as distinct from classic chemotherapy) and are often used alongside traditional chemotherapeutic agents in antineoplastic protocols. In some alternatives, the methods described herein can further comprise administering any one or more of these targeted anti-cancer therapies (for example, various monoclonal antibodies, humanized versions thereof and/or binding fragments thereof).

Chemotherapy, in which chemotherapeutic drugs are administered, can use one drug at a time (single-agent chemotherapy) or several drugs at once (combination chemotherapy or polychemotherapy). The combination of chemotherapy and radiotherapy is chemoradiotherapy. Chemotherapy using drugs that convert to cytotoxic activity only upon light exposure is called photochemotherapy or photodynamic therapy. In some alternatives of administering the cell described herein, the method can further comprise administering to a subject having cancer, photochemotherapy or photodynamic therapy after receiving the cells.

Chemotherapeutic drugs can include but are not limited to antibody-drug conjugates (for example, an antibody or binding fragment thereof attached to a drug by a linker), nanoparticles (for example a nanoparticle can be 1-1000 nanometer sized particle for promoting tumor selectivity and aid in delivering low-solubility drugs), electochemotherapy, alkylating agents, antimetabolites (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and/or Thioguanine), anti-tumor antibiotics, topoisomerase inhibitors, mitotic inhibitors, corticosteroids, DNA intercalating agents, or checkpoint inhibitors (for example checkpoint kinases CHK1, or CHK2). In some alternatives of the methods described herein, the genetically modified immune cells or compositions comprising genetically modified immune cells are administered in combination with one or more anti-cancer agents, such as any one or more of the foregoing compounds or therapies. In some alternatives, the one or more anti-cancer agents that are co-administered or administered in conjunction with the genetically modified immune cells, comprises antibody-drug conjugates, nanoparticles, electrochemotherapy, alkylating agents, antimetabolites, anti-tumor antibiotics, topoisomerase inhibitors, mitotic inhibitors, corticosteroids, DNA intercalating agents, or checkpoint inhibitors. In some alternatives, the antimetabolites comprises 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine.

"Cancer" as described herein, can refer to a malignant tumor or a malignant neoplasma in which they involve abnormal cell growth with the potential to invade or spread to other parts of a body. In some alternatives, a method of treating, ameliorating, or inhibiting a disease or an infection in a subject is provided, wherein the method comprises delivering a cell of manufactured by any of the alternatives described herein to the subject. In some alternatives, the subject suffers from a cancer. In some alternatives, the subject is selected for a cancer therapy. In some alternatives the cancer comprises adrenal cancer, bile duct cancer, bladder cancer, bone cancer, brain cancer, breast cancer, Castleman disease, cervical cancer, colon cancer, endometrial cancer, esophagus cancer, Ewing family of tumors, eye cancer, gallbladder cancer, gastrointestinal carcinoid tumors, Hodgkin disease, Kaposi Sarcoma, kidney cancer, Laryngeal and hypopharyngeal cancer, leukemia, liver cancer, lung cancer, lymphoma, multiple myeloma, malignant mesothelioma, myelodysplastic syndrome, nasopharyngeal cancer, osteosarcoma, ovarian cancer, pancreatic cancer, pituitary tumors, prostate cancer, retinoblastoma, skin cancer, small intestine cancer, stomach cancer, testicular cancer, thymus cancer, thyroid cancer or uterine sarcoma.

Figure 3:
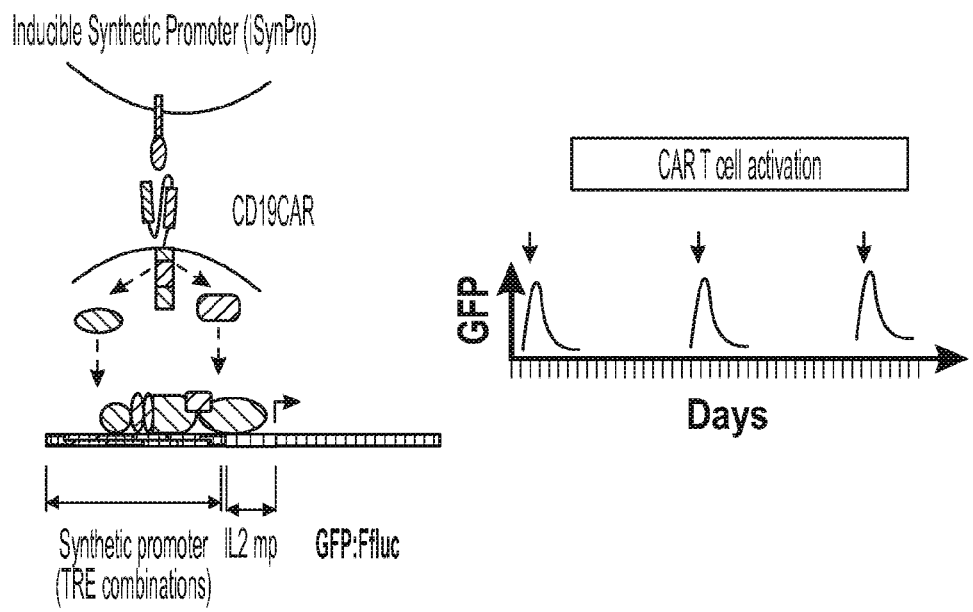
FIG. 3 shows the diagram exemplifying the function of the inducible synthetic promoter (iSynPro) and a graph that indicates CAR T cell activation by the iSynPro. Upon the scFv engagement with the antigen, the intracellular domain of the CAR induces various transcription factors to bind to different promoter regions to activate corresponding gene expression. While the endogenous gene expression orchestra is going, a synthetic promoter which is composed of optimum TRE elements can start downstream transcription by utilizing the activated transcription factors. This transcription activation by a synthetic promoter can be induced multiple times upon CAR T cell activation. The traditional way of engineering promoters require efforts in a rational design. The number of TREs tested was limited and the successful rate was low. As shown in the figure, a synthetic promoter library was generated with millions of unique species and allowed the CAR T cells screen out the strongest inducible promoters.
Figure 27:
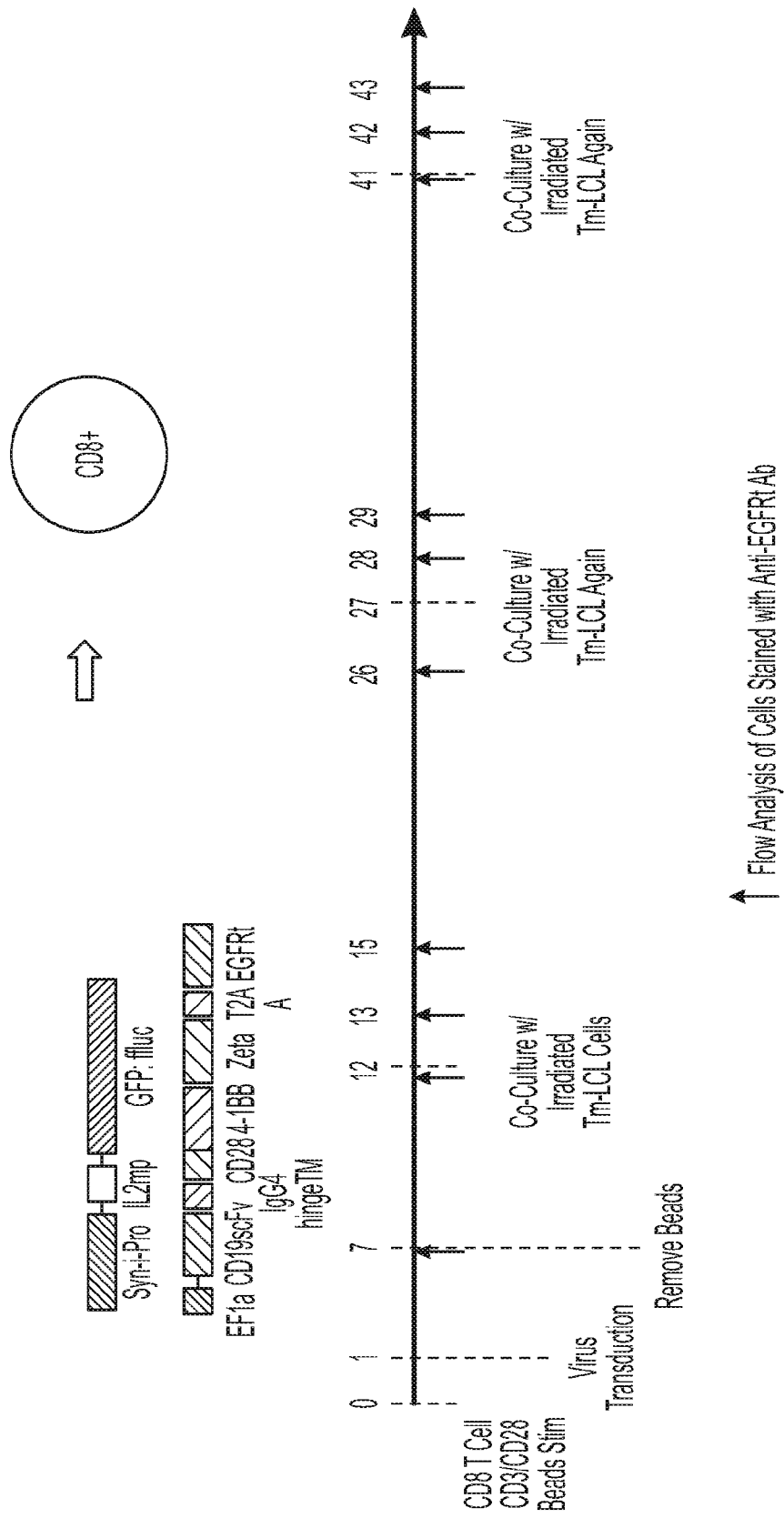
FIG. 27 is an example timeline for the Syn-iPro testing in CD8+ CAR T cells. As shown, CD8 T cells are first stimulated with CD3/CD28 beads. After 24 hours, the cells are transduced with a viral vector. At day 7, beads are removed. The cells are then co-cultured at day 11 with irradiated Tm-LCL cells. This is repeated at day 27 and 41.

A synthetic promoter library was generated by random ligation of transcription factor response elements (TREs), built upstream of a known IL2 minimal promoter (IL2mp) and screened by a reporter gene expression in chimeric antigen receptor (CAR) engineered T cells upon CAR activation. Methods for developing the library for the assays are exemplified by FIG. 5, which shows how to screen promoters that are activated upon CAR T cell activation. The actions of the inducible synthetic promoter (iSynPro) is shown in FIG. 3. DNA was extracted from the sorted cells and sequenced. The top candidates of the derived promoter sequences were then synthesized and verified in the same system. The identified or selected promoters (also referred to as Syn-i-Pro throughout this disclosure) were found to be CAR activation inducible, CD3/CD28 inducible or chemical inducible (e.g. PMA/Ionomycin). For example, the promoter can be inducible by a bead comprising CD3, or CD28 or both (FIG. 27). The Syn-i-Pro controlled gene expression was not significantly weakened even after multiple rounds of stimulation (at least four). These promoters are useful in CAR T cell therapy, such as when the expression of a desired molecule in CAR T cells is selectively needed so as to avoid a side effect seen when constitutive expression is used, for example.

Figure 4:
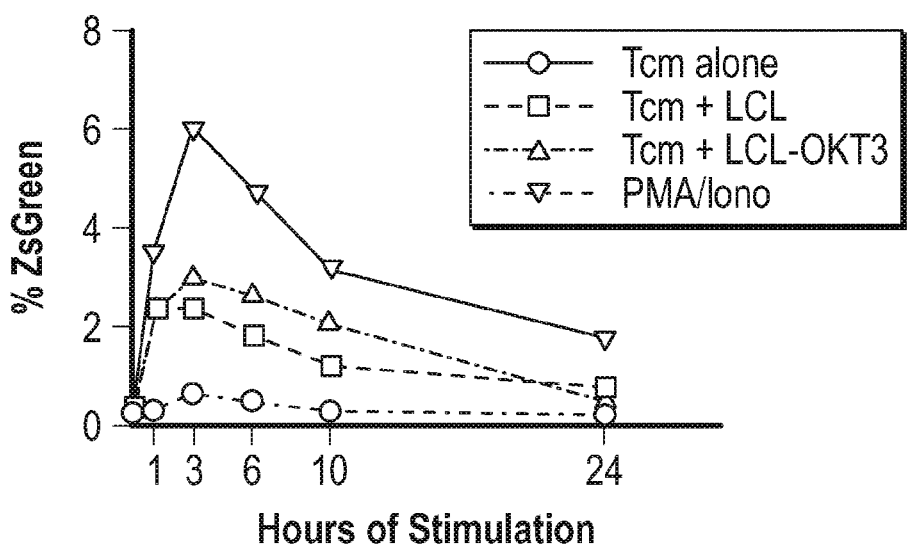
FIG. 4 is a graph that demonstrates the functionality of the NFAT promoter in CD8+ cells. As shown, the NFAT regulated promoter leads to poor induction in CD8+ cells.

Although NFAT inducible promoters have been used in T cell therapy, the inducible promoters generated by the methods described herein (Syn-i-Pro promoters) showed a stronger reporter signal than the endogenous or unmodified NFAT promoter. In some embodiments, the NFAT inducible promoters developed by the approaches described herein demonstrated a much higher signal to noise ratio than the endogenous or unmodified NFAT promoter and some of the promoters generated using the methods described herein can be repetitively turned on. As shown in FIG. 4, the NFAT promoter has poor induction in CD8 cells. The Syn-i-Pros promoters developed using the methodologies described herein can be used in CAR T cells to not only control the expression of a molecule that may have a side effect when constitutively expressed but these promoters can restrict or not express a molecule before the CAR T cell interacts with a desired antigen.

In some embodiments, the Syn-i-Pros promoters developed using the approaches described herein may exhibit a relatively higher basal level expression. Syn-i-Pros promoters that exhibit a lower level of basal level expression can be generated by engineering a minimal promoter sequence or by changing the expression system from a lentivirus to a transposase based minicircle or nanoplasmid. One benefit of the CAR activation of gene expression of the Syn-i-Pro promoters described herein is that with CAR activation, there are no drugs involved and therefore no side effects. The methodologies used and additional embodiments are described in Additional Alternatives described below.

ADDITIONAL ALTERNATIVES

In some alternatives, a method of making an inducible synthetic promoter library is provided, the method comprising: screening promoters, wherein the promoters are screened for being activated following CAR T cell activation, thereby producing screened promoters; screening transcription factor response elements, thereby producing screened transcription factor response elements; making an inducible synthetic promoter library comprising promoters that are activated following CAR T cell activation of transcription factor response elements; and synthesizing oligonucleotides, wherein the oligonucleotides comprise a first sequence encoding a screened transcription factor response element and a second sequence encoding a screened promoter.

In some alternatives, a inducible synthetic promoter is provided, wherein the inducible synthetic promoter comprises a first sequence encoding a transcription factor response element; and a second sequence encoding a promoter sequence, optionally, wherein said inducible synthetic promoter comprises one or more of SEQ ID. NOs: 1-39. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with CD3/CD28. In some alternatives, the CD3/CD28 are conjugated on beads. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-39. In some alternatives, the inducible synthetic promoter comprises a sequence that has a 80%, 85%, 90% or 90% sequence identity or has a sequence identity within a range between any two aforementioned percentages to a sequence set forth in any one of SEQ ID NO's 1-39. In some alternatives, the transcription factor response element is E2F1, EGR1, HIF1A, NFAT, LEF1, SP1, PU.1, NFKB, JUN, FOS, and/or STAT4.

In some alternatives, a cell for molecule expression is provided, the cell comprising: a vector, wherein the vector comprises the inducible synthetic promoter of any one of the alternatives herein, a gene encoding a molecule; and a sequence encoding a chimeric antigen receptor. The inducible synthetic promoter comprises a first sequence encoding a transcription factor response element; and a second sequence encoding a promoter sequence, optionally, wherein said inducible synthetic promoter comprises one or more of SEQ ID. NOs: 1-39. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-CD$^3$/anti-CD28. In some alternatives, the anti-CD$^3$/anti-CD28 are conjugated on beads. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-39. In some alternatives, the inducible synthetic promoter comprises a sequence that has a 80%, 85%, 90% or 90% sequence identity or has a sequence identity within a range between any two aforementioned percentages to a sequence set forth in any one of SEQ ID NO's 1-39. In some alternatives, the transcription factor response element is E2F1, EGR1, HIF1A, NFAT, LEF1, SP1, PU.1, NFKB, JUN, FOS, and/or STAT4. In some alternatives, the molecule is a protein, an antibody or binding fragment thereof, pro-proliferation molecule or molecule that can eradicate tumors. In some alternatives, the cell is a hematopoietic stem cell. In some alternatives, the chimeric antigen receptor is specific for CD19. In some alternatives, the cell is CD8+ or CD4+. In some alternatives, expression of the molecule is inducible. In some alternatives, the CAR comprises a signaling domain. In some alternatives, the CAR comprises a spacer. A spacer can comprise any 20 amino acids, for example, in any order to create a desirable length of polypeptide chain in a chimeric antigen receptor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine and/or tryptophan. A spacer sequence can be a linker between the scFv and the transmembrane domain of the chimeric antigen receptor. In some alternatives, the signaling domain is 1G, 2G or 3G. In some alternatives, the vector is a lentiviral vector, a transposase based minicircle or a nanoplasmid. In some alternatives, the cell further comprises a TCR knock out system for CAR specific activation. In some alternatives, the molecule is CCR (CD122), CASTAT5, PD1:CD28 and/or a miRNA. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

In some alternatives, a method of regulating gene expression in CAR T cell therapy, the method comprising: providing the cell of any one of the alternatives herein; and introducing the cell into a subject in need of a CAR T cell therapy. The cell comprises a vector, wherein the vector comprises the inducible synthetic promoter of any one of the alternatives herein, a gene encoding a molecule; and a sequence encoding a chimeric antigen receptor. The inducible synthetic promoter comprises a first sequence encoding a transcription factor response element; and a second sequence encoding a promoter sequence, optionally, wherein said inducible synthetic promoter comprises one or more of SEQ ID. NOs: 1-39. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-CD$^3$/anti-CD28. In some alternatives, the anti-CD$^3$/anti-CD28 are conjugated on beads. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-39. In some alternatives, the inducible synthetic promoter comprises a sequence that has a 80%, 85%, 90% or 90% sequence identity or has a sequence identity within a range between any two aforementioned percentages to a sequence set forth in any one of SEQ ID NO's 1-39. In some alternatives, the transcription factor response element is E2F1, EGR1, HIF1A, NFAT, LEF1, SP1, PU.1, NFKB, JUN, FOS, and/or STAT4. In some alternatives, the molecule is a protein, an antibody or binding fragment thereof, pro-proliferation molecule or molecule that can eradicate tumors. In some alternatives, the cell is a hematopoietic stem cell. In some alternatives, the chimeric antigen receptor is specific for CD19. In some alternatives, the cell is CD8+ or CD4+. In some alternatives, expression of the molecule is inducible. In some alternatives, the CAR comprises a signaling domain. In some alternatives, the CAR comprises a spacer. A spacer can comprise any 20 amino acids, for example, in any order to create a desirable length of polypeptide chain in a chimeric antigen receptor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine and/or tryptophan. A spacer sequence can be a linker between the scFv and the transmembrane domain of the chimeric antigen receptor. In some alternatives, the signaling domain is 1G, 2G or 3G. In some alternatives, the vector is a lentiviral vector, a transposase based minicircle or a nanoplasmid. In some alternatives, the cell further comprises a TCR knock out system for CAR specific activation. In some alternatives, the molecule is CCR (CD122), CASTAT5, PD1:CD28 and/or a miRNA. In some alternatives, the method further comprises monitoring the subject for a response to the molecule expressed under control of the inducible synthetic promoter. In some alternatives, the subject is further monitored for expression of the molecule expressed under control of the inducible synthetic promoter. In some alternatives, the molecule is a protein, an antibody or binding fragment thereof, a cytokine, or an anti-cancer therapeutic. In some alternatives, the method further comprises inducing expression of the molecule. In some alternatives, the inducing is performed by administering PMA or Ionomycin. In some alternatives, the inducing step is performed prior to administering the cells to the subject in need, and wherein the cells are exposed to anti-CD3/anti-CD28 beads prior to administering of the cells. In some alternatives, the subject is suffering from or has been diagnosed as having a cancer. In some alternatives, the molecule is CCR(CD122), CASTAT5, PD1:CD28 and/or miRNA. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

In some alternatives, a method of ameliorating, inhibiting, or treating a disease (e.g., any one or more of leukemia, breast cancer, stomach cancer, esophageal cancer, brain cancer, uterine cancer, prostate cancer, bone cancer, liver cancer, pancreatic cancer, ovarian cancer, lung cancer, colon cancer, kidney cancer, bladder cancer, uterine cancer or thyroid cancer) in a subject in need is provided, the method comprising: providing a vector to a cell, wherein the cell comprises the inducible synthetic promoter of any one of the alternatives herein and wherein the cell comprises a chimeric antigen receptor; administering the cell to the subject in need; and inducing expression of a molecule. The inducible synthetic promoter comprises a first sequence encoding a transcription factor response element; and a second sequence encoding a promoter sequence, optionally, wherein said inducible synthetic promoter comprises one or more of SEQ ID. NOs: 1-39. In some alternatives, the inducible synthetic promoter is inducible by chimeric antigen receptor activation. In some alternatives, the inducible synthetic promoter is inducible by binding of the chimeric antigen receptor to a ligand. In some alternatives, the inducible synthetic promoter is inducible by interaction with anti-CD3/anti-CD28. In some alternatives, the anti-CD3/anti-CD28 are conjugated on beads. In some alternatives, the inducible synthetic promoter is inducible by a chemical. In some alternatives, the chemical is PMA or Ionomycin. In some alternatives, the promoter comprises an endogenous IL2 minimal promoter sequence. In some alternatives, the inducible synthetic promoter comprises a sequence set forth in any one of SEQ ID NO's 1-39. In some alternatives, the inducible synthetic promoter comprises a sequence that has a 80%, 85%, 90% or 90% sequence identity or has a sequence identity within a range between any two aforementioned percentages to a sequence set forth in any one of SEQ ID NO's 1-39. In some alternatives, the transcription factor response element is E2F1, EGR1, HIF1A, NFAT, LEF1, SP1, PU.1, NFKB, JUN, FOS, and/or STAT4. In some alternatives, the cell is from the subject. In some alternatives, the method further comprises monitoring the subject for a response to the molecule expressed under control of the inducible synthetic promoter. In some alternatives, the molecule is a protein, an antibody or binding fragment thereof, a cytokine or an anti-cancer therapeutic. In some alternatives, the method further comprises inducing expression of the molecule. In some alternatives, the inducing is performed by administering PMA or Ionomycin. In some alternatives, the inducing step is performed prior to administering the cells to the subject in need, wherein the cells are exposed to anti-CD3/anti-CD28 beads prior to administering of the cells. In some alternatives, the subject is suffering from cancer. In some alternatives, the molecule is Chimeric Cytokine Receptors such as CCR (CD122, CD127, and CD360), CASTAT5, PD1 chimeras such as PD1:CD28, dnSHP1/2, IL-12 and/or a miRNA such as miRNA155. In some alternatives, the subject is selected for a therapy for cancer. In some alternatives, the cancer is leukemia, breast cancer, stomach cancer, esophageal cancer, brain cancer, uterine cancer, prostate cancer, bone cancer, liver cancer, pancreatic cancer, ovarian cancer, lung cancer, colon cancer, kidney cancer, bladder cancer, uterine cancer or thyroid cancer. In some alternatives, the subject is selected for combination therapy. In some alternatives, the molecule is a Chimeric Cytokine Receptor. In some alternatives, the Chimeric Cytokine Receptor comprises CCR, CASTAT5, PD1 chimeras and/or a miRNA. In some alternatives, the miRNA comprises miRNA155. In some alternatives, the CCR comprises CD122, CD127 or CD360. In some alternatives, the PD1 chimera comprises PD1:CD28, dnSHP1/2 and/or IL-12.

Alternative 1

The NFAT Promoter Leads to Poor Induction in CD8 Cells

Synthetic promoters were contemplated in order to obtain promoters that would be useful in regulated gene expression in CAR T cell therapy. As shown in FIG. 1, a drug may be used to turn on and off transgene expression such as expression of a CAR or a TCR in a T cell or to turn on the activation.

Figure 5:
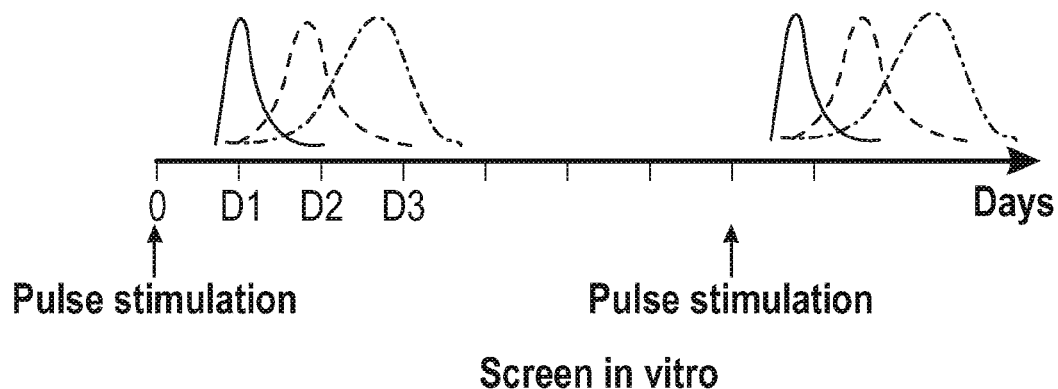
FIG. 5 shows a schematic of how a synthetic promoter library was designed in order to screen out promoters that are activated upon CAR T cell activation.

Also contemplated is a method of designing a synthetic promoter library that is screened in order to isolate promoters that are activated upon CAR T cell activation. (FIG. 5). Genes upregulated by T cell activation may be identified by mRNA analysis as well as the transcription factors that are upregulated, which may be identified as transcription response elements (TRE) (FIG. 6).

A relative complete gene expression profile of TCR activated CD8 T cell has been previously reported by Blair et al (Best, Blair et al. 2013; included by reference in its entirety). Through a TRED and TRANSFAC database search, eleven transcription factors that have been confirmed to regulate these genes were chosen. The selected genes were E2F1, EGR1, FOS, HIF1a, JUN, NFAT, LEF1, NFkB, SP1, PU.1, and STAT4. Their corresponding TRE sequences were obtained from JASPAR database and synthesized.

Figure 7:
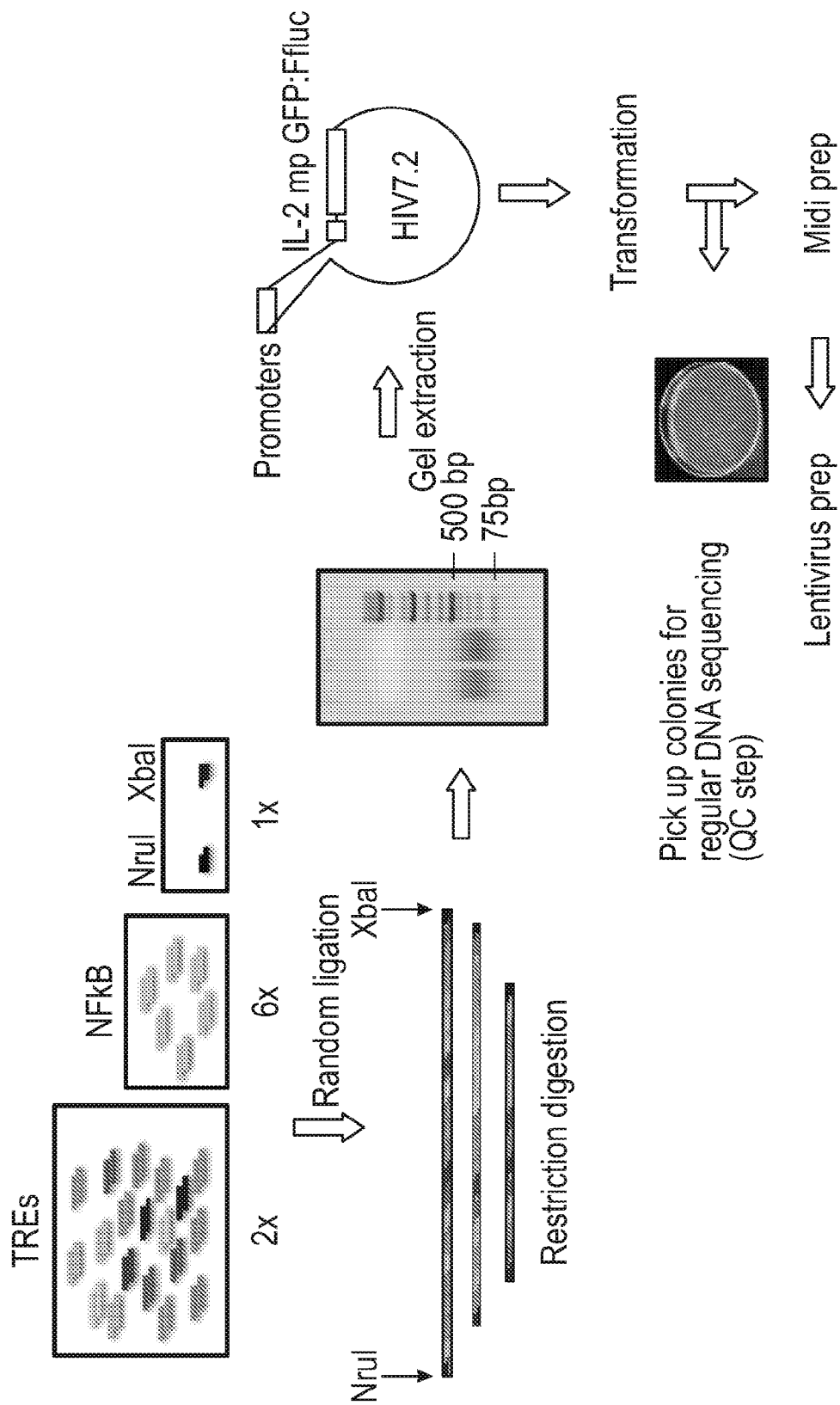
FIG. 7 is a schematic that shows the steps and methods for the construction of the inducible iSynPro library.
Figures 1, 8:
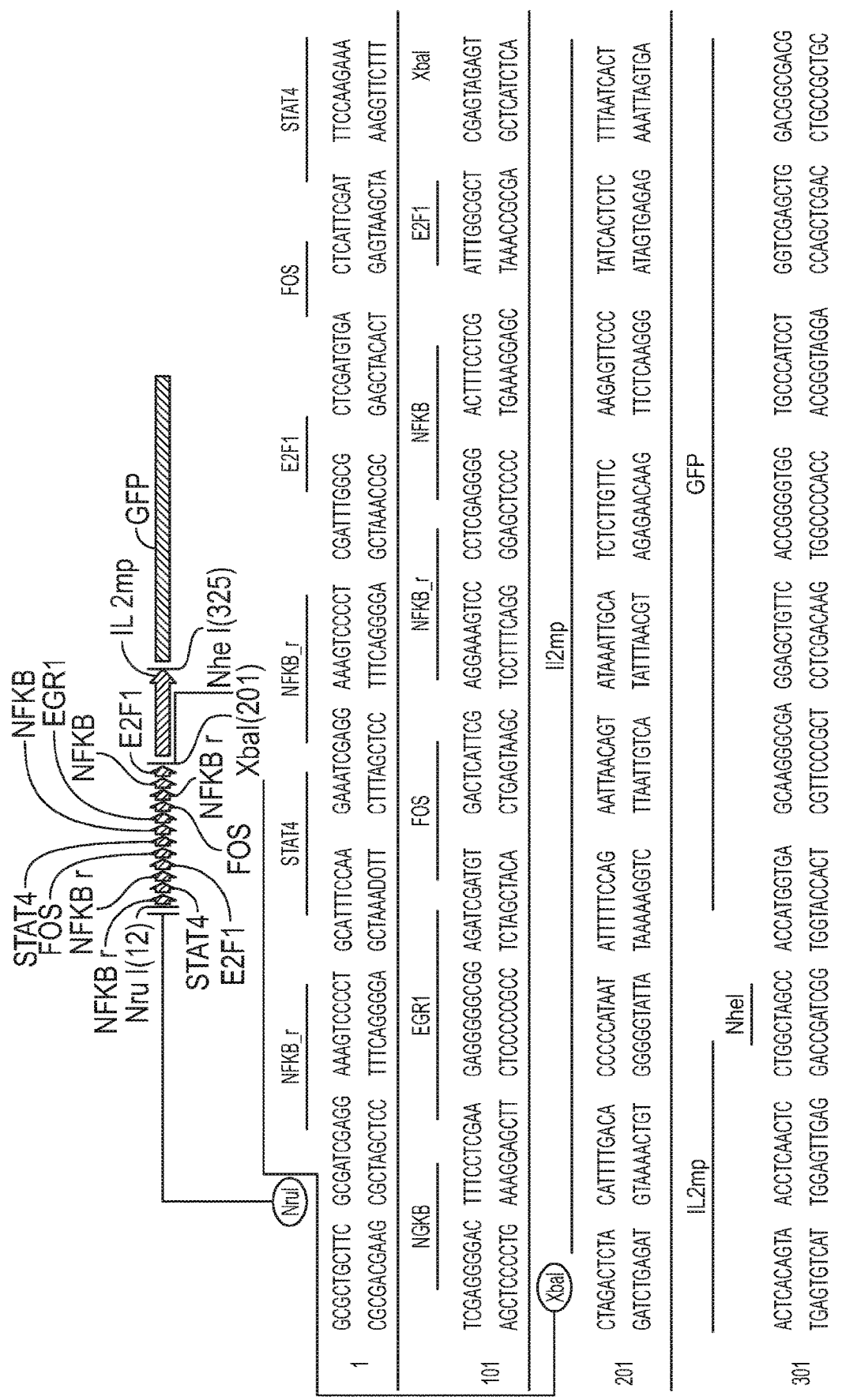
FIG. 8 shows a schematic of the Sanger sequencing of colonies from the iSynPRo plasmid library. A diagram is shown demonstrating mapping of a sequencing result. As shown, transcription factor response elements (TRE) are mapped from a sequence. A summary of the sequencing result for selected clones as shown in two bar graphs. Shown in the left panel is a measurement of the frequency of TREs in 10 clones. On the right panel is a measurement of the number of TRE per clone.
Figures 2, 8:
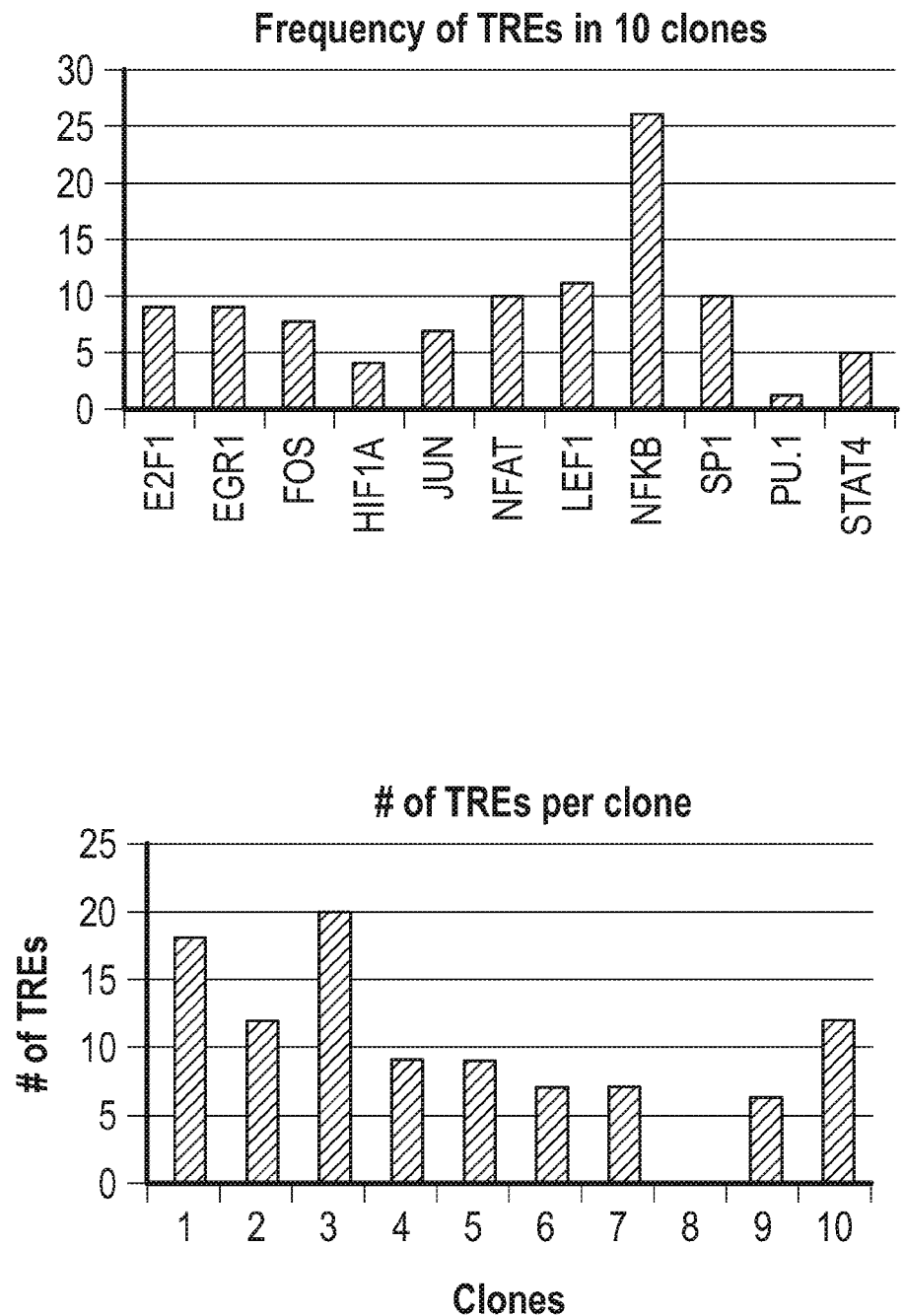

The genes for the TRE may be used for ligating into a vector with a promoter to drive expression of a CAR or TCR (FIG. 7). As shown in FIG. 8, the frequency of the TRE may lead to expression of several TRE dependent on the types of promoters that they are driven by.

Figure 6:
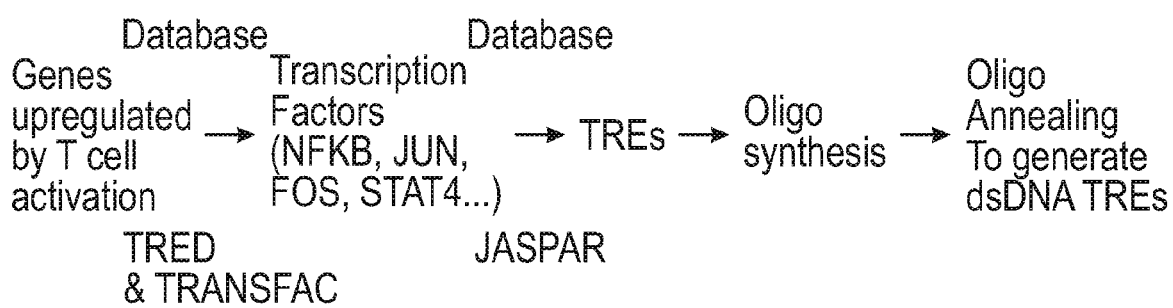
FIG. 6 shows a schematic for how the building blocks for the synthetic promoter library were generated using different databases. As shown in the Ven diagram, the library of proteins may include E2F1, EGR1, FOS, 1IF1A, JUN, JFAT, LEF1, NFKB, SP1, PU.1, and/or STAT4.
Figure 6:
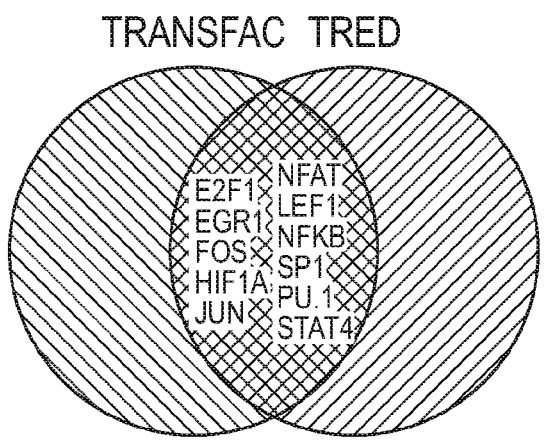

As shown in FIG. 6, a relative complete gene expression profile of TCR activated CD8 T cell has been previously reported (Best, Blair et al. 2013). Genes were selected that were significantly upregulated upon CD8 T cell activation. Through a TRED and TRANSFAC database search, eleven transcription factors that have been confirmed to regulate these genes were chosen. The selected genes were E2F1, EGR1, FOS, HIF1a, JUN, NFAT, LEF1, NFkB, SP1, PU.1, and STAT4. Their corresponding TRE sequences were obtained from JASPAR database and synthesized.

The sense and antisense TRE oligonucleotides were annealed and the double stranded TREs were used as "building blocks" to generate a synthetic promoter library through random ligation as previously described (Brown A. 2014; included by reference in its entirety herein) (FIG. 7) CARs in the clinical trials were mainly 2nd generation 4-1BB-CD3 zeta CAR. Based on its intracellular signaling domain relatively more NFkB building blocks were recruited since it had been known NFkB was a downstream transcription factor of 4-1BB. Two cloning blocks, each containing a restriction enzyme cutting site, were also included to allow cloning into a plasmid vector and to control the size range of the ligation products. Thus the random ligation reaction pool contained 2× of each TRE block (no NFkB TRE), 6× of NFkB block and 1× of cloning blocks. The dsDNA ligation library was digested by restriction enzymes and, as expected, it was a diversified library showing on an agarose gel as a smear ranging from ~75 bp to ~500 bp.

To be able to screen the library in primary T cells, the digested ligation library was inserted into a HIV7 transfer plasmid containing a GFP and a fire fly luciferase fusion reporter gene (GFP:ffluc) and an IL2 minimal promoter. The GFP:ffluc reporter gene had been used in the lab for both in vitro and in vivo assays previously. The IL2mp had been published by multiple labs (Durand, Shaw et al. 1988, Fiering, Northrop et al. 1990; included by reference in their entireties herein) and were also tested in the lab previously. A No promoter and an IL2 mp only construct were created as negative control constructs; and a 6×NFAT-IL2mp and a 7×NFkB-IL2mp were used as positive control constructs for the following screening. Before continuing with virus packaging and screening, the library was analyzed to see if the library looked the same as was expected. A small portion of transformed E. coli cells were streaked on an agarose plate and 10 colonies were picked up for a mini-prep followed by Sanger sequencing. The result showed that nine out ten clones contained a random ligation promoter with 6 to 20 TREs. Each TRE showed in at least one clone with NFkB had the highest frequency, which was consistent with the TRE mixing ratio in the ligation pool (FIG. 8).

Figure 9:
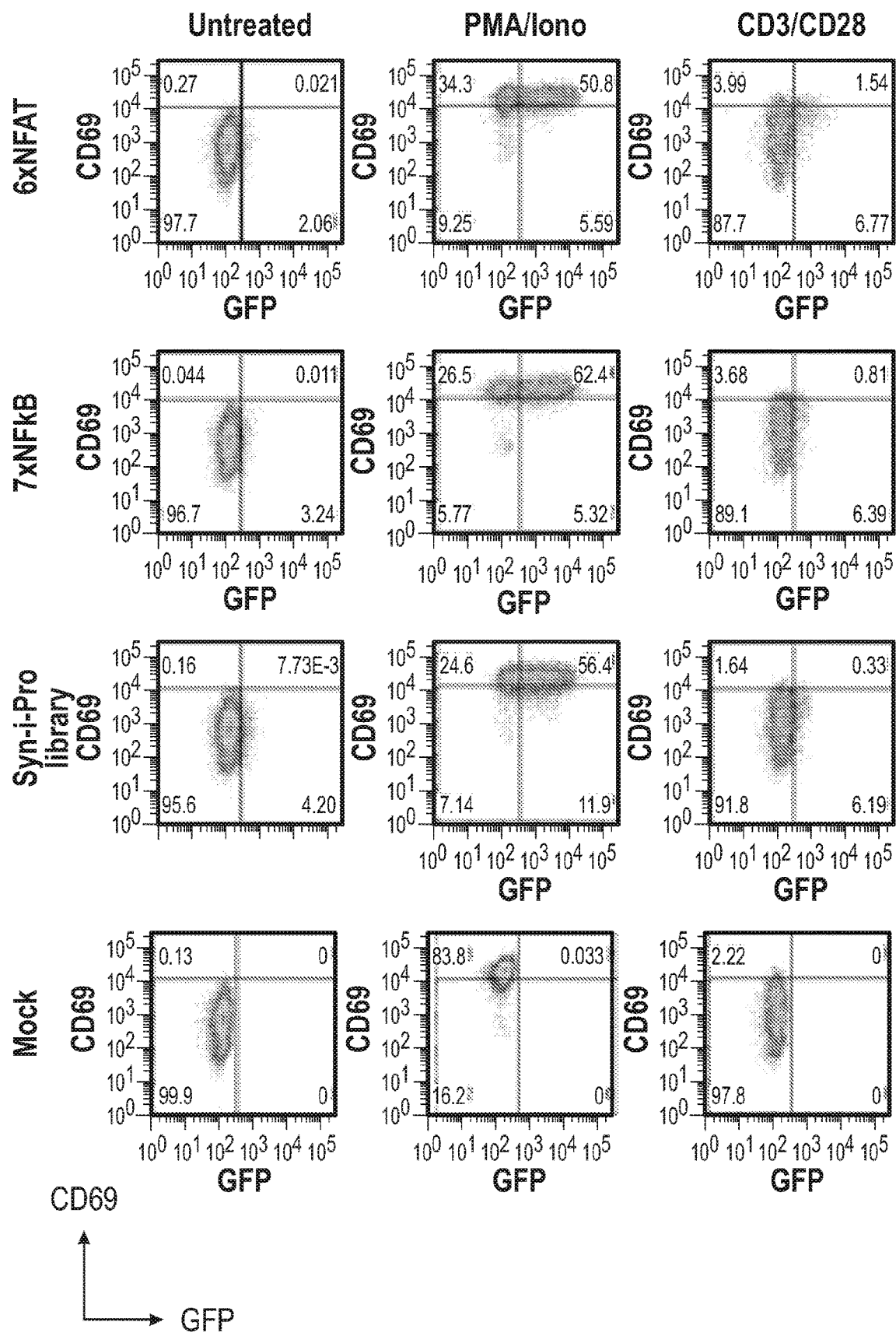
FIG. 9 shows a series of FACS assays used to evaluate iSynPro library Jurkat cells as compared with NFAT and NFkB regulated promoters.

Cells expressing the TCR under the control of a Syn-iPro synthetic promoter were analyzed by FACS for the expression of CD69 and GFP upon contact with PMA/Iono or anti-CD3/anti-CD28. As shown, the use of the Syn-iPro synthetic promoter under control of the chemical PMA/Iono lead to expression of CD69/GFP (FIG. 9).

Figure 10:
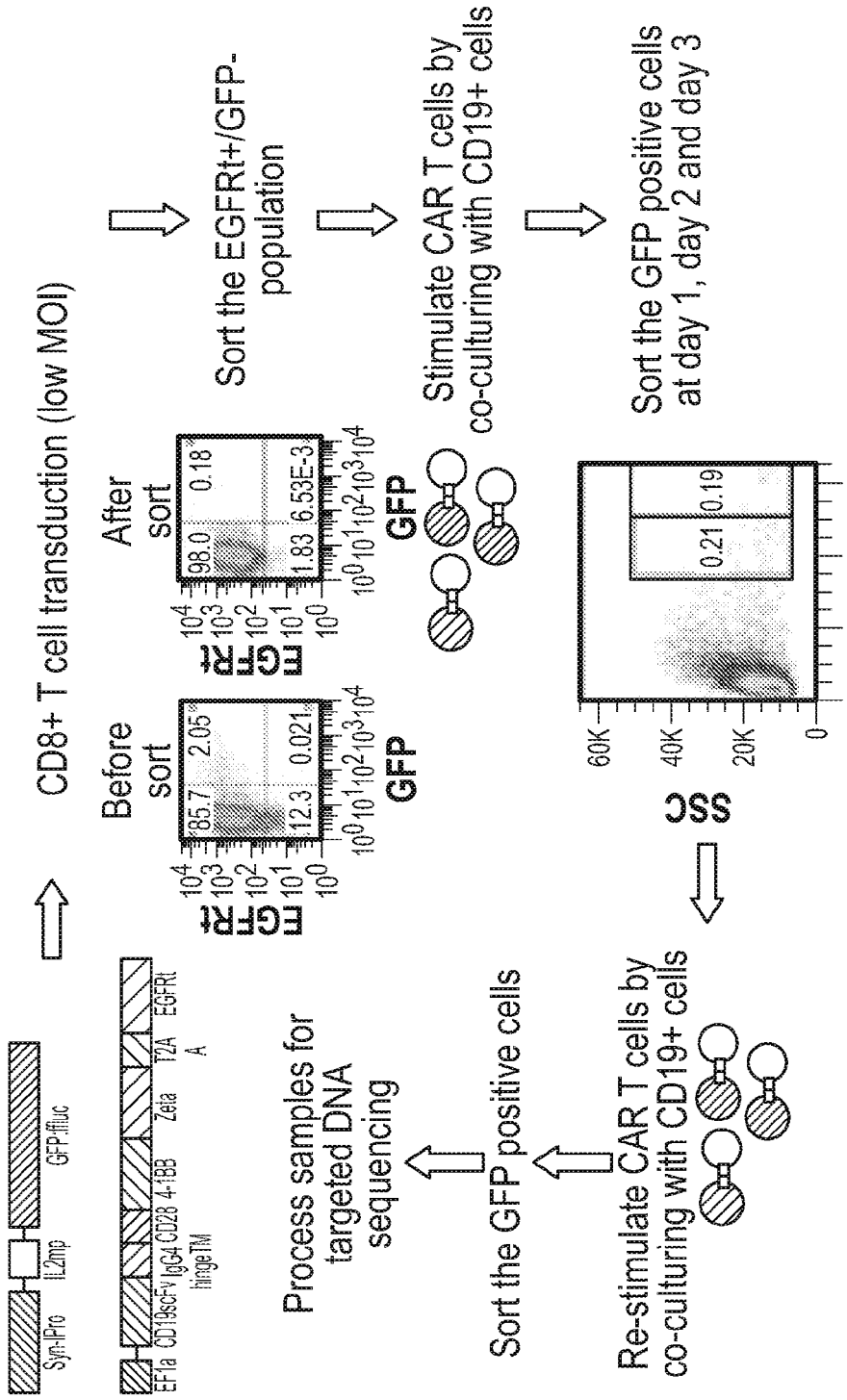
FIG. 10 is an example of screening the library of promoters in CD8 primary T cells. As shown, the cells are first co-transduced with nucleic acids that have the iSynPro-IL2mp promoter for driving the expression of GFP and a nucleic acid that expresses the CD19 with a EGFRt marker protein. The cells are then activated with anti-CD$^3$/anti-CD28 beads, which are then subsequently removed. Cells are then sorted for an EGFRt+ and a GFP-population. The cells are then stimulated by co-culturing with CD19+ cells and then the GFP positive cells are sorted at days 1, 2, 3 as well as the day after re-stimulation.

The library of the Syn-iPro synthetic promoter was screened in CD8 primary T cells (FIG. 10). The second generation CD19CAR-T2A-EGFRt used in the clinical trials had been thoroughly studied and shown promising results. Therefore, the second generation CD19CAR-T2A-EGFRt was used to trigger the iSynPro library expression by co-transducing it with iSynPro library. To avoid screening out false positive sequences generated by piggy back effect, the library needed to be transduced at a low MOI so that each single cell contains at most one iSynPro sequence. A cell system that contains a "quiescent" stage or an "OFF" stage and a CAR activated stage or an "ON" stage was also required. To avoid screening out constitutively active promoters or those that were GFP positive in the absence of a CAR, only EGFRt positive and GFP negative cells at a "quiescent" stage (7 days after anti-CD$^3$/anti-CD28 beads removal) were sorted out using a flow cytometer sorter. These cells were then co-cultured with irradiated Tm-LCL (CD19+) cells to activate CD19CAR. The GFP positive cells derived by iSynPro activation were sorted out at 24 h, 48 h, 72 h in a GFP medium and a GFP high gate. The remaining cells were continuously cultured for another week and then co-cultured again with Tm-LCL cells. The GFP positive cells were sorted out 24 h later.

Figure 11:
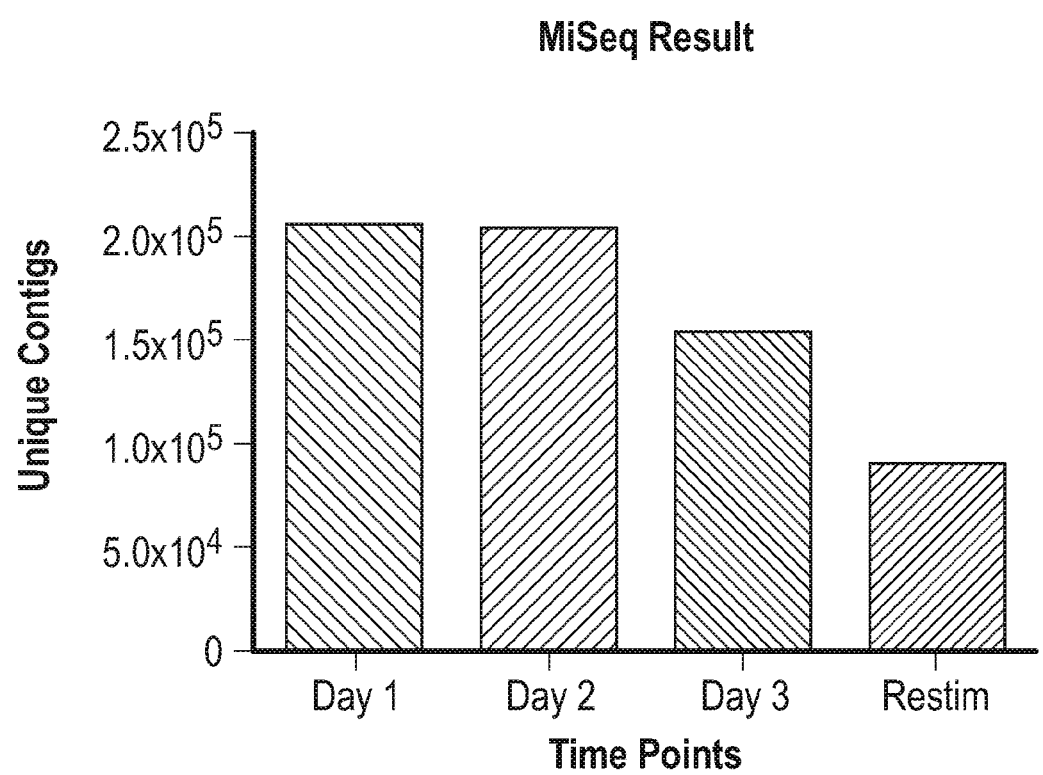
FIG. 11 shows the next generation MiSeq sequencing of the iSynPro library in the sorted cells in a bar graph. As shown, the unique contigs expressed by the cells are provided at the time points days 1, 2, 3 and the day after re-stimulation.
Figure 23:
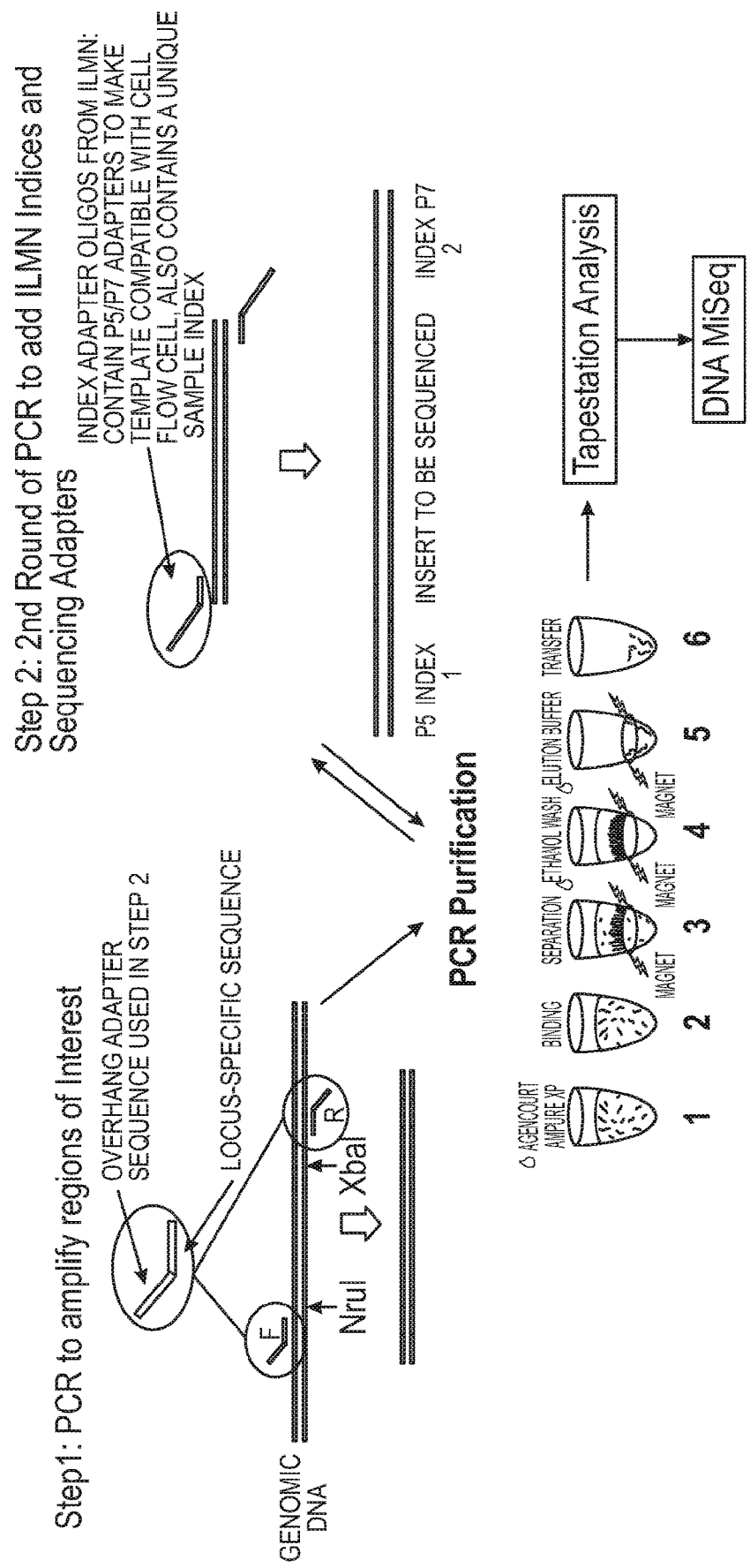
FIG. 23 is a schematic for sample processing for targeted DNA sequencing. As shown, step 1 comprises PCR to amplify regions of interest. Step 2 comprises a second round of PCT to add ILMN indices and sequencing adaptors. Step 3 comprises PCR purification, tape station analysis and DNA MiSEQ.
Figure 24:
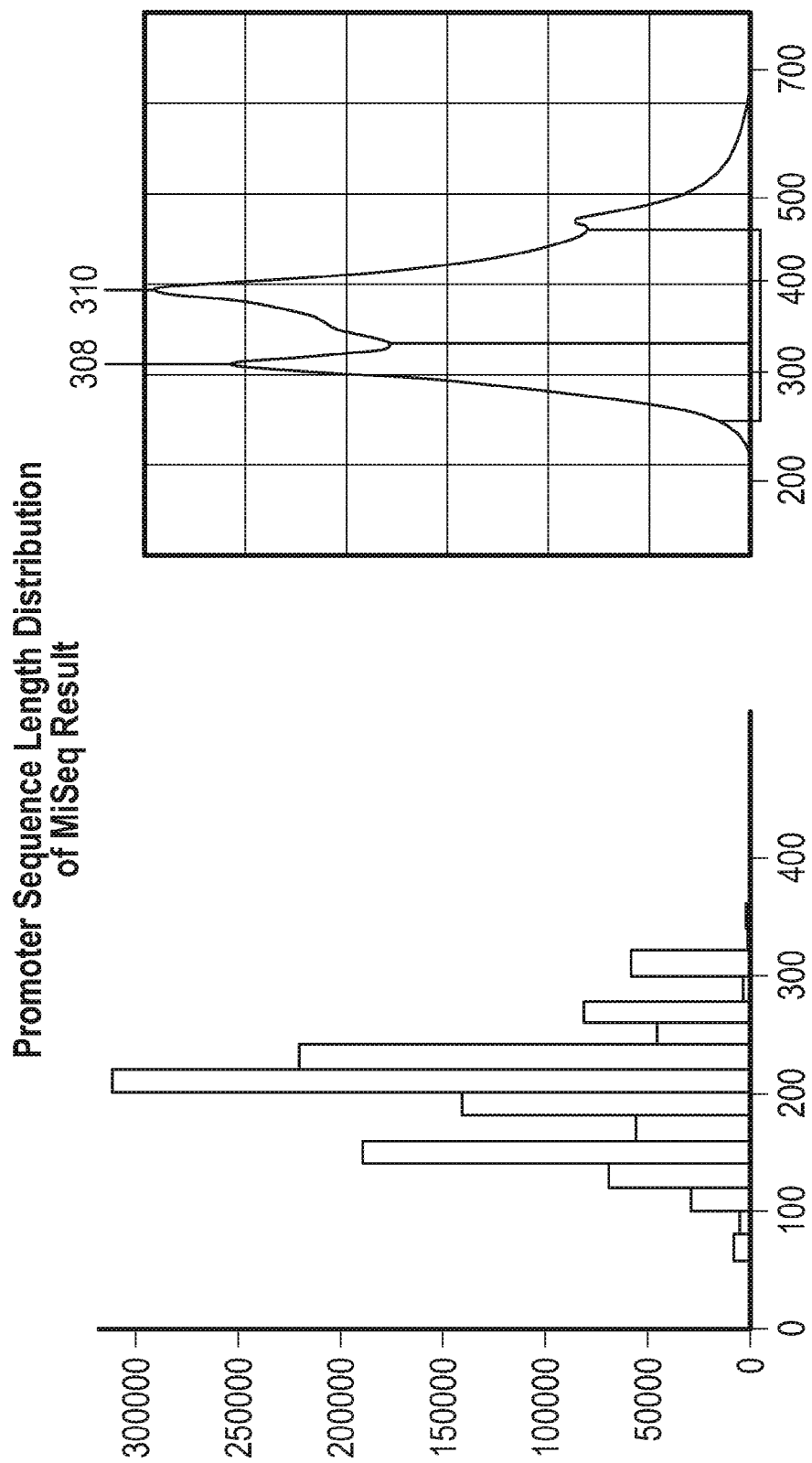
FIG. 24 shows two graphs demonstrating the promoter length distribution of the MiSeq result.
Figure 25:
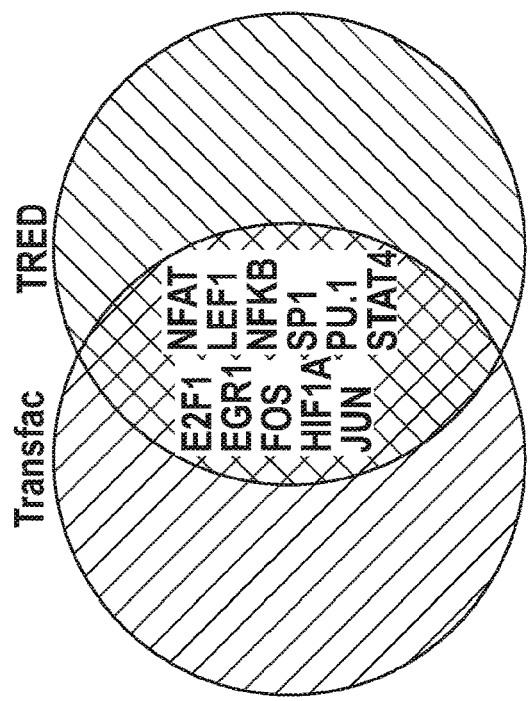
FIG. 25 shows the DNA sequencing result summary. Shown in the outlined area of the graph are the total number of unique contigs that were identified by the sequencing.
Figures 1, 26:
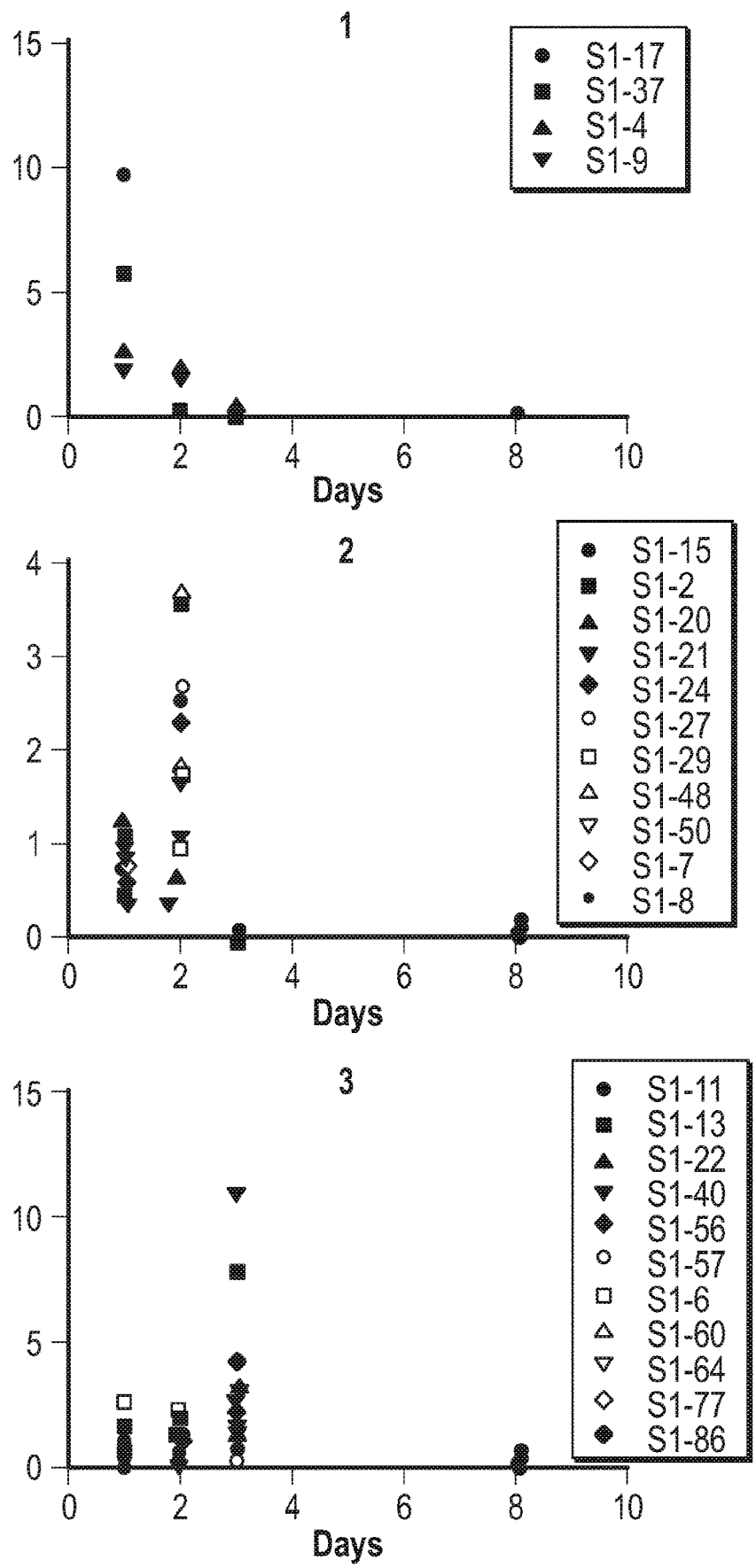
FIG. 26 analysis of iSynPro promoters.
Figures 2, 26:
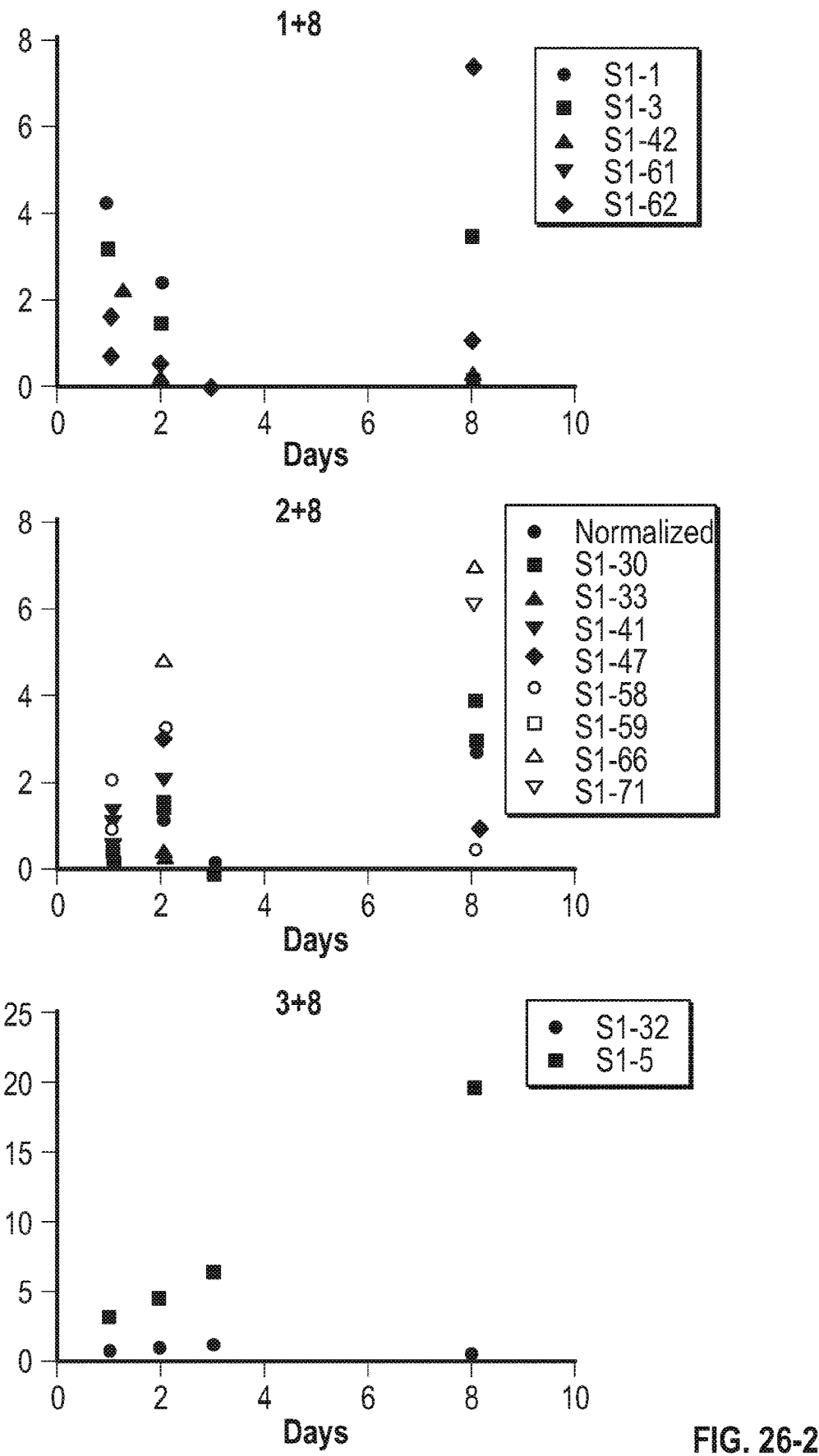
Figures 3, 26:
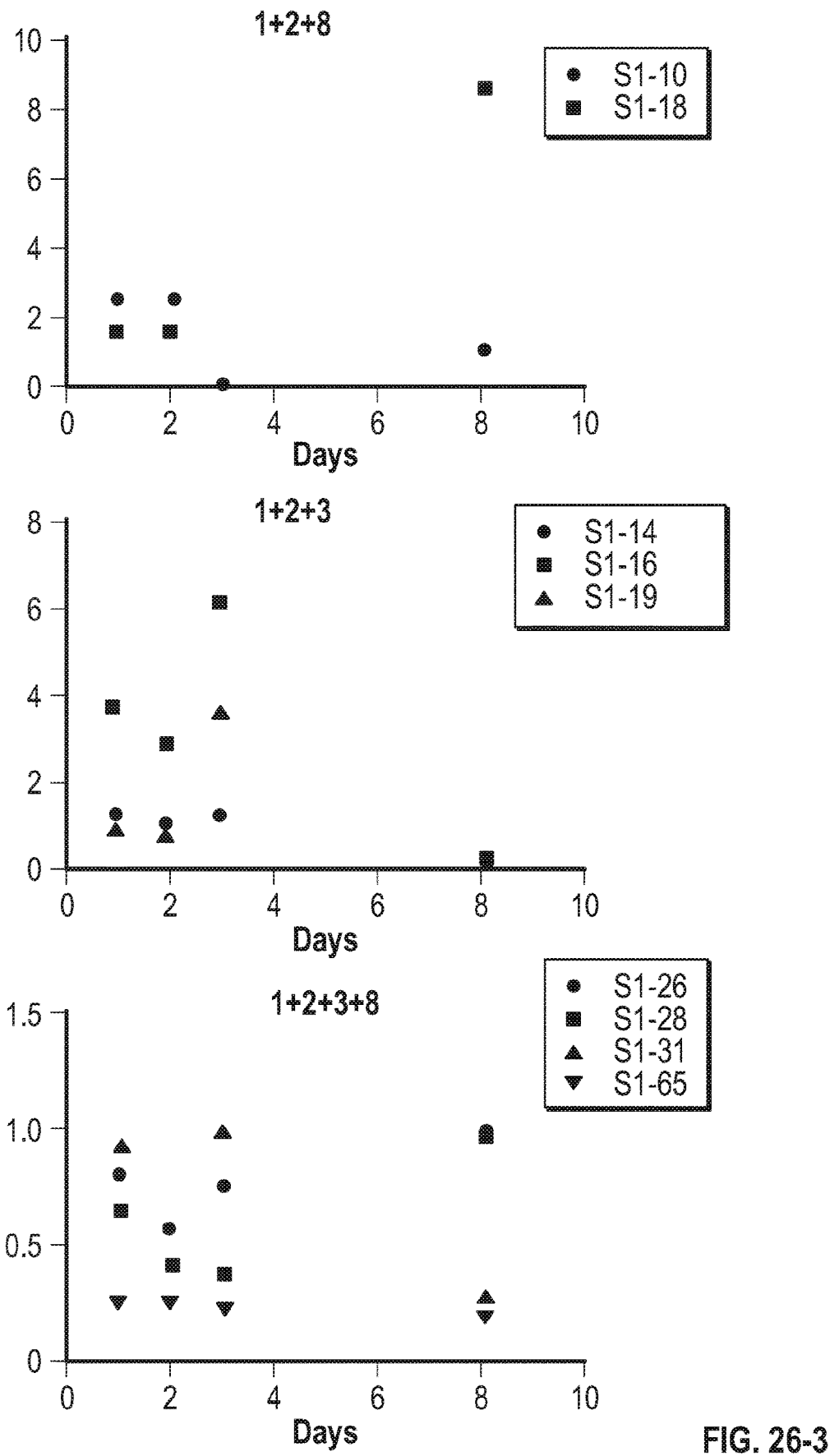

As shown in FIG. 11, the cells were screened at days 1, 2, 3 and after re-stimulation with the PMA/Iono for the number of unique contigs expressed. The sample processing for the targeted DNA sequencing is shown in FIG. 23. As shown, PCR was used to amplify the regions of interest and then purified. The purified DNA sequences were then subjected to a second round of PCR to add LMN indices and sequencing adaptors. This was then followed up with DNA MiSeq sequencing (FIG. 24). The sequences were then analyzed for total unique contigs per time point (FIG. 11). From left to right are total number of unique contigs at day1, day2, day3 post stimulation and one day after restimulation. Twenty eight (28) top hits from each pattern were used to analyze the clones for unique expression patterns and to evaluate the induction by specific CAR bearing T cells.

Figure 12:
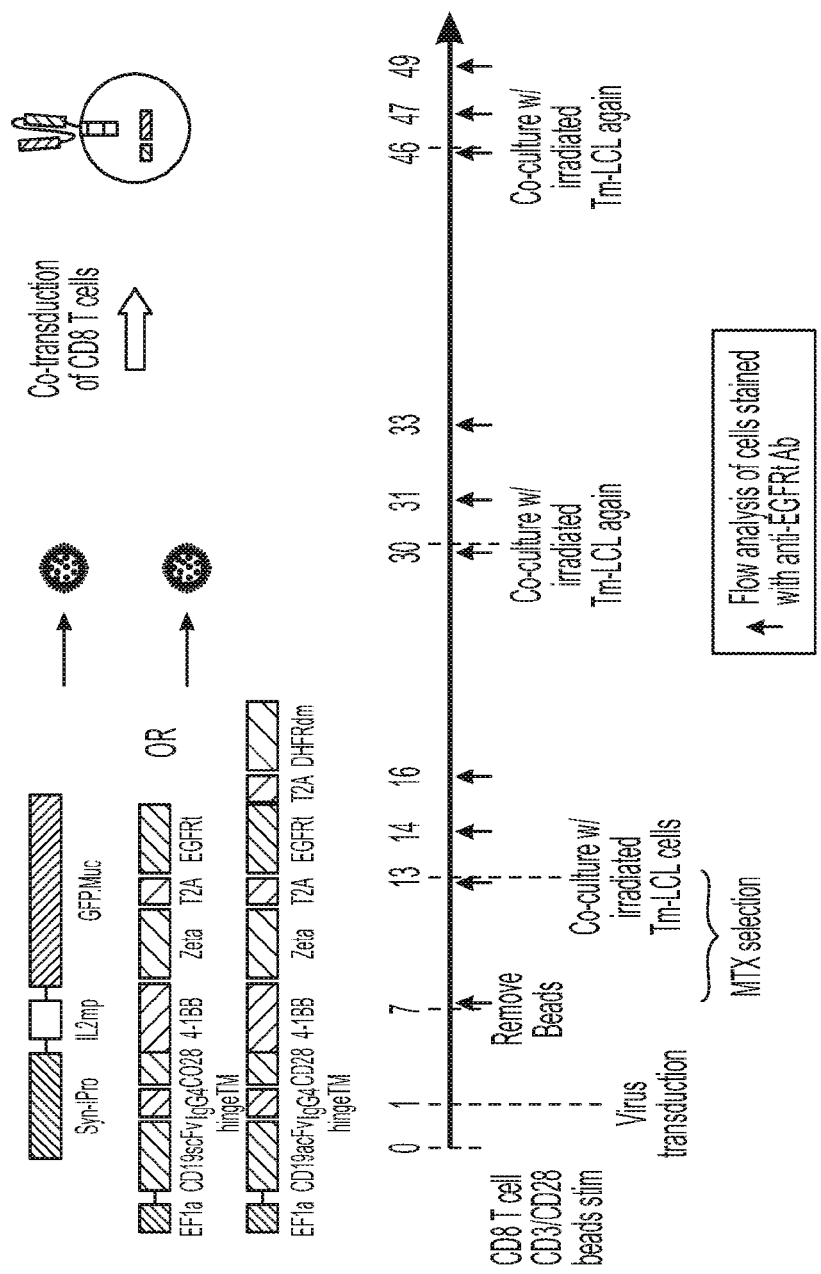
FIG. 12 is a schematic showing the protocol for iSynPro verification in CD8 T cells from two donors. Shown are 3 nucleic acids for: a) expression of the iSynPro promoter-IL2mp for driving GFP expression; b) nucleic acid for expression of CD19 with an EGFRt marker; and c) a nucleic acid for expression of CD19+ with a EGFRt marker and a DHFRdm promoter drug inducible promoter. Cells are transduced with the nucleic acids a) and b) or c). As shown, the cells are stimulated with anti-CD$^3$/anti-CD28 beads and after 24 hours the cells are transduced. Beads are removed and MTX selection is applied. The cells are then co-cultured with irradiated Tm-LCL cells at day 13. At day 30 and 46, the cells are again co-cultured with irradiated Tm-LCL cells
Figure 13:
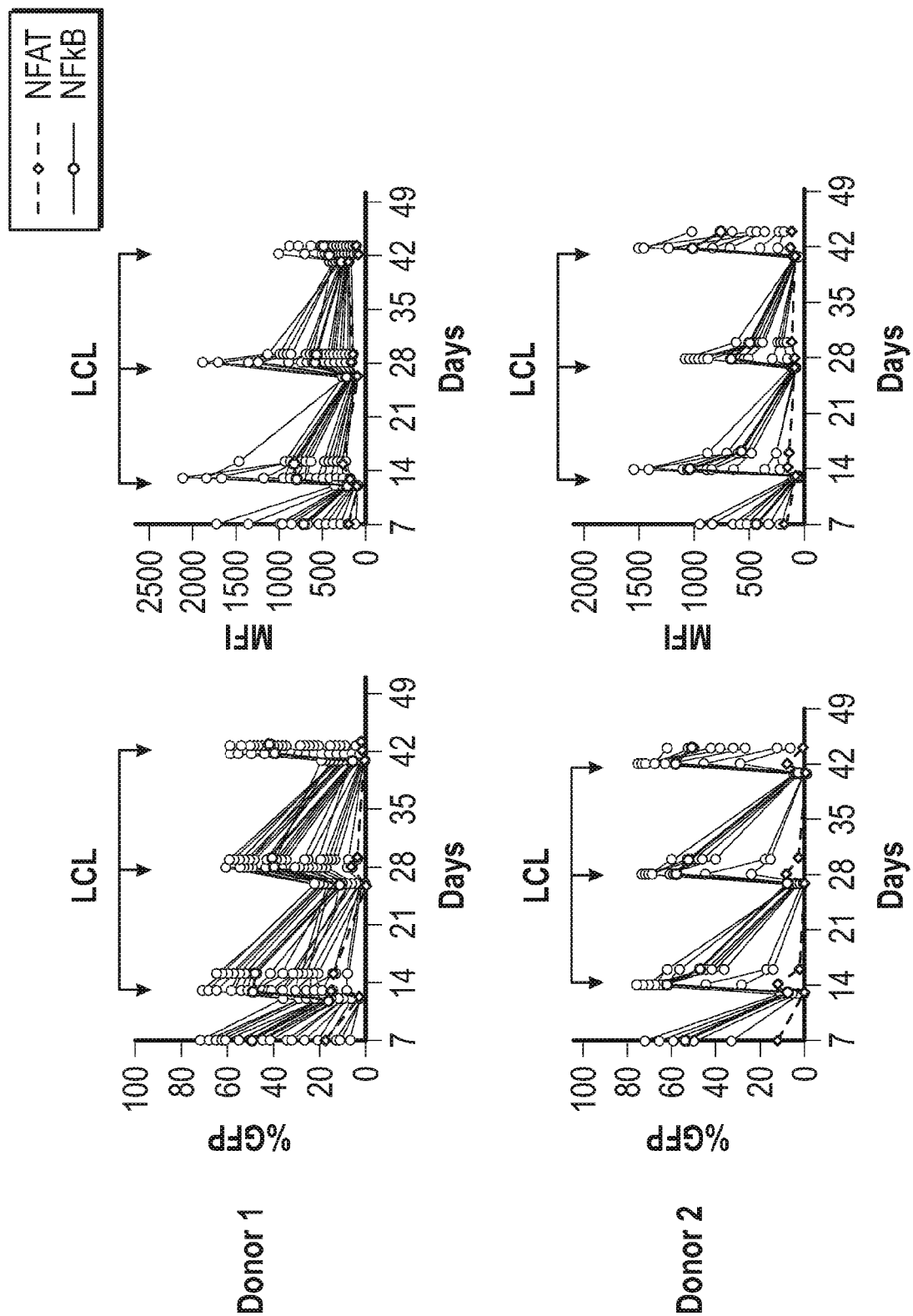
FIG. 13 shows the result of verification of iSynPros in CD8 T cells from two different donors using the method as shown in FIG. 14. After anti-CD3/anti-CD28 beads activation, CD8 T cells are co-transduced with CD19CAR and iSynPro library. Six days after beads removal the cells are co-cultured with irradiated Tm-LCL cells and part of the cells are harvested for flow cytometry analysis at 24 h and 72 h. The remaining cells are restimulated with Tm-LCL after two weeks in culture, which is followed by another round of restimulation. The selected 28 iSynPro top hits are first verified in donor #1 CD8$^+$ T cells. The GFP signal is turned on at various extent through endogenous TCR by the anti-CD$^3$/anti-CD28 beads and goes back to baseline after beads removal. This up and down signal is repeatedly observed for at least three cycles when the CD19CAR positive T cells encounter irradiated Tm-LCL cells. Overall, upon induction, 27 out of 28 iSynPros show a higher GFP positivity and a higher MFI than 6×NFAT promoter; half of them have a higher GFP positivity and ten of them have a higher MFI than 7×NFkB. The experiment is then repeated in donor #2 cells using 9 out of 28 iSynPros. This time a drug selection marker DHFRdm is incorporated into the CD19CAR construct, which allows us to select out a purer population. A very similar result is seen as before.
Figure 14:
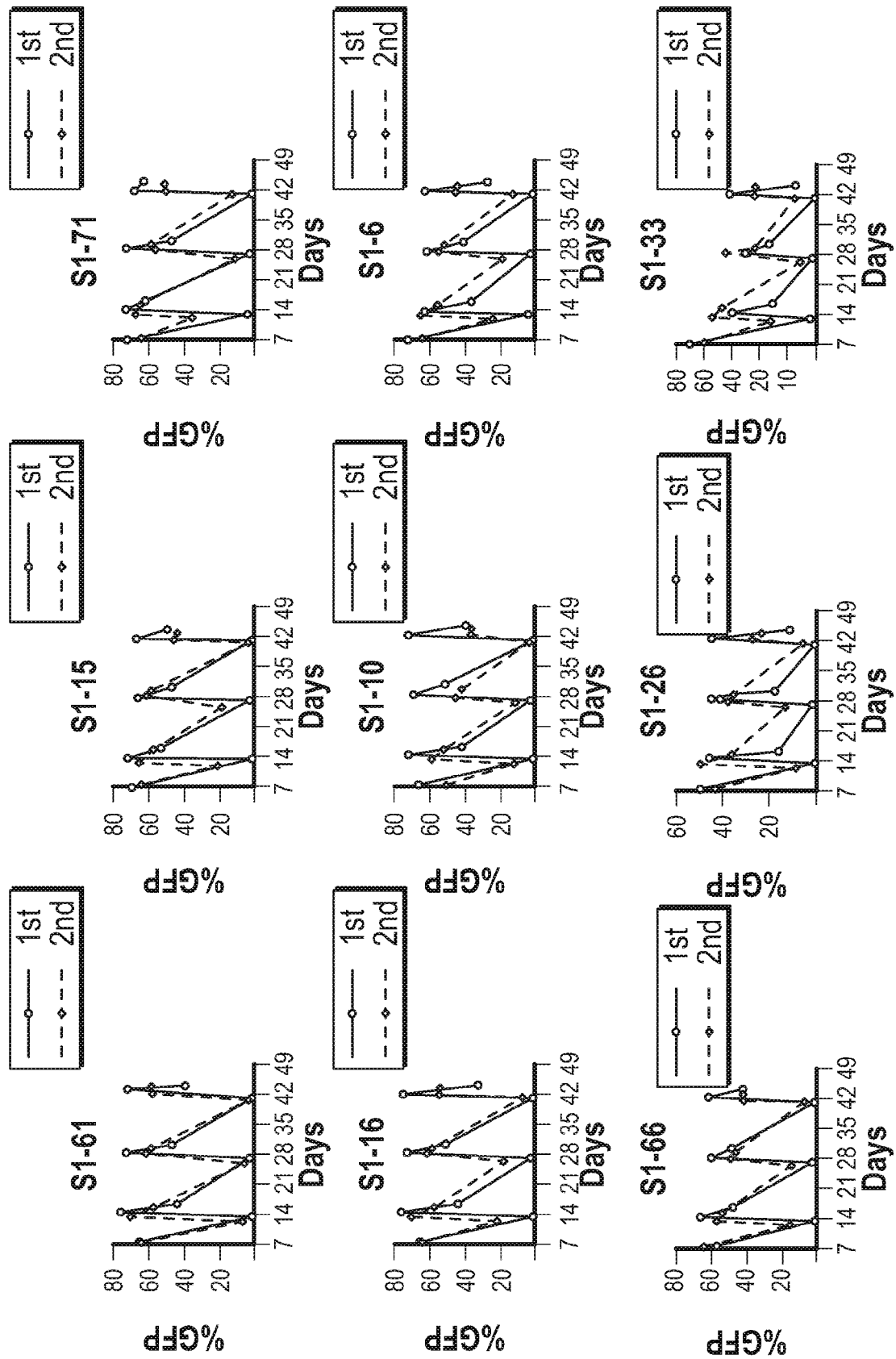
FIG. 14 shows the overlay of the iSynPro regulated GFP expression results from the two donor cells above. Both % GFP and MFI results are very similar between the two donor cells, which means the induction of iSynPros are consistent and robust.
Figure 15:
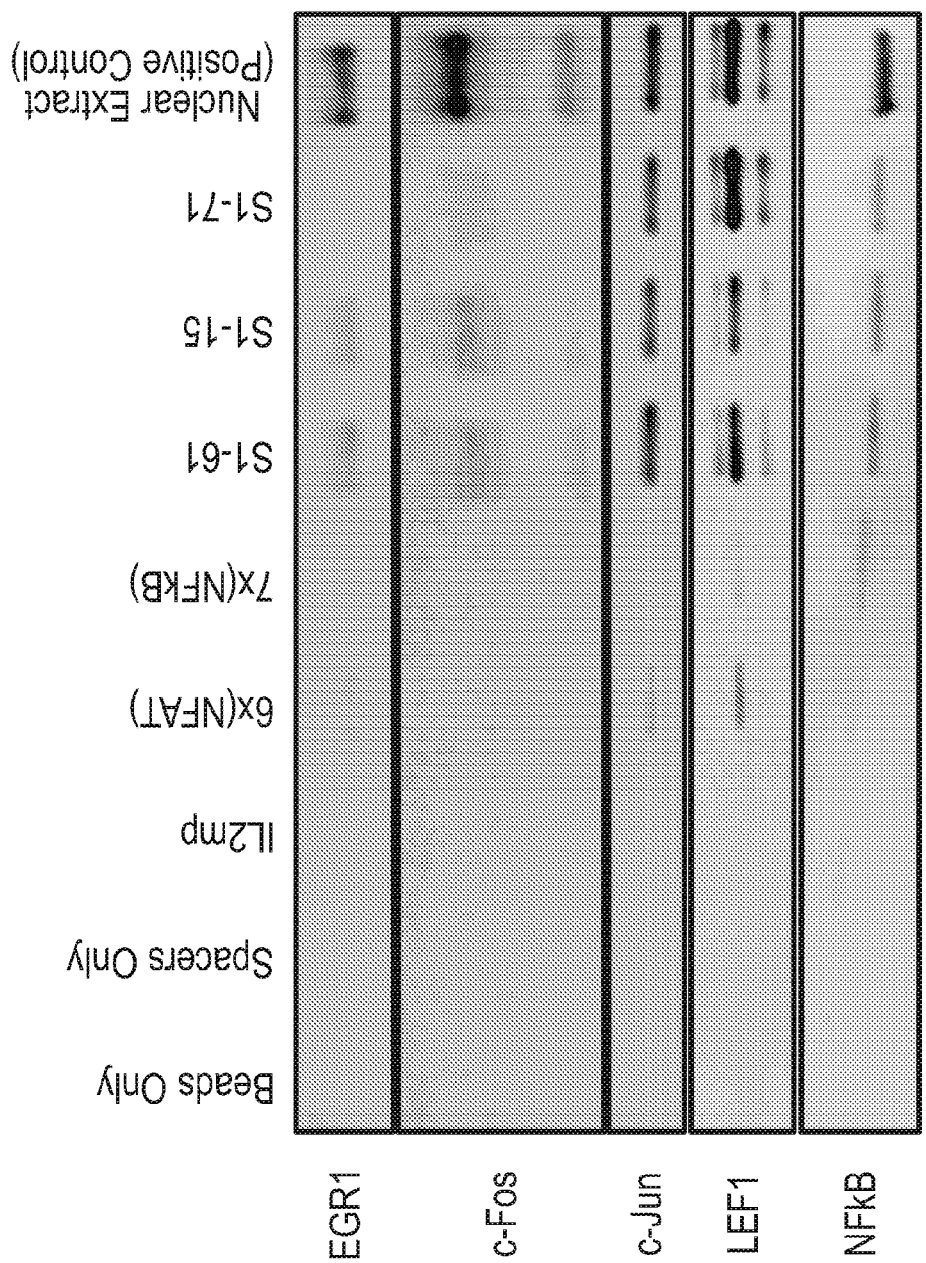
FIG. 15 shows a transcription factor pull down assay. Method: iSynPro sequences and control sequences were PCR amplified using biotinylated primers. Nuclear extract is isolated from PMA/Ionomycin treated Jurkat cells and incubated with biotinylated double stranded iSynPro DNA (three iSynPro sequences are tested here) followed by streptavidin conjugated magnetic beads pull down. The transcription factors pulled down with the promoter DNA are denatured, applied to a SDS-PAGE gel and immunoblotted by antibodies targeting to the predicted transcription factors whose corresponding TREs show in at least two of the three iSynPro sequences tested here.

CD8+ cells were also transfected with a first vector comprising a Syn-iPro synthetic promoter linked to a minimal promoter (Il2mp) for the expression of GFP). The cells were co-transfected with either vector: a) nucleic acid for expression of CD19 with an EGFt marker or b) a nucleic acid for expression of CD19+ with an EGFRt marker and a DHFRdm promoter drug inducible promoter (FIG. 12). Analyzing the Syn-Pro for expression can be performed as in the method outlined in FIG. 27. Cells were then harvested and analyzed for protein expression using a pull down assay.

Figure 16:
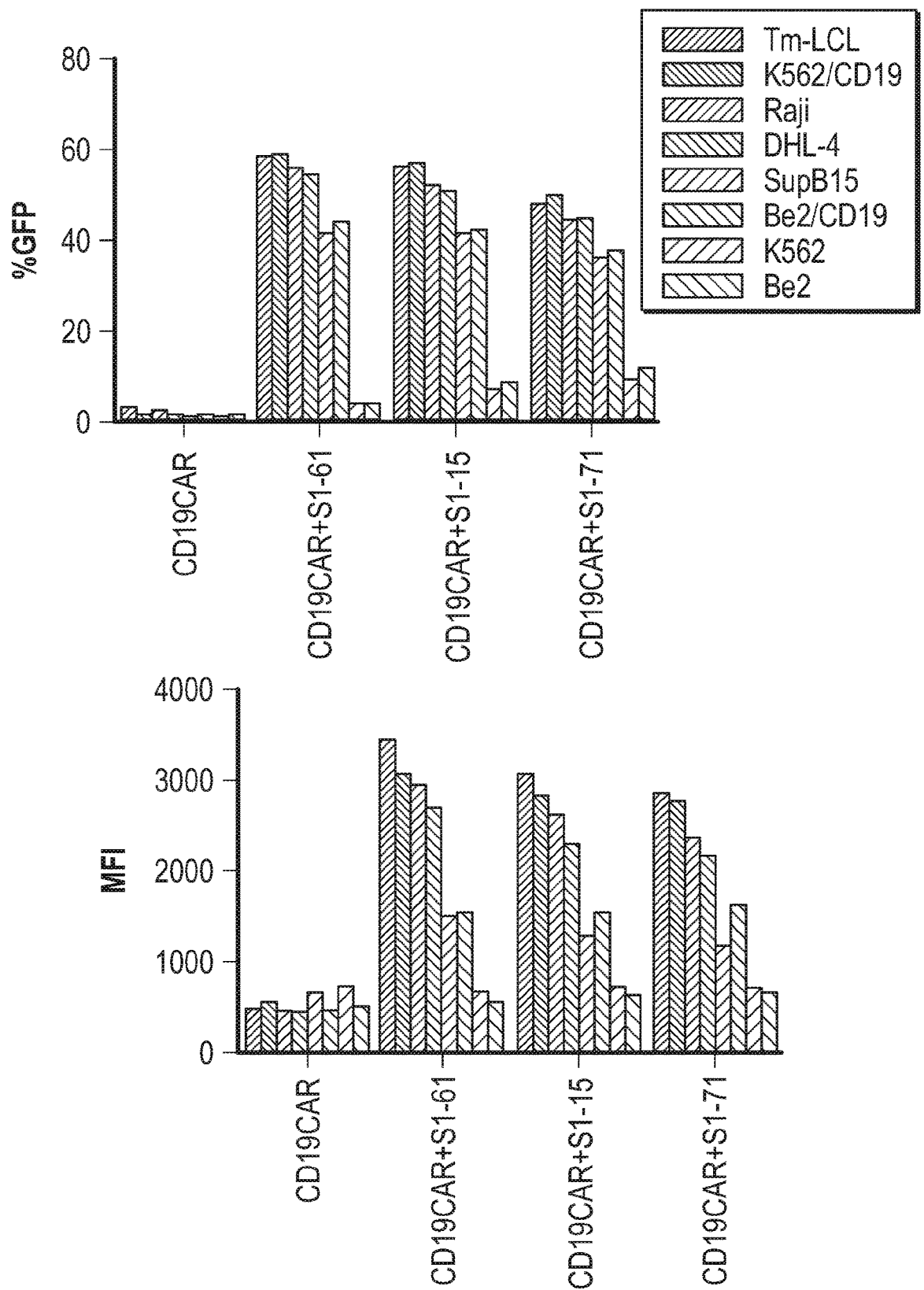
FIG. 16 shows that the iSynPro can be activated through the interaction of CD19CAR and the different CD19+ cells. Shown from left to right consecutively is the expression of GFP after stimulation of cells that carry: Tm-LCL, K562/CD19, Raji, DHL-4, SupB15, Be2/CD19, K562 and Be2.
Figure 17:
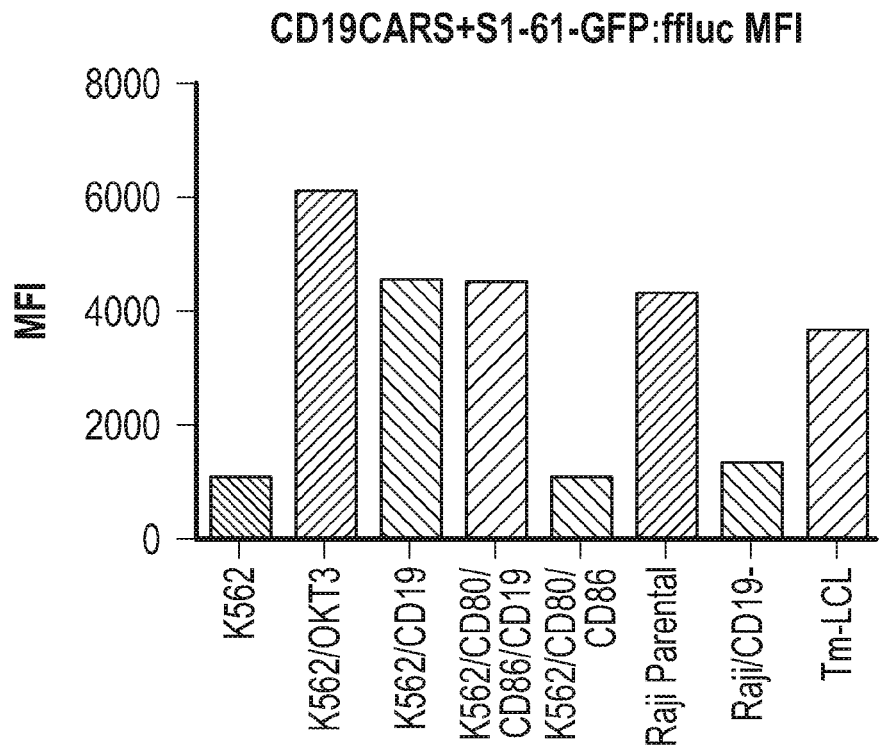
FIG. 17 is a series of bar graphs showing the results of activation of iSynPro S1-61-GFP:ffluc and 7×NFkB-GFP:ffluc in CD19CAR T cells by different target cell lines expressing T cell costimulators (CD28 receptors) CD80 and CD86. From left to right are K562, K562/OKT3, K562/CD19, K562/CD80/CD86/CD19, K562/CD80/CD86, Raji, Raji/CD19−, and Tm-LCL. Parental K562 cells do not express CD19, CD80 or CD86 on the surface. K562/OKT3 was used as a positive control to show the TCR activated killing. Expressing exogenous CD80/CD86 alone on K562 was unable to activate either iSynPro or 7×NFkB. The synergistic activation effect of CD80/CD86 and CD19 was only seen in 7×NFkB cells (right chart) where GFP expression was stronger in K562/CD80/CD86/CD19 than that in K562/CD19, but not in S1-61 cells (left chart). Raji and Tm-LCL cells express CD19 and CD80/CD86 at different levels. S-61 and 7×NFkB were both activated by them and the latter showed a stronger signal which was probably related to the synergistic effect of CD19 and CD80/CD86. When CD19 gene was knocked out by CRISPR, GFP expression from both promoters drastically dropped down to close to the baseline level, which further supported the observation in K562 cells from the other way around. Overall the data suggest that the T cell costimulators do not induce S1-61 or 7×NFkB and the S1-61 activation is more specific to CAR-antigen interaction than 7×NFkB. To show that induction of S1-61 or 7×NFkB coexists and correlated with CD19CAR function and not a random effect, cytokine release assay and chromium release assay were done at the same time as seen below in FIGS. 20 and 21.
Figure 17:
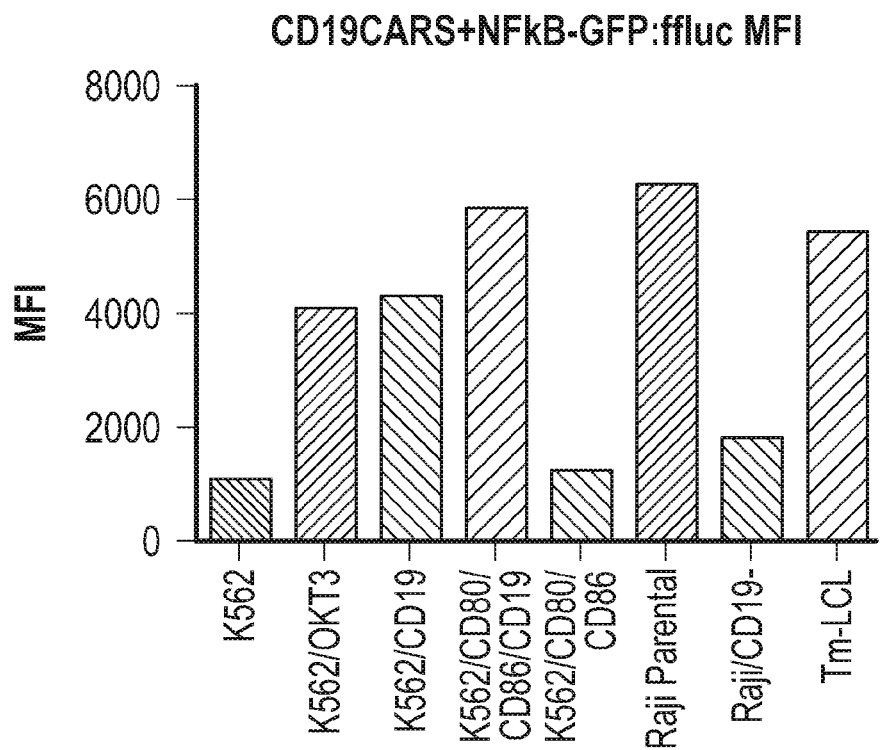

As shown in FIGS. 16 and 17, iSynPro may be activated through the interaction of CD19CAR and the different CD19+ cells. Shown from left to right consecutively are the expression of GFP due to cells carrying: Tm-LCL, K562/CD19, Raja, DHL-4, SupB15, Be2/CD19, K562 and Be2.

Figure 18:
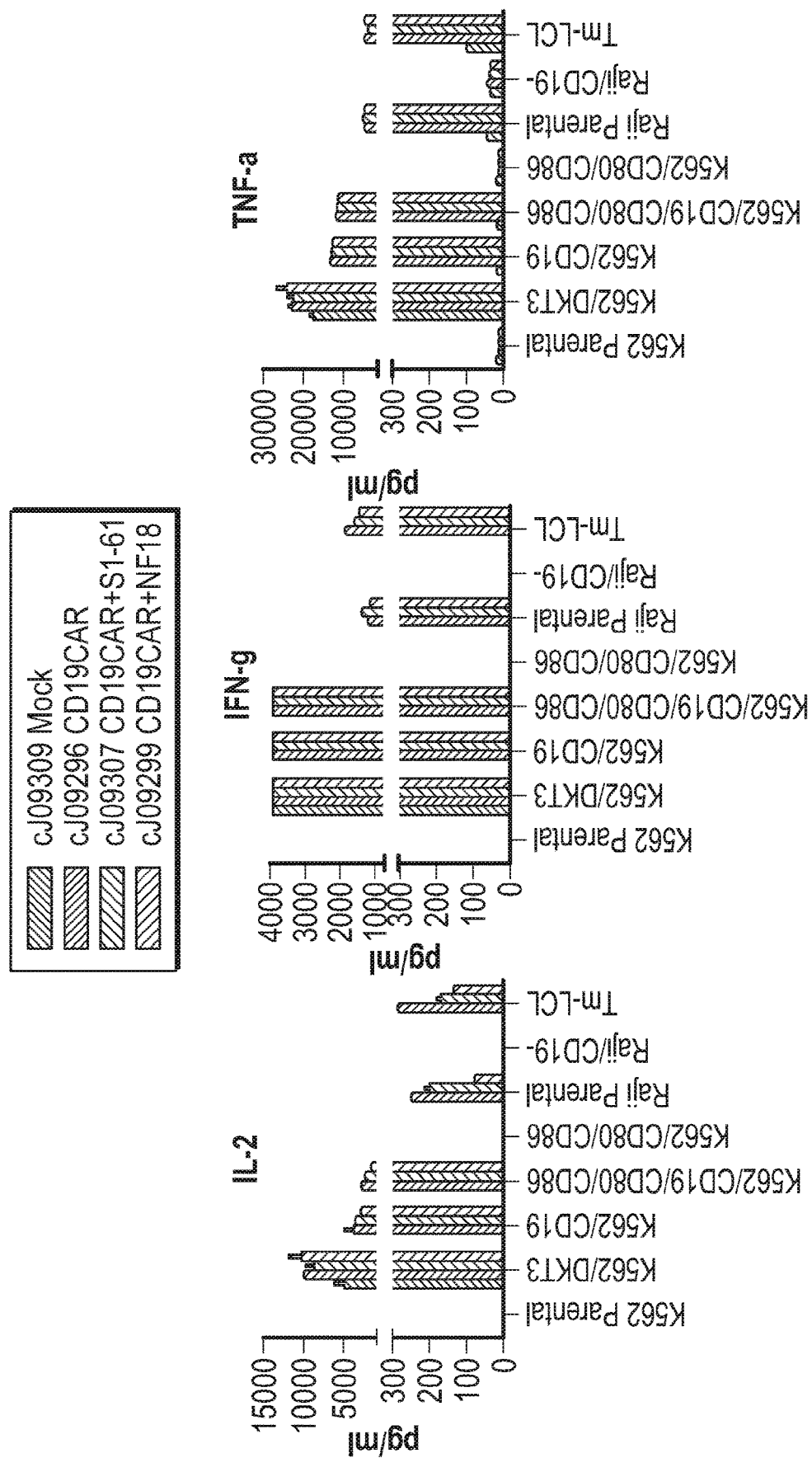
FIG. 18 shows that the CD80/CD86-costimulators alone also did not induce cytokine release in the cells. As shown in consecutive order are the cells: Mock, CD19CAR, CD19CAR+S1-61-GFP:ffluc and CD19CAR+ NFkB-GFP:ffluc. The cytokines assayed were IL-2, IFN-g and TNFa.
Figures 1, 19:
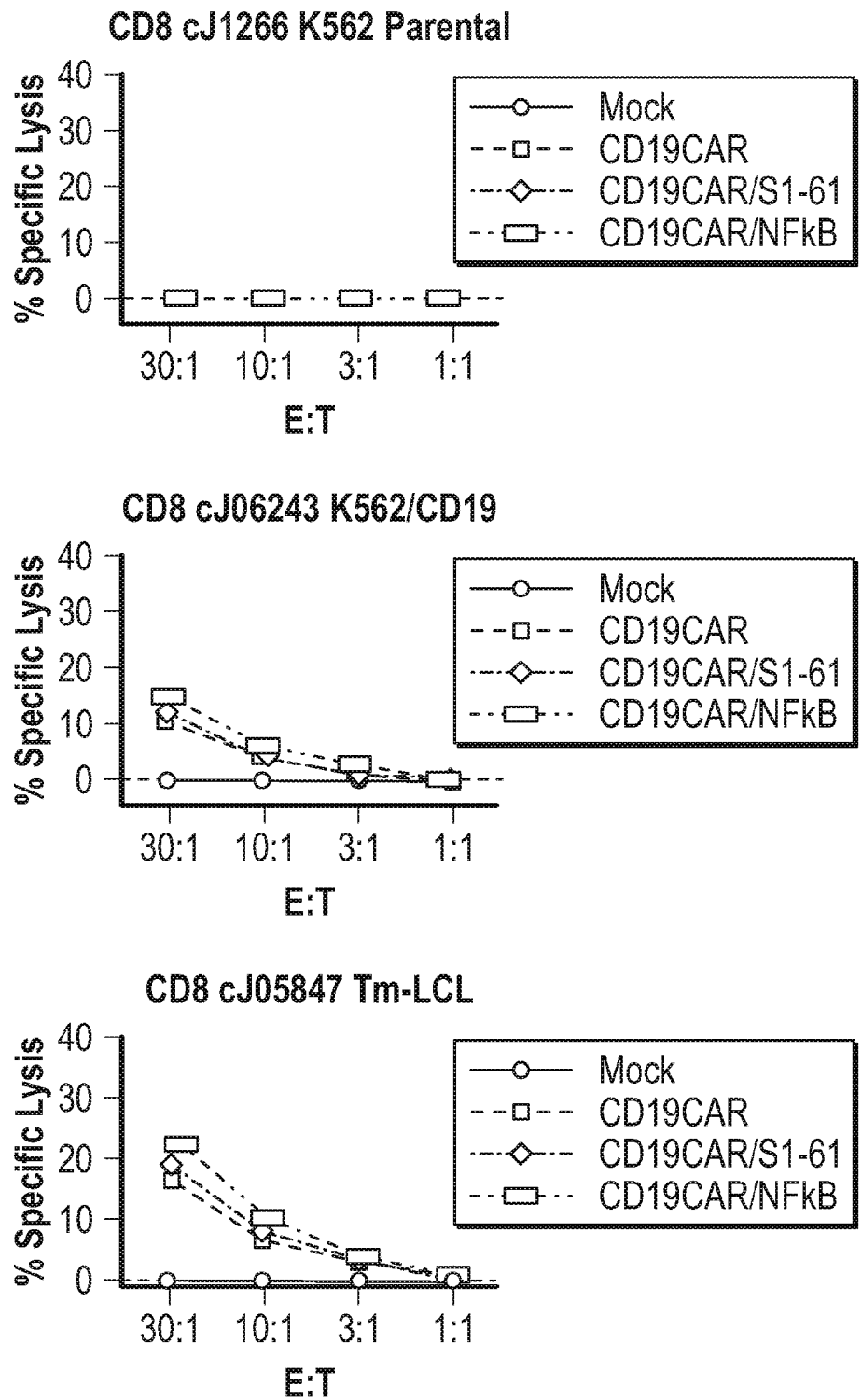
FIG. 19 shows a result of chromium release assay that demonstrates that cells expressing CD80/CD86 co-stimulators but not CD19 were not killed by CD19CAR T cells. Parental K562 cells do not express CD19, CD80 or CD86 on the surface. The data showed that K562 cells were only killed by CD19CAR T cells when exogenous CD19 is expressed but not CD80/CD86. Method: CD19CAR target cells were labeled with Cr51 and then co-cultured with serial diluted effector cells to achieve different effect:target ratios, 30:1, 10:1, 3:1, 1:1. The labeled target cells were also cultured with 2% SDS or RPMI medium as a positive and a negative control. After four hours of incubation, the supernatant was harvested and transferred to LUMA 96-well plates. The plates were dried overnight and then read by TopCount microplate scintillation counter.
Figures 2, 19:
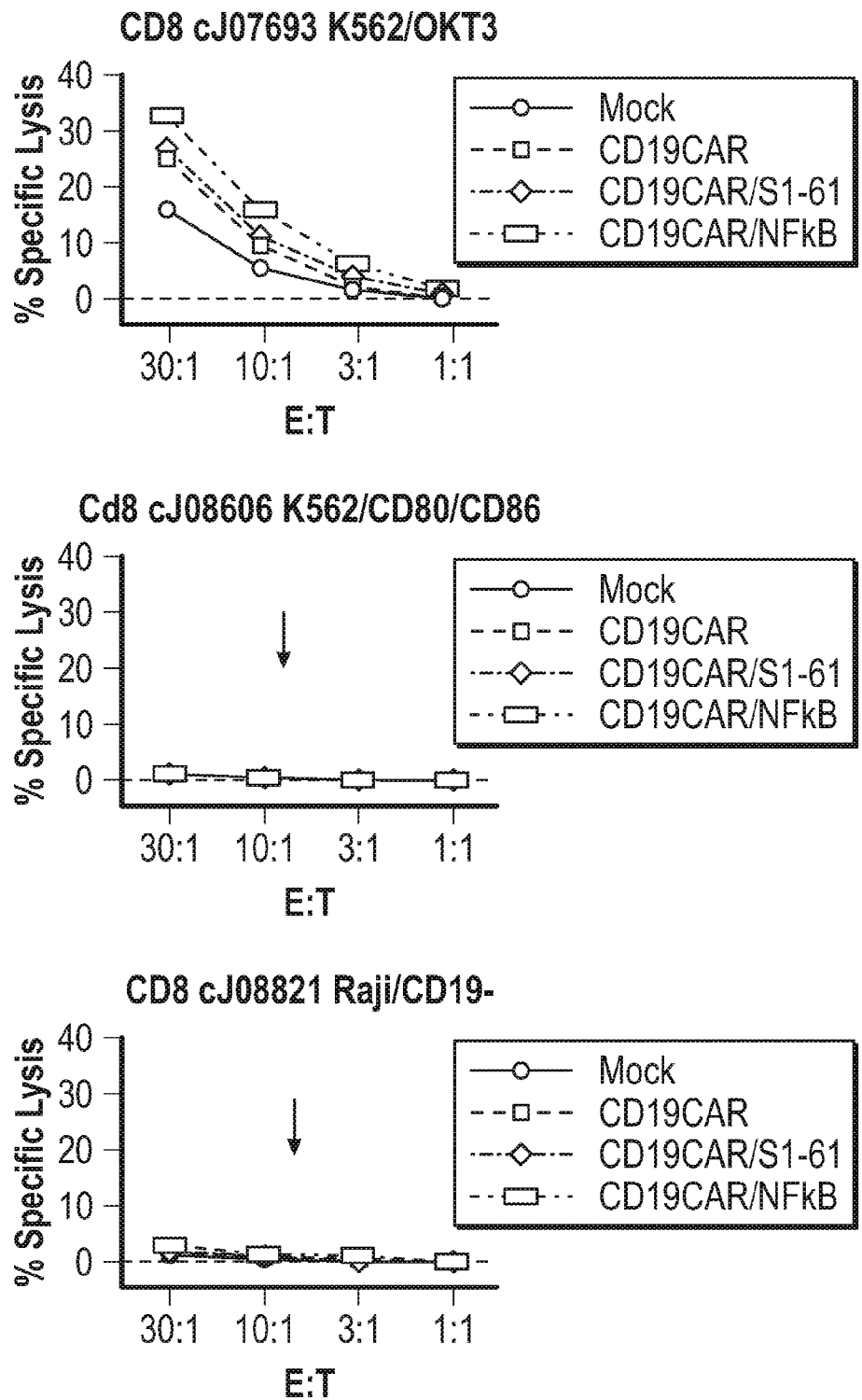

Cells were also analyzed for expression of cytokines (Il-2, IFNg and TNFa). As shown, CD/CD86-costimulators also did not induce cytokine release in the cells. However, the cells comprising the Syn-ipro promoter nucleic acids are activated or stimulated by cells that are CD19+CAR T cells. (FIG. 18). As shown in FIG. 19, cells expressing CD80/CD86 co-stimulators were not killed by CD19CAR T cells (top right panel, middle left panel and bottom left panel).

Figure 20:
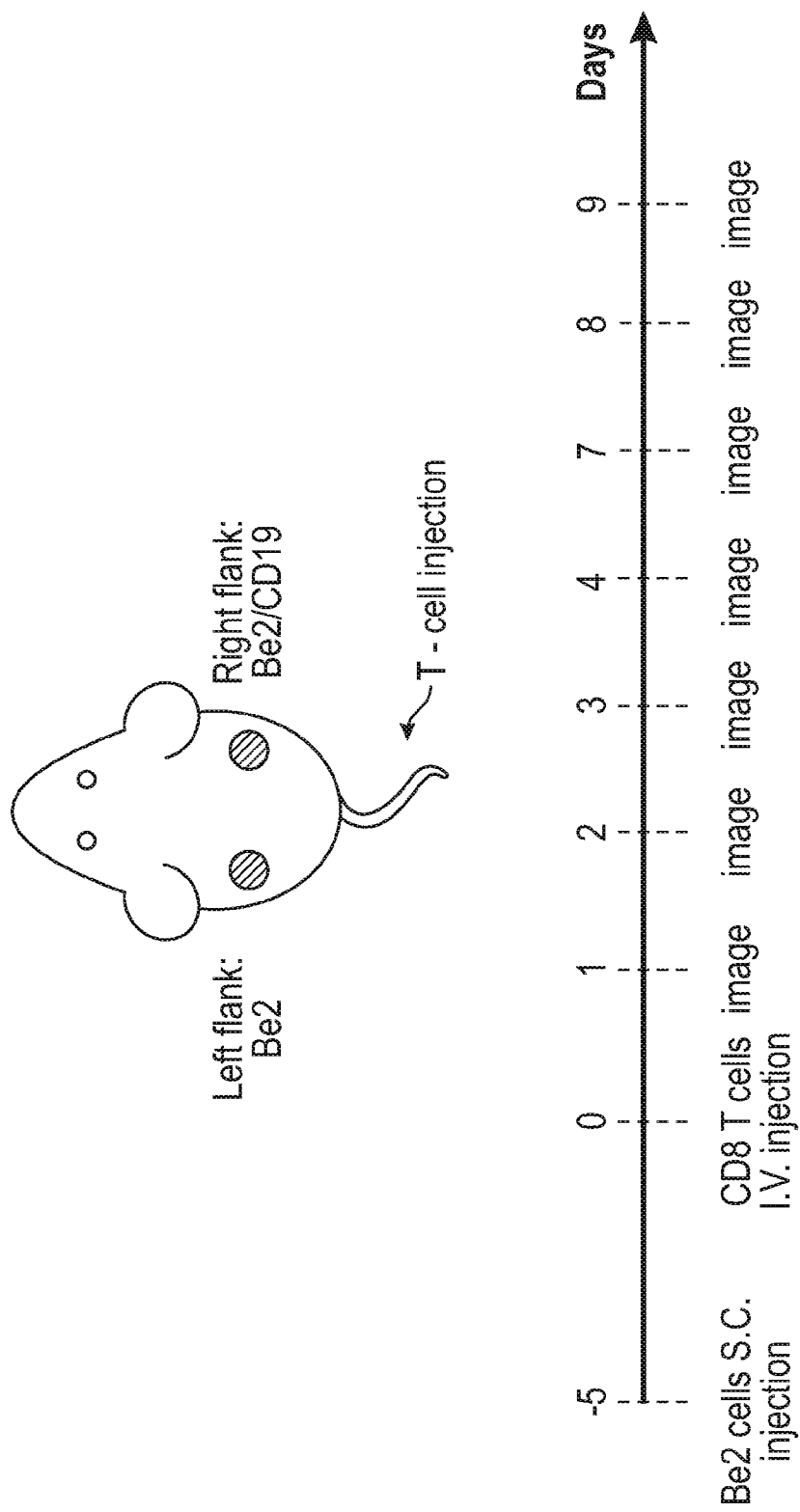
FIG. 20 shows a pilot iSynPRo in vivo study using the Be2/CD19 subcutaneous model. Shown in the figure is a timeline of the protocol. Fifteen NSG mice were divided into three groups with 5 mice each. Group A mice received 3 million of Be2 cells subcutaneously on each side of the flank. Group B mice received 3 million of Be2 cells on the left flank and 3 million of Be2/CD19 cells on the right flank. Group C mice received 3 million of Be2/CD19 cells on each side of flank. Five days post tumor engraftment, 2.5 million of CD8 T cells expressing CD19CAR/S1-61-GFP:ffluc were i.v. injected into every mouse from each group. Luminescent images were taken one day after T cell injection and continuously taken for a few days to track the luciferase expression in the engrafted T cells.
Figures 1, 21:
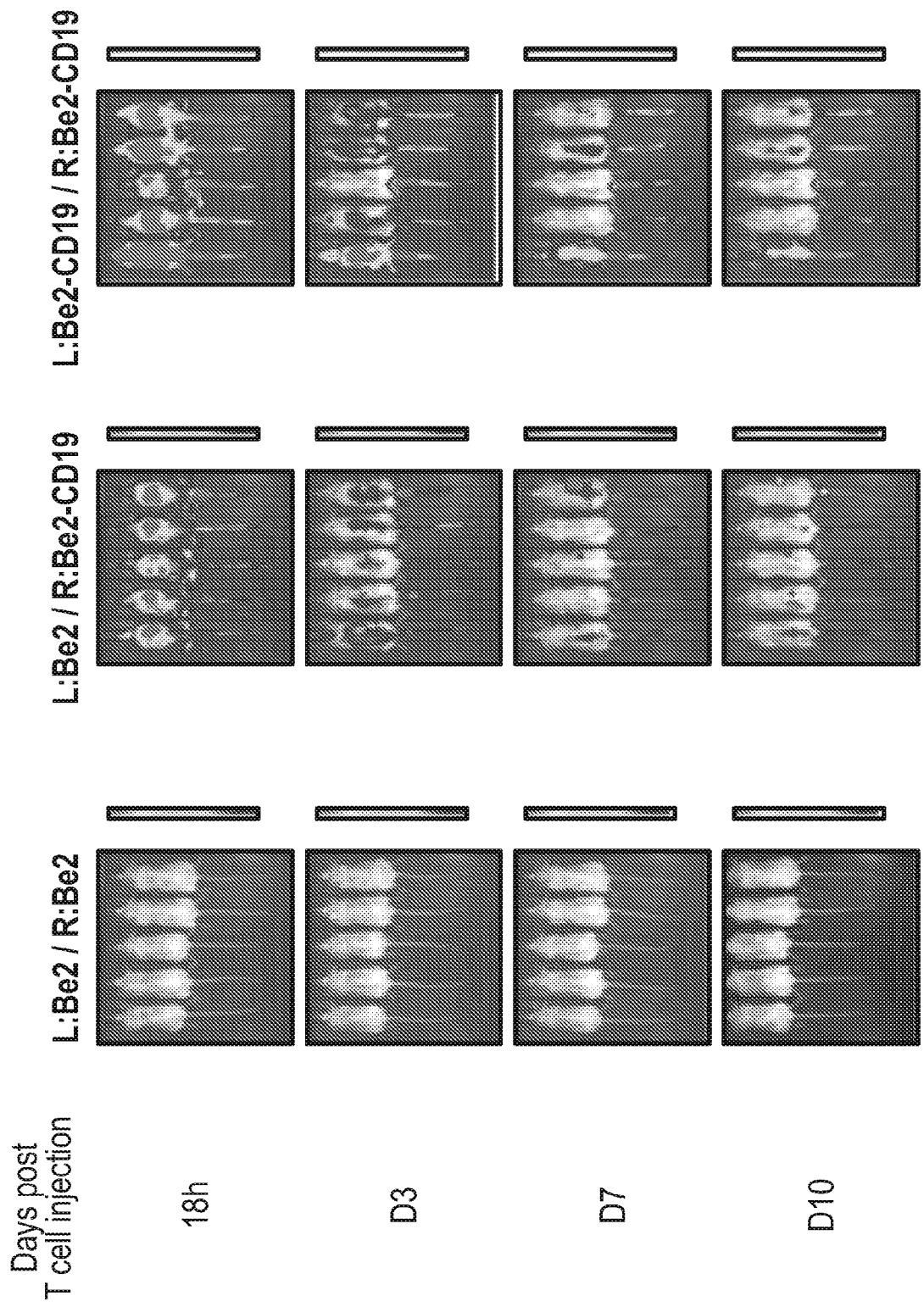
FIG. 21 shows the results of the above in vivo experiment. One day after T cell injection, a strong luciferase signal was seen on in group B mice which were engrafted with both Be2 and Be2/CD19 cells. An even stronger signal was seen in group C mice that were engrafted with Be2/CD19 cells on both flanks. Almost no signal was observed in group A mice which were engrafted with Be2 cells alone. It suggested that the luciferase signal was specific to CD19 antigen and presumably caused by CD19CAR activation as seen in in vitro before. The T cells were not localized in the flank region and instead, spread to all over the body especially the lung area indicating one day after encountering tumor cells CAR T cells were not retained in the tumor area. Three days after T cell injection, one mouse from group B showed tumor localized luciferase signal (right flank only). About seven days after T cell injection, the same phenomenon was seen in another mouse from group B. The localized luciferase signal went up and down over time in the first mouse and seemed to have the same trend in the second one. The luciferase seemed to correlate with the tumor volumes. The above two mice happened to have the highest tumor volumes among all five group B mice when the localized T cell luciferase signal reached high (data not shown). This was the first pilot experiment and more experiments need to be done to before any conclusion is drawn.
Figures 2, 21:
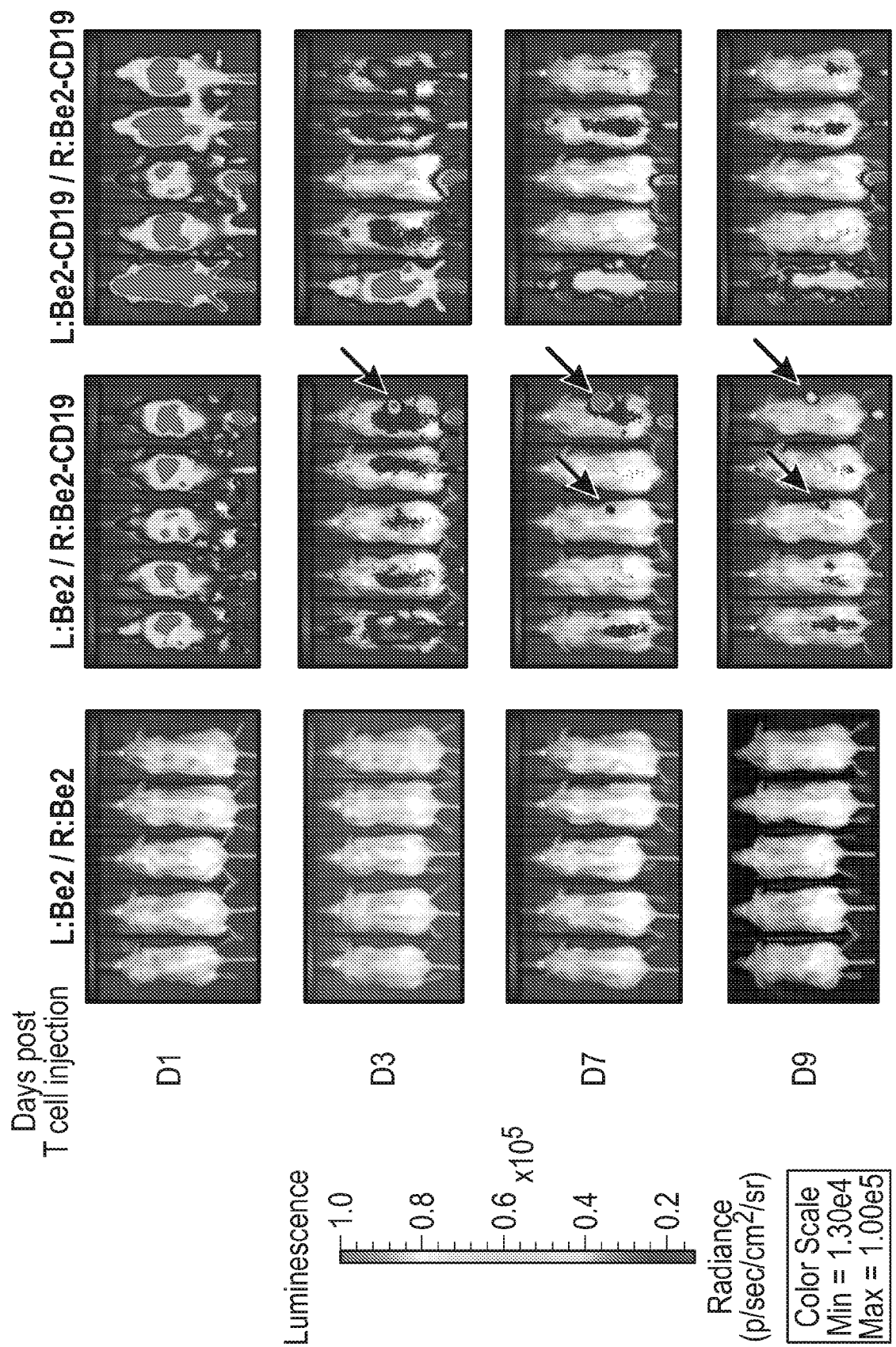
Figure 22:
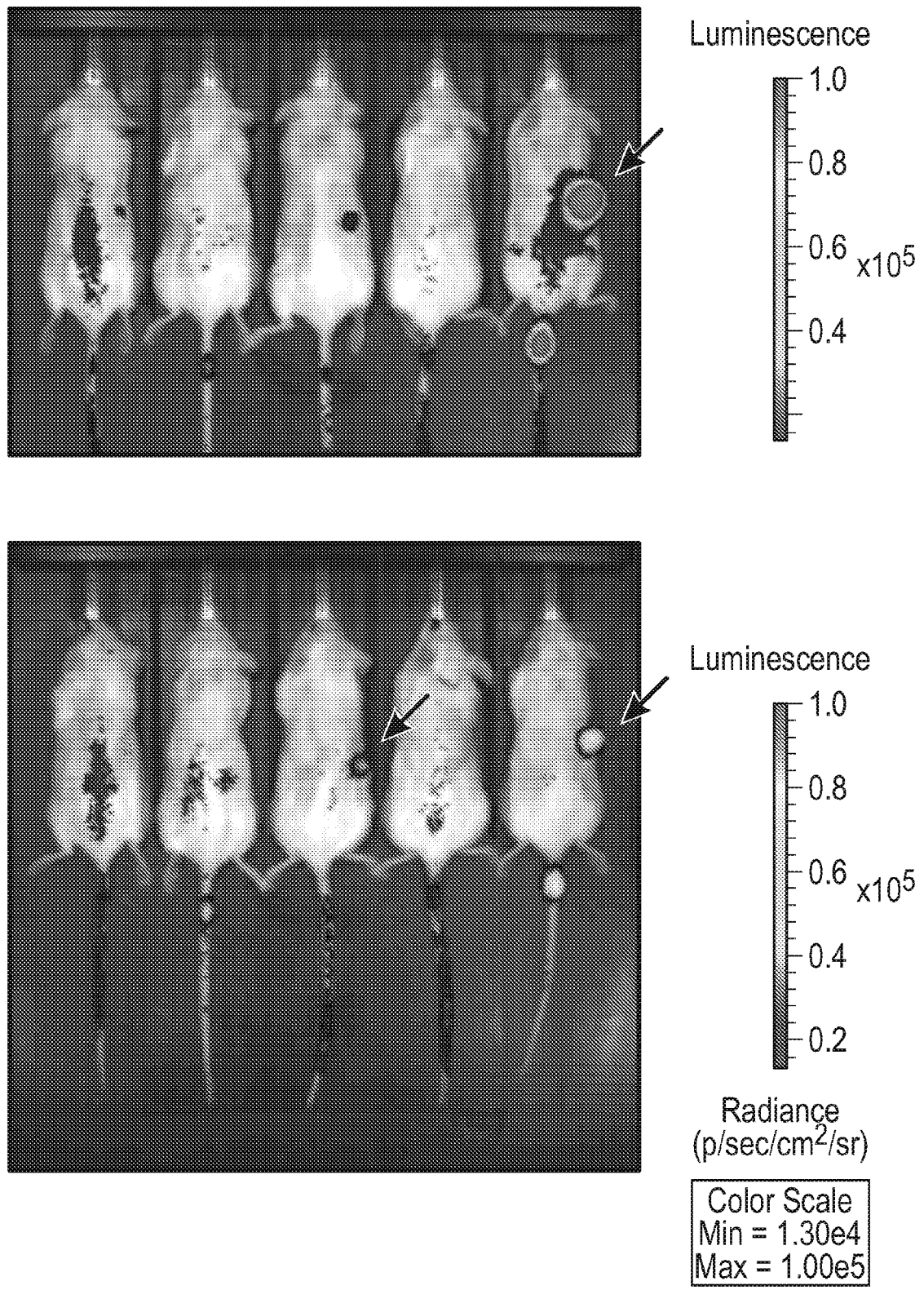
FIG. 22 shows the results of injecting CD8/CD19CAR/S1-61-GFP: ffluc EGFRt sorted cells into mice.

A pilot iSynPro in vivo study was then performed using the Be2/CD19 subcutaneous model. As shown in FIG. 20, the Be2 cells were subcutaneously injected into the mouse tail. At day 5, CD8 T cells were then injected into the cell. Images of the mice was then taken at days 6, 7, 8, 9, and 12 (FIGS. 21 and 22).

Figure 28:
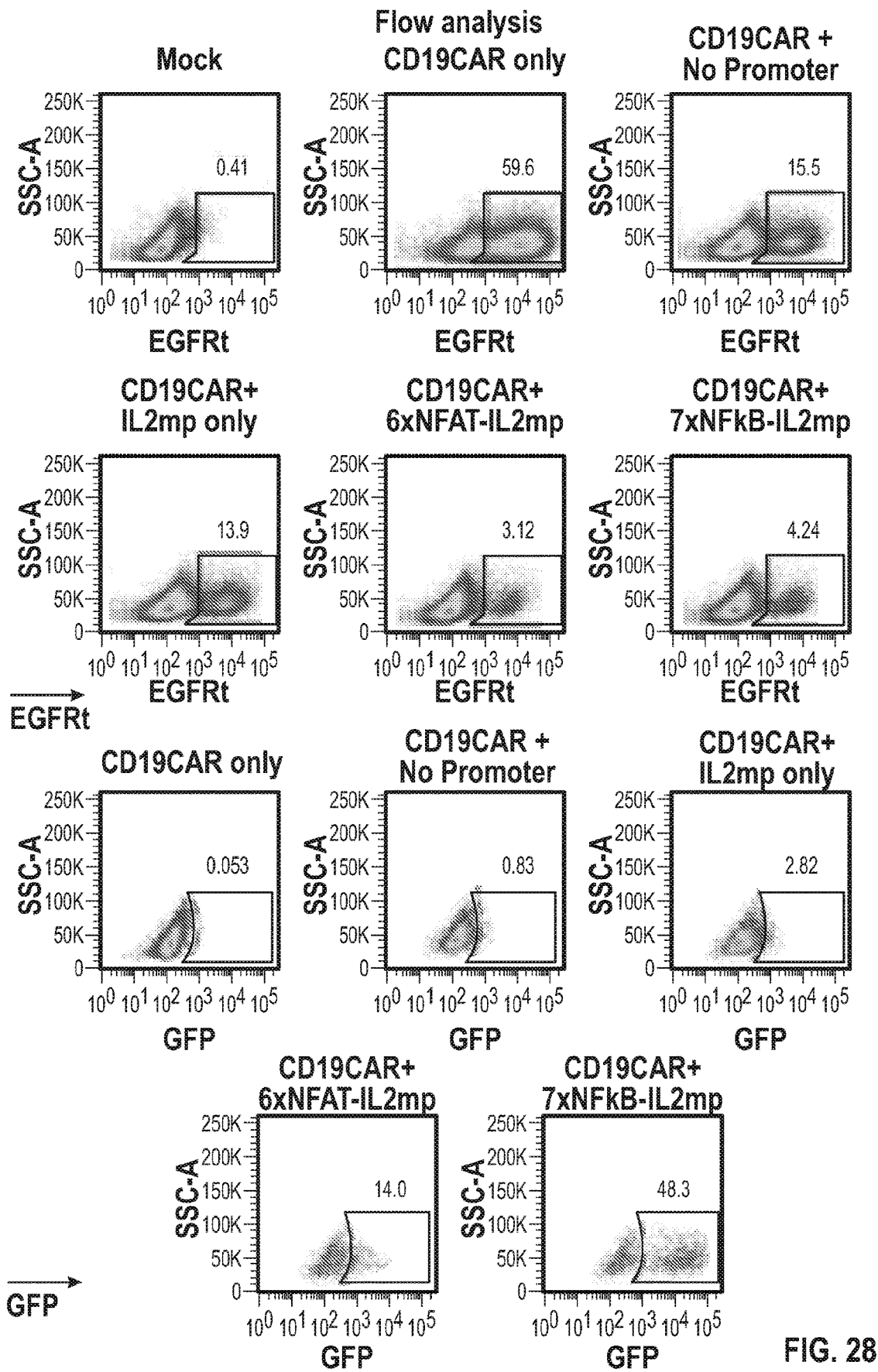
FIG. 28 is a display of flow analysis of mock cells, cells expressing CD19CAR, CD19+ CAR (no promoter), CD19CAR+ with IL2mp, CD19CAR+ with 6Xnfar-il2MP and CD19CAR+ 7×NFkB-IL2mp. EGFRt and GFP were measured in all cells. As shown, there was less expression of EGFRt and GFP with the 6×NFAR-IL2mp promoter.
Figure 29:
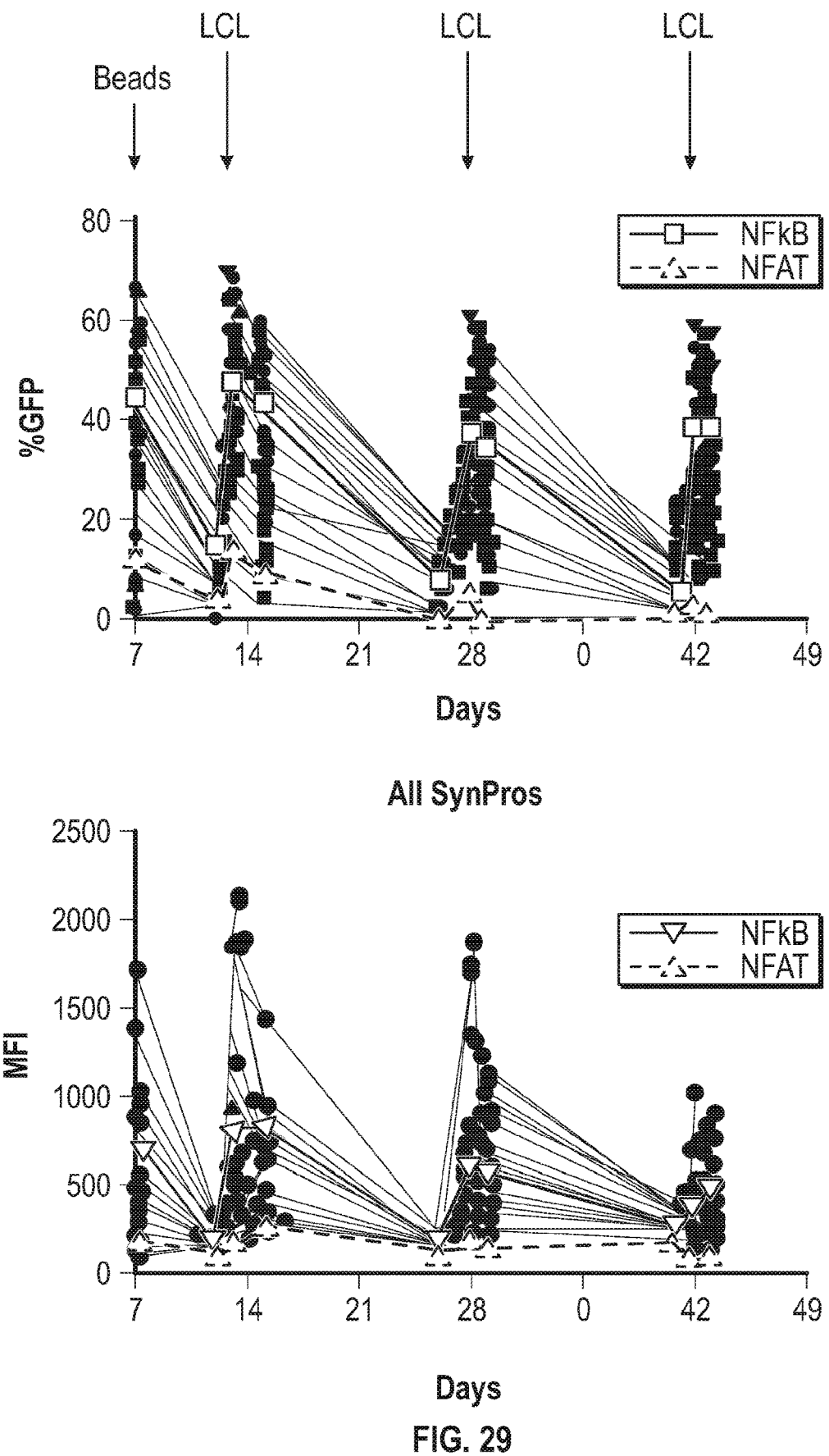
FIG. 29 shows two graphs that indicate that there are no unique expression patterns but the expression of the proteins were re-inducible.
Figure 30:
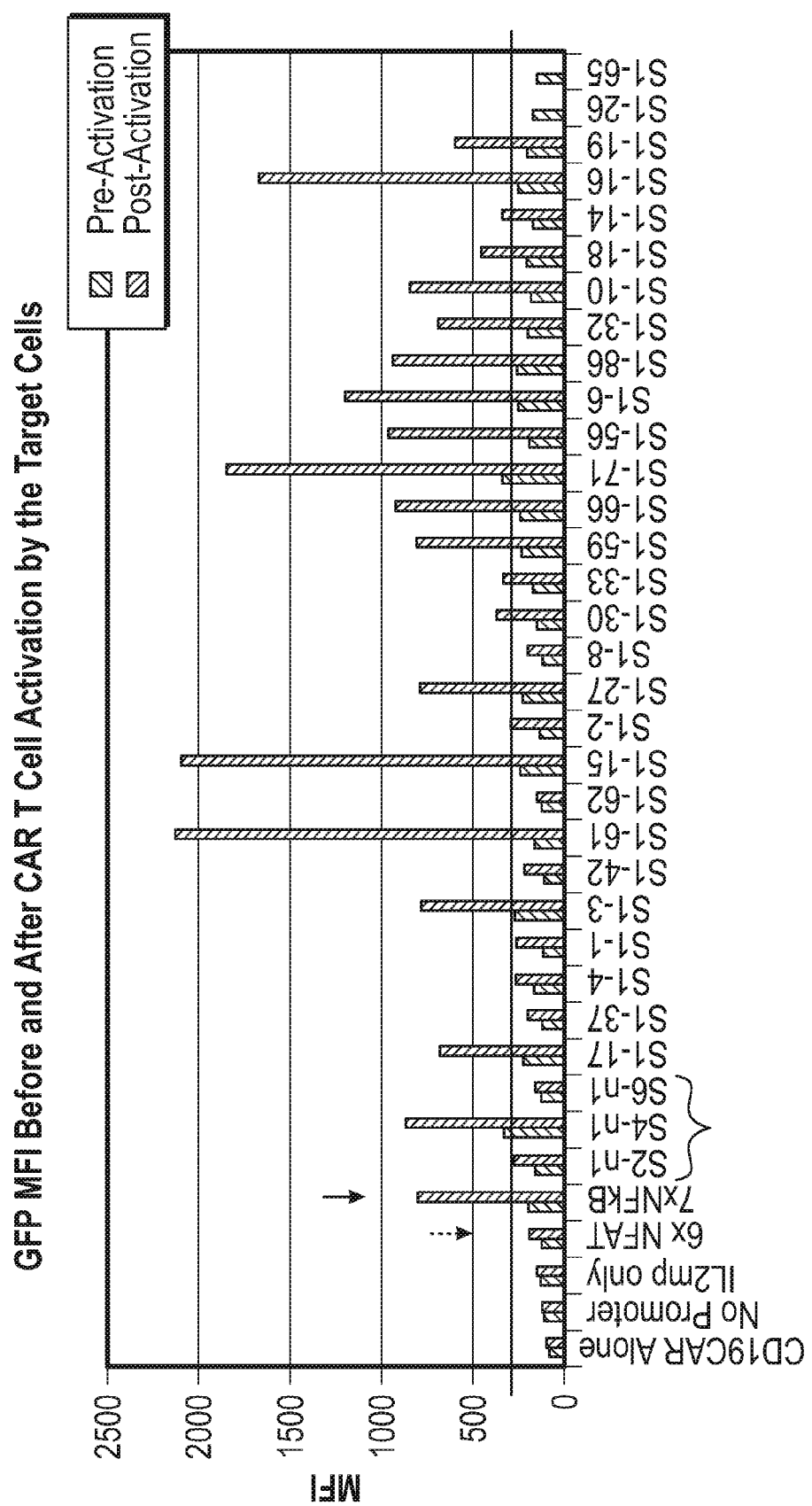
FIG. 30 shows the GFP MFI before and after CAR T cell activation by the target cells. From left to right consecutively are the pre-activation state and the post-activation state.
Figure 31:
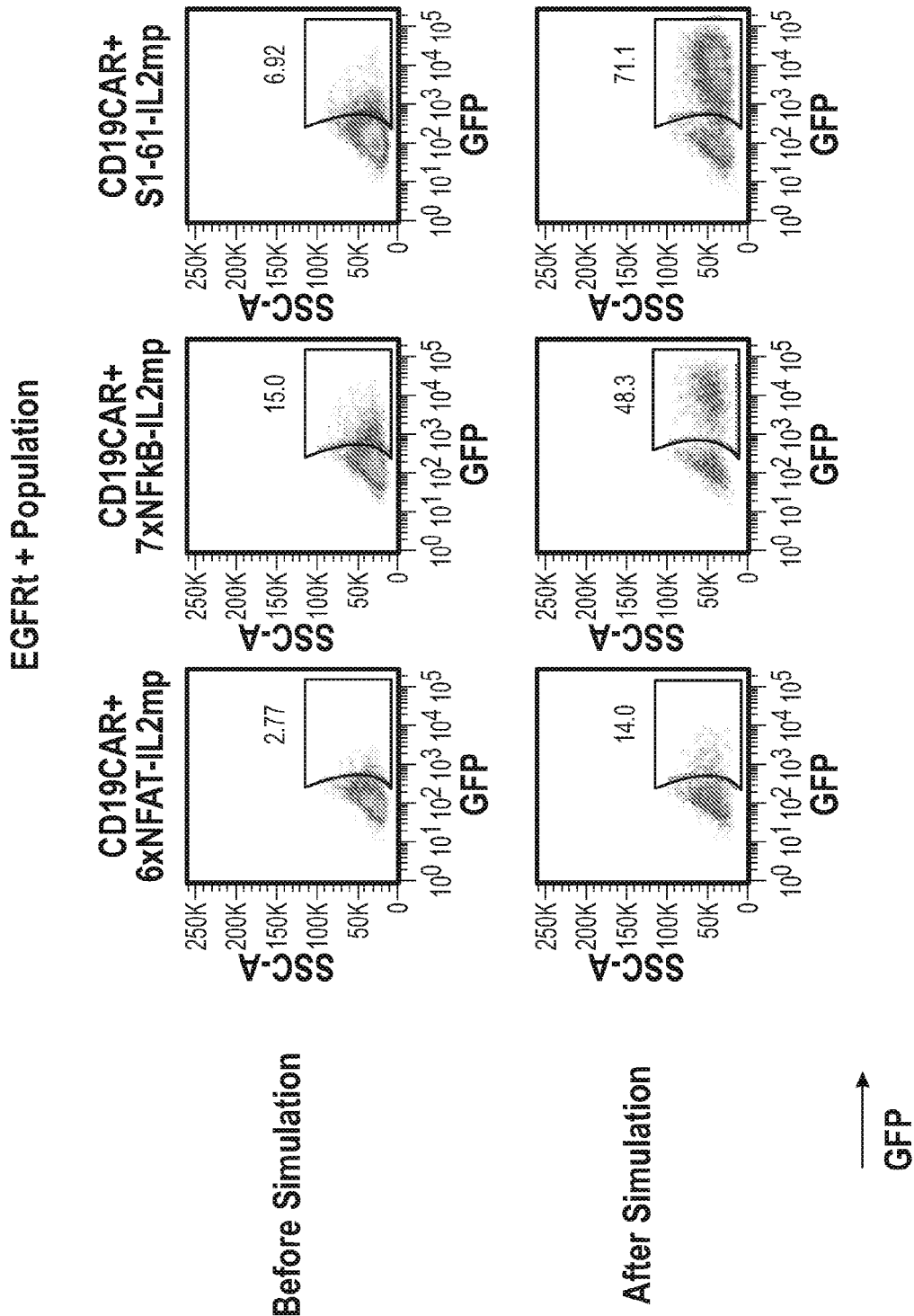
FIG. 31 shows the EGFRt+ population as shown in a series of FACS assays. Shown in the top row are the cells before stimulation and in the bottom row are the cells after stimulation (CD19CAR+6×NFAT-IL2mp, CD19CAR+7×NFkB and CD19CAR+S1-61-IL2mp). As shown, the cells with the promoter 7×NFkB and S1-61-IL2mp led to expression of EGFRt after stimulation.
Figures 1, 32:
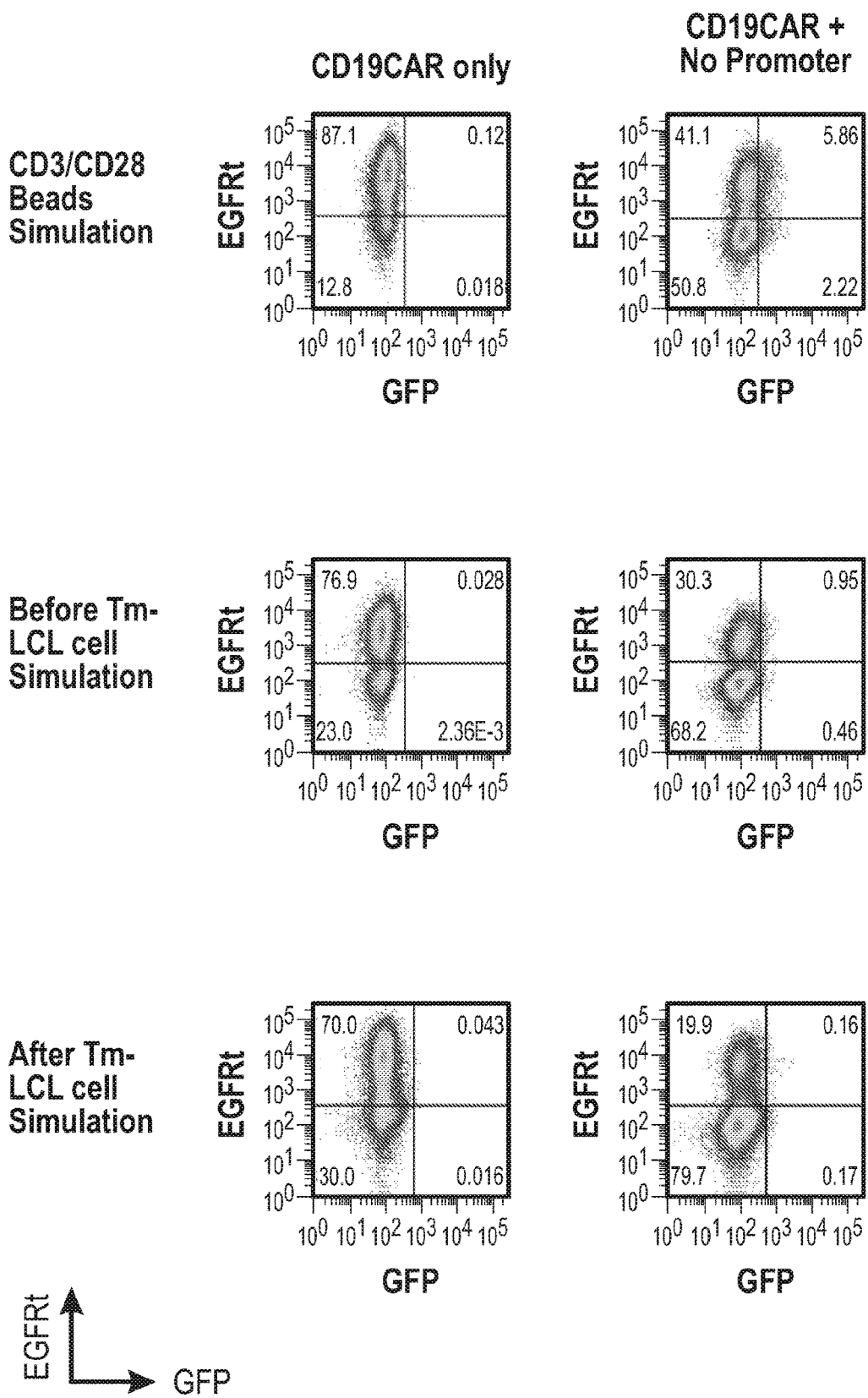
FIG. 32 shows expression of EGFRt and GFP in cells after CD3/CD28 simulation, and LCL cell stimulation. Cells used were CD19CAR only, CD19CAR+no promoter, CD19CAR+IL2mp only, CD19CAR+6×NFAT-IL2mp, and CD19CAR+S1-61-IL2mp. As shown, after stimulation the cells with the S1-61-IL2mp expressed the most of EGFRt and GFP.
Figures 2, 32:
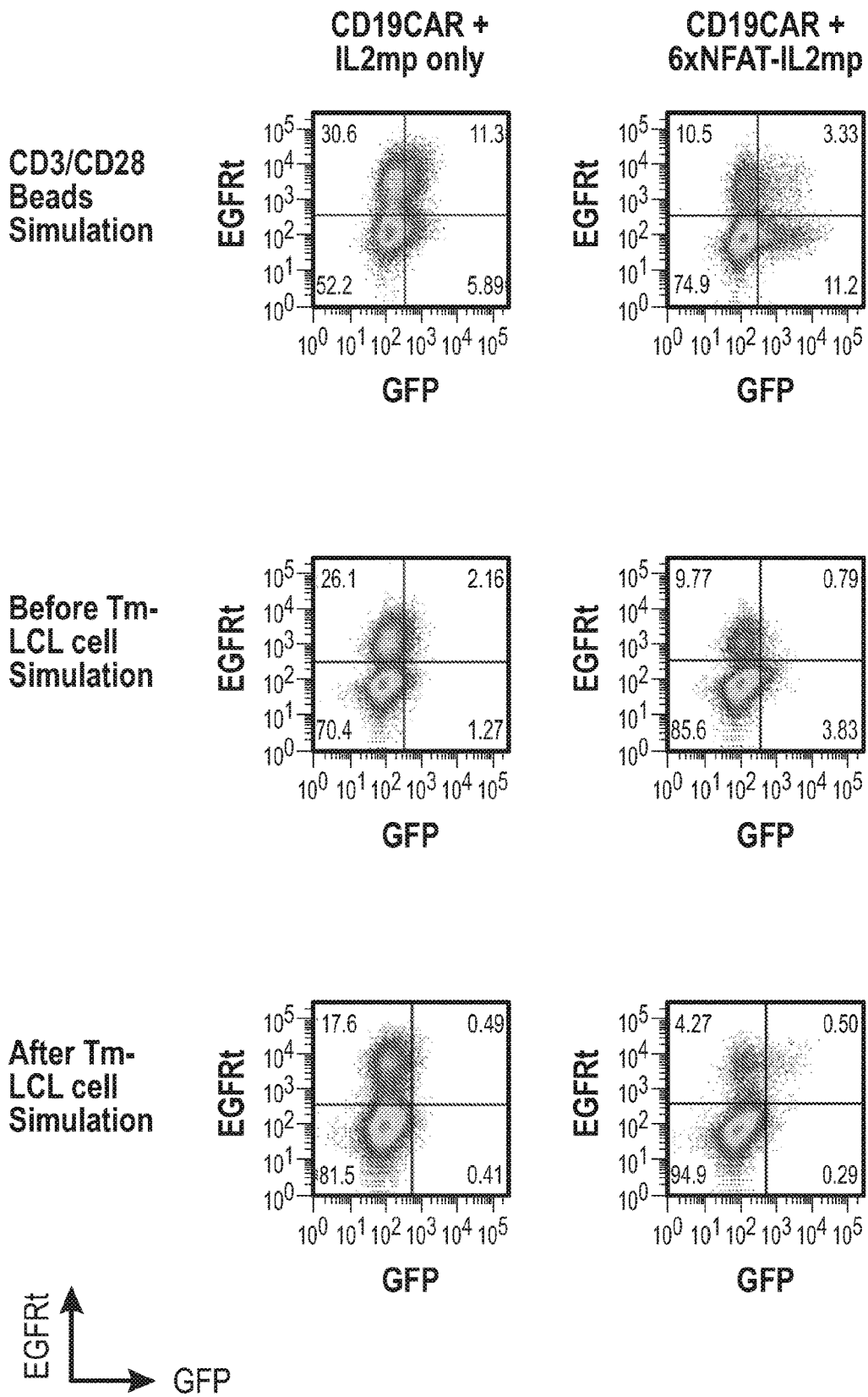
Figures 3, 32:
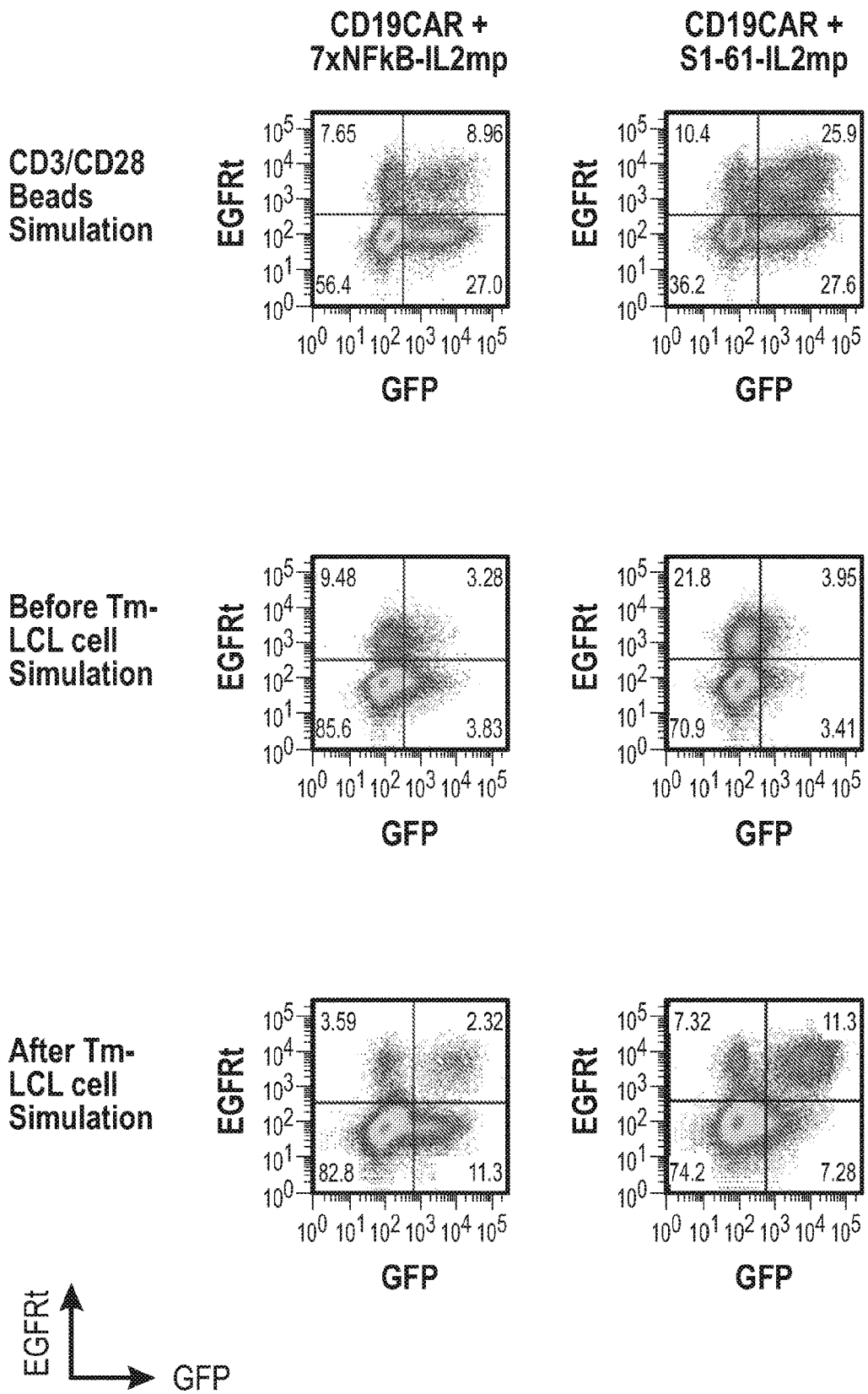

Syn-iPro testing in CD8 CAR T cells was also performed in cells co-transfected with vectors: a) Syn-Pro-IL2mp-GFP and b) EF1a-CD19scFv-EGFRt (FIG. 27). The cells were first stimulated with CD3/CD28 beads prior to virus transfection. The cells were then co-cultured with irradiated Tm-LCL cells at days 12, 13, 15, 26, 27, 28, 29, 41, 42 and 43. A FACS assay was then performed on the cells. As shown in FIG. 28, the cells were stimulated with CD19CAR bearing cells. As shown in FIG. 28, cells that were stimulated with CD19 CAR only expressed the most EGFRt. Cells carrying the Syn iPro synthetic promoter S1-61-IL2mp, expressed the most GFP after stimulation (FIG. 31).

Alternative 2

Next generation sequencing (NGS) of the DNA from sorted GFP+ cells yield over 200,000 unique promoter reads. ~30 unique promoter reads were chosen from the top ranking sequences (reads based ranking) to test in CAR T cells and majority of them were inducible and worked better than 6×NFAT promoter. It is anticipated there are more functional sequences in the untested sequence pool.

Technical limitations and biases exist through the promoter screening process, which decreases the diversity of the library over each step. For example, the library sample size dropped down by cloning the random ligation library to GFP:ffluc_HIV 7 plasmid and further from packaging the plasmid into lentivirus or taking the DNA extracted from the sorted cells for PCR amplification. On the other hand, the sequence redundancy was created over the steps where amplification happened, e.g. GFP:ffluc_HIV 7 plasmid transformed E. coli cells, lentivirus assembly in 293t cells, and PCR for targeted sequencing. Only after sequencing the libraries from each step (raw ligation, plasmid, and virus) will we be able to know the bias and therefore filter it out from the sorted cell sequencing result. In this way the ranking of the sorted cells will be more meaningful. Unfortunately we have not finished sequencing of all the libraries yet. However, it has been known that PCR favors short sequences and long sequences usually do not get as efficient amplification as the short ones. The two rounds of PCR amplification could potentially decreased the reads-based ranking of the long species. So among the untested sequences from the NGS Miseq run of the sorted cells, only choose long promoter sequences can be chosen (Similar to or longer than S-61, the best promoter so far) to patent simply because they were not favorable species of PCR amplification. Among the long sequences we further chose the sequences that showed in at least 3 or 4 time points. Here the number of reads threshold cut off is 100 (SEQ ID NO: 34-39).

In some alternatives, a method of making an inducible synthetic promoter library is provided, the method comprising: sequencing of DNA from cells comprising a marker gene; screening of putative promoters, screening transcription factor response elements, thereby producing screened transcription factor response elements; making an inducible synthetic promoter library comprising the putative promoters and synthesizing oligonucleotides, wherein the oligonucleotides comprise a first sequence encoding a screened transcription factor response element and a second sequence encoding the promoter. In some alternatives, the method is performed by Next generation sequencing. In some alternatives, the promoters are tested in CAR T cells for activation by CAR binding and CAR T signaling. In some alternatives, the screening comprises assaying for transcription or translation of a marker gene. In some alternatives, a promoter is sequenced following upregulation of a marker gene and is tested for activation in response to a CAR-T cell interaction with a ligand. In some alternatives, the CAR-T cell interaction drives upregulation of transcription factor response elements.

SEQUENCES

SEQUENCES OF THE Syn-iPro
Name Sequence
SEQ ID NO: 1
S1-17
CTGCTTAGGGTTAGGCGTTTTGCGCTGCTTCGCGATCGAGGAGGAAAAAC
TCGATGTGACTCATTCGAAGATCAAAGGGTCGAGGAAAGTCCCCTCGACC
CTTTGATCTTCGAATGACATCATCTTTCGAGGAAAGTCCCCTCGAGGGGA
CTTTCCTCGAGGGGACTTTCCTCGAATGAGTCACATCGATCTCCGCCCCC
TCTTCGAGCGCCAAATCGAGGACGTGATCGAGTAGAGTCTAGACTCTACA
TTTTGACACCCCCAT SEQ ID NO: 2
S1-37
CTGCTTAGGGTTAGGCGTTTTGCGCTGCTTCGCGATCGAGGGGCGGGGT
CGATCTCCGCCCCCTCTTCGAGTTTTTCCTCCTCGAGGGGACTTTCCTCG
AATGACATCATCTTTCGACCCTTTGATCTTCGAAGGAAGTTCGATCACGT
CCTCGATTTGGCGCTCGAGGGGACTTTCCTCGAAGATCAAAGGGTCGAGT
AGAGTCTAGACTCTACATTTTGACACCCCCAT SEQ ID NO: 3
S1-4
CTGCTTAGGGTTAGGCGTTTTGCGCTGCTTCGCGATCGATTTCCAAGAAA
TCGAGGAAAGTCCCCTCGACCCTTTGATCTTCGAGGAGGAAAAACTCGAA
TGAGTCACATCGACCCTTTGATCTTCGAAGAGGGGGCGGAGATCGATCTC
CGCCCCCTCTTCGAGGAAAGTCCCCTCGACCCTTTGATCTTCGACCCCGC
CCCCTCGAGGAAAGTCCCCTCGAGTAGAGTCTAGACTCTACATTTTGACA
CCCCCAT SEQ ID NO: 4
S1-1
CTGCTTAGGGTTAGGCGTTTTGCGCTGCTTCGCGATCGATCTCCGCCCCC
TCTTCGAAGATCAAAGGGTCGAGGGGACTTTCCTCGATTTCTTGGAAATC
GAATGACATCATCTTTCGATTTGGCGCTCGAATGACATCATCTTTCGACC
CTTTGATCTTCGATGTGACTCATTCGAGGGGACTTTCCTCGAAGATCAAA
GGGTCGAGGGGACTTTCCTCGAGTAGAGTCTAGACTCTACATTTTGACAC
CCCCAT SEQ ID NO: 5
S1-3
CTGCTTAGGGTTAGGCGTTTTGCGCTGCTTCGCGATCGAGGGGACTTTCC
TCGAGGGGGCGGGGTCGATTTGGCGCTCGATCTCCGCCCCCTCTTCGAAT
GAGTCACATCGAGGAAAGTCCCCTCGAGGAGGAAAAACTCGATGTGACTC
ATTCGATTTCCAAGAAATCGAGTAGAGTCTAGACTCTACATTTTGACACC
CCCAT SEQ ID NO: 6
S1-42
CTGCTTAGGGTTAGGCGTTTTGCGCTGCTTCGCGATCGATTTCCAAGAAA
TCGATCTCCGCCCCCTCTTCGAATGACATCATCTTTCGAATGACATCATC
TTTCGAGGAGGAAAAACTCGACCCCGCCCCCTCGATTTCTTGGAAATCGA
GGAAAGTCCCCTCGAGCGCCAAATCGAAGGAAGTTCGAATGACATCATCT
TTCGAATGAGTCACATCGAGGAAAGTCCCCTCGAGGAGGAAAAACTCGAG
TAGAGTCTAGACTCTACATTTTGACACCCCCAT SEQ ID NO: 7
S1-61
CTGCTTAGGGTTAGGCGTTTTGCGCTGCTTCGCGATCGAATGAGTCACAT
CGATCTCCGCCCCCTCTTCGAGGGGGCGGGGTCGAGGAGGAAAAACTCGA ATGAGTCACATCGACCCTTTGATCTTCGAGGGGACTTTCCGGGGTGGAGC
AAGCGTGACAAGTCCACGTATGACCCGACCGACGATATCGAAGCCTACGC
GCTGAACGCCAGCCCCGATCGACCCCGCCCCCTCGATTTCCAAGAAATCG
AATGACATCATCTTTCGAATGACATCATCTTTCGAGGGGACTTTCCTCGA
ACTTCCTTCGAGGGGACTTTCCTCGAGGGGACTTTCCTCGAGGAGGAAAA
ACTCGAGTAGAGTCTAGACTCTACATTTTGACACCCCCAT SEQ ID NO: 8
S1-62
CTGCTTAGGGTTAGGCGTTTTGCGCTGCTTCGCGATCGATTTCCAAGAAA
TCGAGTTTTTCCTCCTCGAGGGGGCGGGGTCGAGGGGACTTTCCTCGACC
CTTTGATCTTCGAGGAAAGTCCCCTCGAGCGCCAAATCGATCTCCGCCCC
CTCTTCGAGTAGAGTCTAGACTCTACATTTTGACACCCCCAT SEQ ID NO: 9
S1-15
CTGCTTAGGGTTAGGCGTTTTGCGCTGCTTCGCGATCGAAGATCAAAGGG
TCGATTTCTTGGAAATCGATGTGACTCATTCGATCACGTCCTCGAGGAGG
AAAAACTCGAGGAAAGTCCCCTCGAACTTCCTTCGAGGGGGCGGGGTCGA
ATGAGTCACATCGAGGAAAGTCCCCTCGAGGGGACTTTCCTCGATTTCTT
GGAAATCGAAGAGGGGGCGGAGATCGAGTTTTTCCTCCTCGAGGAAAGTC
CCCTCGATCGACTCTACATTTTGACACCCCCAT SEQ ID NO: 10
S1-2
CTGCTTAGGGTTAGGCGTTTTGCGCTGCTTCGCGATCGAATGAGTCACAT
CGAAGATCAAAGGGTCGACCCTTTGATCTTCGATTTGGCGCTCGATGTGA
CTCATTCGACCCCGCCCCCTCGAGGAAAGTCCCCTCGAGGAAAGTCCCCT
CGAGGAAAGTCCCCTCGAGGAAAGTCCCCTCGAGTTTTTCCTCCTCGAAG
AGGGGGCGGAGATCGATTTGGCGCTCGAGGACGTGATCGAGTAGAGTCTA
GACTCTACATTTTGACACCCCCAT SEQ ID NO: 11
S1-27
CTGCTTAGGGTTAGGCGTTTTGCGCTGCTTCGCGATCGATTTCCAAGAAA
TCGAGTTTTTCCTCCTCGATTTCCAAGAAATCGAGGGGACTTTCCTCGAG
GGGACTTTCCTCGAATGACATCATCTTTCGATGTGACTCATTCGAAGATC
AAAGGGTCGAAGGAAGTTCGAATGAGTCACATCGAATGAGTCACATCGAC
CCTTGATCTTCGAGGAGGAAAAACTCGATTTGGCGCTCGATTTGGCGCTC
GAGTAGAGTCTAGACTCTACATTTTGACACCCCCAT SEQ ID NO: 12
S1-8
CTGCTTAGGGTTAGGCGTTTTGCGCTGCTTCGCGATCGATTTCTTGGAAA
TCGATTTGGCGCTCGAAGGAAGTTCGAGGGGCGGGGTCGATTTCCAAGA
AATCGAGTTTTTCCTCCTCGAGCGCCAAATCGACCCTTTGATCTTCGATC
ACGTCCTCGAGCGCCAAATCGAGGACGTGATCGAATGAGTCACATCGAAT
GAGTCACATCGAATGAGTCACATCGATTTGGCGCTCGATCGGGGGCGGG
GTCGAGGAAAGTCCCCTCGAGGAAAGTCCCCTCGATTTCCAAGAAATCGA
TTTGGCGCTCGATCTCCGCCCCCTCTTCGATCTCCGCCCCCTCTTCGAGT
TTTTCCTCCTCGAGTAGAGTCTAGACTCTACATTTTGACACCCCCAT SEQ ID NO: 13
S1-30
CTGCTTAGGGTTAGGCGTTTTGCGCTGCTTCGCGATCGAATGACATCATC
TTTCGAGGAAAGTCCCCTCGACCCTTTGATCTTCGACCCCGCCCCCTCGA
GTTTTTCCTCCTCGAGGAAAGTCCCCTCGACCCTTTGATCTTCGAGGGGA
CTTTCCTCGAGGGGCGGGGTCGAGGACGTGATCGAGGAAAGTCCCCTCG
AGTAGAGTCTAGACTCTACATTTTGACACCCCCAT SEQ ID NO: 14
S1-33
CTGCTTAGGGTTAGGCGTTTTGCGCTGCTTCGCGATCGAAGATCAAAGGG
TCGAGGAGGAAAAACTCGAGGGGACTTTCCTCGACCCTTTGATCTTCGAA
TGAGTCACATCGATTCTTGGAAATCGAAGGAAGTTCGAGGGGACTTTCC
TCGAGTTTTTCCTCCTCGAACTTCCTTCGAGGAAAGTCCCCTCGAAGTTT
AAAGGGTCGAAGGAAGTTCGAAAGATGATGTCATTCGATTCTTGGAAAT
CGAAGATCAAAGGGTCGAAGAGGGGCGGAGATCGATTTCCAAGAAATCG
AGTAGAGTCTAGACTCTACATTTTGACACCCCCAT SEQ ID NO: 15
S1-41
CTGCTTAGGGTTAGGCGTTTTGCGCTGCTTCGCGATCGAATGAGTCACAT
CGAGCGCCAAATCGAGGGGACTTTCCTCGAGGGGGCGGGGTCGATTTTT
CCTCCTCGATTTCCAAGAAATCGAGGGGACTTTCCTCGAGGGGACTTTCC
TCGAGGGGACTTTCCTCGAGTAGAGTCTAGACTCTACATTTTGACACCCC
CAT SEQ ID NO: 16
S1-59
CTGCTTAGGGTTAGGCGTTTTGCGCTGCTTCGCGATCGAGTTTTTCCTCC
TCGAGGGGACTTTCCTCGAAAGATGATGTCATTCGATCTCCGCCCCCTCT
TCGAGGGGACTTTCCTCGAGGAAAGTCCCCTCGAGGAAAGTCCCCTCGAA
GATCAAAGGGTCGAATGAGTCACATCGACCCTTTGATCTTCGACCCTTTG
ATCTTCGATTTCCAAGAAATCGAGGAAAGTCCCCTCGAGGAAAGTCCCCT
CGAGTAGAGTCTAGACTCTACATTTTGACACCCCCAT SEQ ID NO: 17
S1-66
CTGCTTAGGGTTAGGCGTTTTGCGCTGCTTCGCGATCGAGGGGACTTTCC
TCGAGGAAAGTCCCCTCGATTTCTTGGAAATCGATTTGGCGCTCGAGGAG
GAAAAACTCGATGTGACTCATTCGACCCTTTGATCTTCGAGGGGACTTTC
CTCGAGGGGACTTTCCTCGAGCGCCAAATCGAGGAGGAAAAACTCGAGGG
GACTTTCCTCGATTTCTTGGAAATCGAAAGATGATGTCATTCGACCCTTT
GATCTTCGAGTAGAGTCTAGACTCTACATTTTGACACCCCCAT SEQ ID NO: 18
S1-71
CTGCTTAGGGTTAGGCGTTTTGCGCTGCTTCGCGATCGAGGAAAGTCCCC
TCGAGGAAAGTCCCCTCGATTTCTTGGAAATCGAATGACATCATCTTTCG
ATCACGTCCTCGAGGAAAGTCCCCTCGAGTTTTTCCTCCTCGAGGGGACT
TTCCTCGATTTCCAAGAAATCGATTTCTTGGAAATCGACCCTTTGATCTT
CGAGGAGGAAAAACTCGAGTAGAGTCTAGACTCTACATTTTGACACCCCC
AT SEQ ID NO: 19
S1-56
CTGCTTAGGGTTAGGCGTTTTGCGCTGCTTCGCGATCGATGTGACTCATT
CGAAGATCAAAGGGTCCCCTCGATTTGGCGCTCGATGTGACTCATTCGGC
GCTCGAGGGGACTTTCCTCGATTTCCAAGAAATCGAGGGGACTTTCCTCG
AGGAAAGTCCCCTCGAGTTTTTCCTCCTCGAGTAGAGTCTAGACTCTACA
TTTTGACACCCCCAT SEQ ID NO: 20
S1-6
CTGCTTAGGGTTAGGCGTTTTGCGCTGCTTCGCGATCGATGTGACTCATT
CGAGCGCCAAATCGATTTCCAAGAAATCGAATGAGTCACATCGAATGACA
TCATCTTTCGATGTGACTCATTCGAGGAAAGTCCCCTCGATTTCTTGGAA
ATCGAGGAAAGTCCCCTCGAGTTTTTCCTCCTCGAAGAGGGGCGGAGAT
CGAATGACATCATCTTTCGAGTAGAGTCTAGACTCTACATTTTGACACCC
CCAT SEQ ID NO: 21
S1-60
CTGCTTAGGGTTAGGCGTTTTGCGCTGCTTCGCGATCGAGGGGACTTTCC
TCGATCTCCGCCCCCTCTTCGAGGAAAGTCCCCTCGAAGGAAGTCGAAC
TTCCTTCGAGGGGACTTTCCTCGAAGGAAGTTCGAGCGCCAAATCGAATG
AGTCACATCGATTTCCAAGAAATCGATCTCCGCCCCCTCTTCGAGGAGGA
AAAACTCGAGGGGACTTTCCTCGATTTCCAAGAAATCGAGGGGACTTTCC
TCGATCACGTCCTCGAGGACGTGATCGAATGAGTCACATCGATGTGACTC
ATTCGACCCTTTGATCTTCGAGTAGAGTCTAGACTCTACATTTTGACACC
CCCAT SEQ ID NO: 22
S1-86
CTGCTTAGGGTTAGGCGTTTTGCGCTGCTTCGCGATCGATTTCCAAGAAA
TCGAGGGGCGGGGTCGAGGGACTTTCCTCGAGGGGACTTTCCTCGAGG
AAAGTCCCCTCGATCTCCGCCCCCTCTTCGAGGAAAGTCCCCTCGAACTT
CCTTCGAGGAAAGTCCCCTCGAATGAGTCACATCGATTTGGCGCTCGAGG
AAAGTCCCCTCGAGGGGACTTTCCTCGAGGAAAGTCCCCTCGAGGGGGCG
GGGTCGAACTTCCTTCGAGTAGAGTCTAGACTCTACATTTTGACACCCCC
AT SEQ ID NO: 23
S1-32
CTGCTTAGGGTTAGGCGTTTTGCGCTGCTTCGCGATCGAATGAGTCACAT
CGATCTCCGCCCCCTCTTCGATTTGGCGCTCGAGGGGACTTTCCTCGACC
CTTTGATCTTCGAGGGGACTTTCCTCGAGGAAAGTCCCCTCGAGGAAAGT
CCCCTCGAGTAGAGTCTAGACTCTACATTTTGACACCCCCAT SEQ ID NO: 24
S1-10
CTGCTTAGGGTTAGGCGTTTTGCGCTGCTTCGCGATCGATTTGGCGCTCG
ATGTGACTCATTCGAGGAAAGTCCCCTCGAGGGGACTTTCCTCGAAGATC

| SEQUENCES |
|---|
| AAAGGGTCGAAAGATGATGTCATTCGAGGAAAGTCCCCTCGACCCCGCCC<br>CCTCGATTTCTTGGAAATCGAATGAGTCACATCGATTTCTTGGAAATCGA<br>TGTGACTCATTCGAGTAGAGTCTAGACTCTACATTTTGACACCCCCAT<br><br>SEQ ID NO: 25<br>S1-18<br>CTGCTTAGGGTTAGGCGTTTTGCGCTGCTTCGCGATCGAGGGGACTTTCC<br>TCGATGTGACTCATTCGATTTCTTGGAAATCGATTTCCAAGAAATCGACC<br>CCGCCCCTCGAGGAGGAAAAACTCGATTTCCAAGAAATCGAATGACATC<br>ATCTTTCGAGGGGACTTTCCTCGAAGATCAAAGGGTCGAAGATCAAAGGG<br>TCGAGGAGGAAAAACTCGATTTCCAAGAAATCGAATGAGTCACATCGAGT<br>TTTTCCTCCTCGATTTCTTGGAAATCGAAGAGGGGGCGGAGATCGATTTG<br>GCGCTCGAGTAGAGTCTAGACTCTACATTTTGACACCCCCAT<br><br>SEQ ID NO: 26<br>S1-14<br>CTGCTTAGGGTTAGGCGTTTTGCGCTGCTTCGCGATCGAAAGATGATGTC<br>ATTCGAATGAGTCACATCGATTTGGCGCTCGAGGGGGCGGGGTCGATTTG<br>GCGCTCGAAAGATGATGTCATTCGAGTTTTTCCTCCTCGACCCTTTGATC<br>TTCGAAGAGGGGGCGGAGATCGAAAGATGATGTCATTCGAATGAGTCACA<br>TCGATTTCCAAGAAATCGATTTCCAAGAAATCGAGTAGAGTCTAGACTCT<br>ACATTTTGACACCCCCAT<br><br>SEQ ID NO: 27<br>S1-16<br>CTGCTTAGGGTTAGGCGTTTTGCGCTGCTTCGCGATCGAGGAGGAAAAAC<br>TCGATTTCTTGGAAATCGAGGGGACTTTCCTCGAAAGATGATGTCATTCG<br>AAGATCAAAGGGTCGATGTGACTCATTCGAGGGGACTTTCCTCGAGGGGG<br>CGGGGTCGAATGACATCATCTTTCGAGGGGACTTTCCTCGAGGGGACTTT<br>CCTCGAATGACATCATCTTTCGATTTCTTGGAAATCGAGTAGAGTCTAGA<br>CTCTACATTTTGACACCCCCAT<br><br>SEQ ID NO: 28<br>S1-19<br>CTGCTTAGGGTTAGGCGTTTTGCGCTGCTTCGCGATCGATCTCCGCCCCC<br>TCTTCGAGTTTTTCCTCCTCGATTTCTTGGAAATCGAAGATCAAAGGGTC<br>GATTTCTTGGAAATCGAGGGGACTTTCCTCGAGGAAAGTCCCCTCGAGGG<br>GACTTTCCTCGAGGAGGAAAAACTCGATTTGGCGCTCGAGTAGAGTCTAG<br>ACTCTACATTTTGACACCCCCAT<br><br>SEQ ID NO: 29<br>S1-26<br>CTGCTTAGGGTTAGGCGTTTTGCGCTGCTTCGCGATCGAAAGATGATGTC<br>ATTCGAGTTTTTCCTCCTCGAAGGAAGTTCGAGGACGTGATCGAAGAGGG<br>GGCGGAGATCGAATGAGTCACATCGAAGGAAGTTCGAGGAAAGTCCCCTC<br>GAGGAAAGTCCCCTCGAAGATCAAAGGGTCGAGTAGAGTCTAGACTCTAC<br>ATTTTGACACCCCCAT<br><br>SEQ ID NO: 30<br>S1-65<br>CTGCTTAGGGTTAGGCGTTTTGCGCTGCTTCGCGATCGACCCCGCCCCT<br>CGAGCGCCAAATCGAGGGGACTTTCCTCGAGGGGACTTTCCTCGAGGGGA<br>CTTTCCTCGAGTAGAGTCTAGACTCTACATTTTGACACCCCCAT<br><br>SEQ ID NO: 31<br>S2-n1<br>CTGCTTAGGGTTAGGCGTTTTGCGCTGCTTCGCGATCGAGGGGCGGGGT<br>CGAATGACATCATCTTTCGAGGAAAGTCCCCTCGAGGAAAGTCCCCTCGA<br>GGAAAGTCCCCTCGATTTCCAAGAAATCGACCCTTTGATCTTCGAAGATC<br>AAAGGGTCGATGTGACTCATTCGAAGATCAAAGGGTCGATTTGGCGCTCG<br>AGTAGAGTCTAGACTCTACATTTTGACACCCCCAT<br><br>SEQ ID NO: 32<br>S4-n1<br>CTGCTTAGGGTTAGGCGTTTTGCGCTGCTTCGCGATCGAGGAAAGTCCCC<br>TCGAGTTTTTCCTCCTCGAAGGGGGCGGAGATCGATTTCCAAAAAACT<br>CGAATGACATCATCTTTCGAAGATCAAGGGGTCGAAGATCAAAGGGTCGA<br>TTTCCAAGAAATCGATTTCTTGGAAATCGAGGAAAGTCCCCTCGACCCTT<br>TGATCTTCGATCTCCGCCCCTCTTCGAAGATCAAAGGGTCGAAGAGGGG<br>GCGGAGATCGAGTAGAGTCTAGACTCTACATTTTGACACCCCCAT<br><br>SEQ ID NO: 33<br>S6-n1<br>CTGCTTAGGGTTAGGCGTTTTGCGCTGCTTCGCGATCGATTTCCAAGAAA<br>TCGATTTCTTGGAAATCGAATGACATCATCTTTCGAGTTTTTCCTCCTCG<br>AAGAGGGGGCGGAGATCGAGGAAAGTCCCCTCGATTTCCAAGAAATCGAA<br>CTTCCTTCGAAGGAAGTTCGAGGAGGAAAAACTCGAGGGGCGGGGTCGA |

| SEQUENCES |
|---|
| GTTTTTCCTCCTCGAGGGGACTTTCCTCGACCCCGCCCCCTCGACCCTTT<br>GATCTTCGATTTCCAAGAAATCGAGTAGAGTCTAGACTCTACATTTTGAC<br>ACCCCCAT<br><br>SEQ ID NO: 34<br>S1-325<br>TCGAAGATCAAAGGGTCGATTTCCAAGAAATCGATGTGACTCATTCGATT<br>TGGCGCTCGACCCCGCCCCCTCGAAGAGGGGGCGGAGATCGAATGAGTCA<br>CATCGAGGAAAGTCCCCTCGATTTCTTGGAAATCGAGGAAAGTCCCCTCG<br>AGGGGACTTTCCTCGAGGAGGAAAAACTCGAATGACATCATCGAAT<br>GAGTCACATCGATTTCTTGGAAATCGAGGGGACTTTCCTCGACCCCGCCC<br>CCTCGAGGTGACTTTCCTCGAGGGGACTTTCCTCGATGTGACTCATTCGA<br>GGGGACTTTCCTCGAGGGGACTTTCCTCGACCCTTTGATCTTCGATTTGG<br>CGCTCGAGGGGACTTTCCTCGAGGGGACTTTCCTCGAGGGGACTTTCCTC<br>GAGTAGAGTCTAGACTCTACATTTTGACACCCCCA<br><br>SEQ ID NO: 35<br>S1-60<br>TCGAATGAGTCACATCGATCTCCGCCCCCTCTTCGAGGGGGCGGGGTCGA<br>GGAGGAAAAACTCGAATGAGTCACATCGACCCTTTGATCTTCGAGGGGAC<br>TTTCCGGGGTGGAGCAAGCGTGACAAGTCCACGTATGACCCGACCGACGA<br>TATCGAAGCCTACGCGCTGAACGCCAGCCCCGATCGACCCCGCCCCCTCG<br>ATTTCCAAGAAATCGAATGACATCATCTTTCGAATGACATCATCTTTCGA<br>GGGGACTTTCCTCGAACTTCCTTCGAGGGGACTTTCCTCGAGGGGACTTT<br>CCTCGAGGAGGAAAAACTCGAGTAGAGTCTAGACTCTACATTTTGACACC<br>CCCA<br><br>SEQ ID NO: 36<br>S2-274<br>TCGAATGAGTCACATCGATCTCCGCCCCCTCTTCGAGGGGGCGGGGTCGA<br>GGAGGAAAAACTCGAATGAGTCACATCGACCCTTTGATCTTCGAGGGGAC<br>TTTCCGGGGTGGAGCAAGCGTGACAAGTCCACGTATGACCCGACCGACGA<br>TATCGAAGCCTACGCGCTGAACGCCAGCCCCGATCGACCCCGCCCCCTCG<br>ATTTCCAAGAAATCGAATGACATCATCTTTCGAATGACATCATCTTTCGA<br>GGGGACTTTCCTCGAACTTCCTTCGAGGGGACTTTCCTCGAGGGGACTTT<br>CCTCGAGGGGACTTTCCTCGAGGAGGAAAAACTCGAAAGATGATGTCATT<br>CGAGTTTTTCCTCCTCGAGGAGGAAAAACTCGAGTAGAGTCTAGACTCTA<br>CATTTTGACACCCCCA<br><br>SEQ ID NO: 37<br>S2-310<br>TCGAATGAGTCACATCGATCTCCGCCCCCTCTTCGAGGGGGCGGGGTCGA<br>GGAGGAAAAACTCGAATGAGTCACATCGACCCTTTGATCTTCGAGGGGAC<br>TTTCCGGGGTGGAGCAAGCGTGACAAGTCCACGTATGACCCGACCGACGA<br>TATCGAAGCCTACGCGCTGAACGCCAGCCCCGATCGACCCCGCCCCCTCG<br>ATTTCCAAGAAATCGAATGACATCATCTTTCGAATGACATCATCTTTCGA<br>GGGGACTTTCCTCGAACTTCCTTCGAGGGGACTTTCCTCGAGGGGACTTT<br>CCTCGAGGGGACTTTCCTCGAGGAGGAAAAACTCGAGTAGAGTCTAGACT<br>CTACATTTTGACACCCCCA<br><br>SEQ ID NO: 38<br>S1-367<br>TCGATTTCCAAGAAATCGACCCCGCCCCCTCGAACTTCCTTCGATTTCTT<br>GGAAATCGAGGAAAGTCCCCTCGATTTCTTGGAAATCGATTTCTTGGAAA<br>TCGAATGACATCATCTTTCGATTTCTTGGAAATCGACCCTTTGATCTTCG<br>AGGAGGAAAAACTCGAATGACATCATCTTTCGATCACGTCCTCGAAGATC<br>AAAGGGTCGAGTTTTTCCTCCTCGAGGAAAGTCCCCTCGATGTGACTCAT<br>TCGATTTCTTGGAAATCGAGGGGACTTTCCTCGAGGGGACTTTCCTCGAG<br>TTTTTCCTCCTCGAGGAGGAAAAACTCGATTTCCAAGAAATCGAGGGGAC<br>TTTCCTCGACCCTTTGATCTTCGAGCGCCAAATCGAGTAGAGTCTAGACT<br>CTACATTTTGACACCCCCA<br><br>SEQ ID NO: 39<br>S1-7<br>TCGATTTCTTGGAAATCGATTTGGCGCTCGAAGGAAGTTCGAGGGGGCGG<br>GGTCGATTTCCAAGAAATCGAGTTTTTCCTCCTCGAGCGCCAAATCGACC<br>CTTTGATCTTCGATCACGTCCTCGAGCGCCAAATCGAGGACGTGATCGAA<br>TGAGTCACATCGAATGAGTCACATCGAATGAGTCACATCGATTTGGCGCT<br>CGATCGGGGGCGGGGTCGAGGAAAGTCCCCTCGAGGAAAGTCCCCTCGA<br>TTTCCAAGAAATCGATTTGGCGCTCGATCTCCGCCCCCTCTTCGATCTCC<br>GCCCCCTCTTCGAGTTTTTCCTCCTCGAGTAGAGTCTAGACTCTACATTT<br>TGACACCCCCA |

SEQUENCE LISTING

<160> NUMBER OF SEQ ID NOS: 39

<210> SEQ ID NO 1
<211> LENGTH: 265
<212> TYPE: DNA
<213> ORGANISM: Artificial Sequence
<220> FEATURE:
<223> OTHER INFORMATION: Syn-iPro S1-17

<400> SEQUENCE: 1

```
ctgcttaggg ttaggcgttt tgcgctgctt cgcgatcgag gaggaaaaac tcgatgtgac      60
tcattcgaag atcaaagggt cgaggaaagt cccctcgacc ctttgatctt cgaatgacat     120
catctttcga ggaaagtccc ctcgagggga ctttcctcga ggggactttc ctcgaatgag     180
tcacatcgat ctccgccccc tcttcgagcg ccaaatcgag gacgtgatcg agtagagtct     240
agactctaca ttttgacacc cccat                                           265
```

<210> SEQ ID NO 2
<211> LENGTH: 232
<212> TYPE: DNA
<213> ORGANISM: Artificial Sequence
<220> FEATURE:
<223> OTHER INFORMATION: Syn-iPro S1-37

<400> SEQUENCE: 2

```
ctgcttaggg ttaggcgttt tgcgctgctt cgcgatcgag ggggcggggt cgatctccgc      60
cccctcttcg agttttcct cctcgagggg actttcctcg aatgacatca tctttcgacc     120
ctttgatctt cgaaggaagt tcgatcacgt cctcgatttg gcgctcgagg gactttcct     180 cgaagatcaa agggtcgagt agagtctaga ctctacattt tgacaccccc at            232
```

<210> SEQ ID NO 3
<211> LENGTH: 257
<212> TYPE: DNA
<213> ORGANISM: Artificial Sequence
<220> FEATURE:
<223> OTHER INFORMATION: Syn-iPro S1-4

<400> SEQUENCE: 3

```
ctgcttaggg ttaggcgttt tgcgctgctt cgcgatcgat ttccaagaaa tcgaggaaag      60 tccctcgac cctttgatct tcgaggagga aaaactcgaa tgagtcacat cgaccctttg     120
atcttcgaag aggggcgga gatcgatctc cgccccctct tcgaggaaag tcccctcgac     180
cctttgatct tcgaccccgc ccctcgagg aaagtcccct cgagtagagt ctagactcta     240
cattttgaca ccccat                                                     257
```

<210> SEQ ID NO 4
<211> LENGTH: 256
<212> TYPE: DNA
<213> ORGANISM: Artificial Sequence
<220> FEATURE:
<223> OTHER INFORMATION: Syn-iPro S1-1

<400> SEQUENCE: 4

```
ctgcttaggg ttaggcgttt tgcgctgctt cgcgatcgat ctccgccccc tcttcgaaga      60
tcaaagggtc gagggggactt tcctcgattt cttggaaatc gaatgacatc atctttcgat     120
ttggcgctcg aatgacatca tctttcgacc ctttgatctt cgatgtgact cattcgaggg     180
gactttcctc gaagatcaaa gggtcgaggg gactttcctc gagtagagtc tagactctac     240
attttgacac ccccat                                                     256
```

<210> SEQ ID NO 5
<211> LENGTH: 205
<212> TYPE: DNA
<213> ORGANISM: Artificial Sequence
<220> FEATURE:
<223> OTHER INFORMATION: Syn-iPro S1-3

<400> SEQUENCE: 5

```
ctgcttaggg ttaggcgttt tgcgctgctt cgcgatcgag gggactttcc tcgagggggc      60
ggggtcgatt tggcgctcga tctccgcccc ctcttcgaat gagtcacatc gaggaaagtc     120
ccctcgagga ggaaaaactc gatgtgactc attcgatttc aagaaatcg agtagagtct      180 agactctaca ttttgacacc cccat                                           205
```

<210> SEQ ID NO 6
<211> LENGTH: 283
<212> TYPE: DNA
<213> ORGANISM: Artificial Sequence
<220> FEATURE:
<223> OTHER INFORMATION: Syn-iPro S1-42

<400> SEQUENCE: 6

```
ctgcttaggg ttaggcgttt tgcgctgctt cgcgatcgat ttccaagaaa tcgatctccg      60
ccccctcttc gaatgacatc atctttcgaa tgcatcatc tttcgaggag gaaaaactcg     120
accccgcccc ctcgatttct ggaaatcga ggaaagtccc ctcgagcgcc aaatcgaagg     180
aagttcgaat gacatcatct ttcgaatgag tcacatcgag gaaagtcccc tcgaggagga    240
aaaactcgag tagagtctag actctacatt ttgacacccc cat                       283
```

<210> SEQ ID NO 7
<211> LENGTH: 390
<212> TYPE: DNA
<213> ORGANISM: Artificial Sequence
<220> FEATURE:
<223> OTHER INFORMATION: Syn-iPro S1-61

<400> SEQUENCE: 7

```
ctgcttaggg ttaggcgttt tgcgctgctt cgcgatcgaa tgagtcacat cgatctccgc      60 ccctcttcg aggggcggg gtcgaggagg aaaaactcga atgagtcaca tcgaccctt       120 gatcttcgag gggactttcc ggggtggagc aagcgtgaca agtccacgta tgaccccgacc    180 gacgatatcg aagcctacgc gctgaacgcc agccccgatc gaccccgccc ctcgatttc     240 caagaaatcg aatgacatca tctttcgaat gacatcatct ttcgagggga ctttcctcga    300
acttccttcg aggggacttt cctcgagggg actttcctcg aggaggaaaa actcgagtag    360
agtctagact ctacattttg acaccccccat                                      390
```

<210> SEQ ID NO 8
<211> LENGTH: 192
<212> TYPE: DNA
<213> ORGANISM: Artificial Sequence
<220> FEATURE:
<223> OTHER INFORMATION: Syn-iPro S1-62

<400> SEQUENCE: 8

```
ctgcttaggg ttaggcgttt tgcgctgctt cgcgatcgat ttccaagaaa tcgagttttt      60
cctcctcgag ggggcgggt cgaggggact ttcctcgacc ctttgatctt cgaggaaagt     120 ccccctcgagc gccaaatcga tctccgcccc ctcttcgagt agagtctaga ctctacattt    180
```

```
tgacaccccc at                                                         192

<210> SEQ ID NO 9
<211> LENGTH: 283
<212> TYPE: DNA
<213> ORGANISM: Artificial Sequence
<220> FEATURE:
<223> OTHER INFORMATION: Syn-iPro S1-15

<400> SEQUENCE: 9
ctgcttaggg ttaggcgttt tgcgctgctt cgcgatcgaa gatcaaaggg tcgatttctt     60
ggaaatcgat gtgactcatt cgatcacgtc ctcgaggagg aaaaactcga ggaaagtccc    120
ctcgaacttc cttcgagggg cggggtcga atgagtcaca tcgaggaaag tcccctcgag    180
gggactttcc tcgatttctt ggaaatcgaa gaggggcgg agatcgagtt tttcctcctc    240
gaggaaagtc ccctcgatcg actctacatt ttgacacccc cat                     283

<210> SEQ ID NO 10
<211> LENGTH: 274
<212> TYPE: DNA
<213> ORGANISM: Artificial Sequence
<220> FEATURE:
<223> OTHER INFORMATION: Syn-iPro S1-2

<400> SEQUENCE: 10
ctgcttaggg ttaggcgttt tgcgctgctt cgcgatcgaa tgagtcacat cgaagatcaa     60
agggtcgacc ctttgatctt cgatttggcg ctcgatgtga ctcattcgac cccgcccct    120 cgaggaaagt cccctcgagg aaagtcccct cgaggaaagt cccctcgagg aaagtcccct    180 cgagttttc ctcctcgaag aggggcgga gatcgatttg gcgctcgagg acgtgatcga    240
gtagagtcta gactctacat tttgacaccc ccat                              274

<210> SEQ ID NO 11
<211> LENGTH: 286
<212> TYPE: DNA
<213> ORGANISM: Artificial Sequence
<220> FEATURE:
<223> OTHER INFORMATION: Syn-iPro S1-27

<400> SEQUENCE: 11
ctgcttaggg ttaggcgttt tgcgctgctt cgcgatcgat ttccaagaaa tcgagttttt     60
cctcctcgat ttccaagaaa tcgaggggac tttcctcgag gggactttcc tcgaatgaca    120
tcatctttcg atgtgactca ttcgaagatc aaagggtcga aggaagttcg aatgagtcac    180
atcgaatgag tcacatcgac ccttgatctt cgaggaggaa aaactcgatt ggcgctcga    240 tttggcgctc gagtagagtc tagactctac attttgacac ccccat                 286

<210> SEQ ID NO 12
<211> LENGTH: 397
<212> TYPE: DNA
<213> ORGANISM: Artificial Sequence
<220> FEATURE:
<223> OTHER INFORMATION: Syn-iPro S1-8

<400> SEQUENCE: 12
ctgcttaggg ttaggcgttt tgcgctgctt cgcgatcgat ttcttggaaa tcgatttggc     60
gctcgaagga agttcgaggg ggcggggtcg atttccaaga atcgagtttt ttcctcctcg    120
agcgccaaat cgaccctttg atcttcgatc acgtcctcga gcgccaaatc gaggacgtga    180
tcgaatgagt cacatcgaat gagtcacatc gaatgagtca catcgatttg gcgctcgatc    240
```

```
ggggggcggg gtcgaggaaa gtcccctcga ggaaagtccc ctcgatttcc aagaaatcga      300
tttggcgctc gatctccgcc ccctcttcga tctccgcccc ctcttcgagt tttttcctcct    360 cgagtagagt ctagactcta cattttgaca ccccat                               397
```

<210> SEQ ID NO 13
<211> LENGTH: 235
<212> TYPE: DNA
<213> ORGANISM: Artificial Sequence
<220> FEATURE:
<223> OTHER INFORMATION: Syn-iPro S1-30

<400> SEQUENCE: 13

```
ctgcttaggg ttaggcgttt tgcgctgctt cgcgatcgaa tgacatcatc tttcgaggaa      60
agtcccctcg acccttttgat cttcgacccc gccccctcga gttttttcctc ctcgaggaaa   120 gtccccctcga cccttttgatc ttcgagggga cttttcctcga ggggcgggg tcgaggacgt   180 gatcgaggaa agtcccctcg agtagagtct agactctaca ttttgacacc cccat          235
```

<210> SEQ ID NO 14
<211> LENGTH: 335
<212> TYPE: DNA
<213> ORGANISM: Artificial Sequence
<220> FEATURE:
<223> OTHER INFORMATION: Syn-iPro S1-33

<400> SEQUENCE: 14

```
ctgcttaggg ttaggcgttt tgcgctgctt cgcgatcgaa gatcaaaggg tcgaggagga      60
aaaactcgag gggactttcc tcgacccttt gatcttcgaa tgagtcacat cgatttcttg    120
gaaatcgaag gaagttcgag gggactttcc tcgagttttt cctcctcgaa cttccttcga    180
ggaaagtccc ctcgaagatc aaagggtcga aggaagttcg aaagatgatg tcattcgatt    240
tcttggaaat cgaagatcaa agggtcgaag aggggcgga gatcgatttc caagaaatcg     300
agtagagtct agactctaca ttttgacacc cccat                                335
```

<210> SEQ ID NO 15
<211> LENGTH: 203
<212> TYPE: DNA
<213> ORGANISM: Artificial Sequence
<220> FEATURE:
<223> OTHER INFORMATION: Syn-iPro S1-41

<400> SEQUENCE: 15

```
ctgcttaggg ttaggcgttt tgcgctgctt cgcgatcgaa tgagtcacat cgagcgccaa      60
atcgagggga ctttcctcga gggggcgggg tcgagttttt cctcctcgat ttccaagaaa    120 tcgagggggac tttcctcgag gggactttcc tcgagggggac tttcctcgag tagagtctag   180
actctacatt ttgacacccc cat                                             203
```

<210> SEQ ID NO 16
<211> LENGTH: 287
<212> TYPE: DNA
<213> ORGANISM: Artificial Sequence
<220> FEATURE:
<223> OTHER INFORMATION: Syn-iPro S1-59

<400> SEQUENCE: 16

```
ctgcttaggg ttaggcgttt tgcgctgctt cgcgatcgag ttttttcctcc tcgaggggac    60 tttcctcgaa agatgatgtc attcgatctc cgcccctct tcgaggggac tttcctcgag     120
```

| | |
|---|---|
| gaaagtcccc tcgaggaaag tccctcgaa gatcaaaggg tcgaatgagt cacatcgacc | 180 |
| ctttgatctt cgaccctttg atcttcgatt ccaagaaat cgaggaaagt ccctcgagg | 240 |
| aaagtcccct cgagtagagt ctagactcta cattttgaca cccccat | 287 |

<210> SEQ ID NO 17
<211> LENGTH: 293
<212> TYPE: DNA
<213> ORGANISM: Artificial Sequence
<220> FEATURE:
<223> OTHER INFORMATION: Syn-iPro S1-66

<400> SEQUENCE: 17

| | |
|---|---|
| ctgcttaggg ttaggcgttt tgcgctgctt cgcgatcgag gggactttcc tcgaggaaag | 60 |
| tccctcgat tcttggaaa tcgatttggc gctcgaggag gaaaactcg atgtgactca | 120 |
| ttcgacccctt tgatcttcga ggggactttc ctcgagggga cttttcctcga gcgccaaatc | 180 |
| gaggaggaaa aactcgaggg gactttcctc gatttcttgg aaatcgaaag atgatgtcat | 240 |
| tcgacccttt gatcttcgag tagagtctag actctacatt tgacacccc cat | 293 |

<210> SEQ ID NO 18
<211> LENGTH: 252
<212> TYPE: DNA
<213> ORGANISM: Artificial Sequence
<220> FEATURE:
<223> OTHER INFORMATION: Syn-iPro S1-71

<400> SEQUENCE: 18

| | |
|---|---|
| ctgcttaggg ttaggcgttt tgcgctgctt cgcgatcgag gaaagtcccc tcgaggaaag | 60 |
| tccctcgat tcttggaaa tcgaatgaca tcatctttcg atcacgtcct cgaggaaagt | 120 |
| ccctcgagt ttttcctcct cgaggggact tcctcgatt tccaagaaat cgattcttg | 180 |
| gaaatcgacc ctttgatctt cgaggaggaa aactcgagt agagtctaga ctctacattt | 240 |
| tgacaccccc at | 252 |

<210> SEQ ID NO 19
<211> LENGTH: 215
<212> TYPE: DNA
<213> ORGANISM: Artificial Sequence
<220> FEATURE:
<223> OTHER INFORMATION: Syn-iPro S1-56

<400> SEQUENCE: 19

| | |
|---|---|
| ctgcttaggg ttaggcgttt tgcgctgctt cgcgatcgat gtgactcatt cgaggaaagt | 60 |
| ccctcgatt tggcgctcga tgtgactcat tcgatttggc gctcgagggg actttcctcg | 120 |
| atttccaaga atcgaggggg actttcctcg aggaaagtcc cctcgagttt tcctcctcg | 180 |
| agtagagtct agactctaca ttttgacacc cccat | 215 |

<210> SEQ ID NO 20
<211> LENGTH: 254
<212> TYPE: DNA
<213> ORGANISM: Artificial Sequence
<220> FEATURE:
<223> OTHER INFORMATION: Syn-iPro S1-6

<400> SEQUENCE: 20

| | |
|---|---|
| ctgcttaggg ttaggcgttt tgcgctgctt cgcgatcgat gtgactcatt cgagcgccaa | 60 |
| atcgatttcc aagaaatcga atgagtcaca tcgaatgaca tcatctttcg atgtgactca | 120 |
| ttcgaggaaa gtcccctcga tttcttggaa atcgaggaaa gtcccctcga gttttcctc | 180 |

```
ctcgaagagg gggcggagat cgaatgacat catctttcga gtagagtcta gactctacat    240
tttgacaccc ccat                                                      254

<210> SEQ ID NO 21
<211> LENGTH: 355
<212> TYPE: DNA
<213> ORGANISM: Artificial Sequence
<220> FEATURE:
<223> OTHER INFORMATION: Syn-iPro S1-60

<400> SEQUENCE: 21
ctgcttaggg ttaggcgttt tgcgctgctt cgcgatcgag gggactttcc tcgatctccg     60 cccctcttc gaggaaagtc ccctcgaagg aagttcgaac ttccttcgag gggactttcc    120
tcgaaggaag ttcgagcgcc aaatcgaatg agtcacatcg atttccaaga aatcgatctc    180
cgccccctct tcgaggagga aaaactcgag gggactttcc tcgatttcca agaaatcgag    240
gggactttcc tcgatcacgt cctcgaggac gtgatcgaat gagtcacatc gatgtgactc    300
attcgaccct tgatcttcg agtagagtct agactctaca ttttgacacc cccat          355

<210> SEQ ID NO 22
<211> LENGTH: 302
<212> TYPE: DNA
<213> ORGANISM: Artificial Sequence
<220> FEATURE:
<223> OTHER INFORMATION: Syn-iPro S1-86

<400> SEQUENCE: 22
ctgcttaggg ttaggcgttt tgcgctgctt cgcgatcgat ttccaagaaa tcgaggggc      60 ggggtcgagg ggactttcct cgaggggact ttcctcgagg aaagtcccct cgatctccgc    120 ccctcttcg aggaaagtcc cctcgaactt ccttcgagga aagtcccctc gaatgagtca    180
catcgatttg gcgctcgagg aaagtcccct cgaggggact ttcctcgagg aaagtcccct    240 cgaggggcg gggtcgaact tccttcgagt agagtctaga ctctacattt tgacaccccc    300
at                                                                   302

<210> SEQ ID NO 23
<211> LENGTH: 192
<212> TYPE: DNA
<213> ORGANISM: Artificial Sequence
<220> FEATURE:
<223> OTHER INFORMATION: Syn-iPro S1-32

<400> SEQUENCE: 23
ctgcttaggg ttaggcgttt tgcgctgctt cgcgatcgaa tgagtcacat cgatctccgc     60 ccctcttcg atttggcgct cgaggggact ttcctcgacc ctttgatctt cgagggact     120 ttcctcgagg aaagtcccct cgaggaaagt ccctcgagt agagtctaga ctctacattt    180 tgacacccc at                                                         192

<210> SEQ ID NO 24
<211> LENGTH: 248
<212> TYPE: DNA
<213> ORGANISM: Artificial Sequence
<220> FEATURE:
<223> OTHER INFORMATION: Syn-iPro S1-10

<400> SEQUENCE: 24
ctgcttaggg ttaggcgttt tgcgctgctt cgcgatcgat ttggcgctcg atgtgactca     60
```

```
ttcgaggaaa gtcccctcga ggggactttc ctcgaagatc aaagggtcga agatgatgt    120 cattcgagga agtcccctc gaccccgccc cctcgatttc ttggaaatcg aatgagtcac    180
atcgatttct tggaaatcga gtgactcat tcgagtagag tctagactct acattttgac    240
accccat                                                             248

<210> SEQ ID NO 25
<211> LENGTH: 342
<212> TYPE: DNA
<213> ORGANISM: Artificial Sequence
<220> FEATURE:
<223> OTHER INFORMATION: Syn-iPro S1-18

<400> SEQUENCE: 25
ctgcttaggg ttaggcgttt tgcgctgctt cgcgatcgag gggactttcc tcgatgtgac     60
tcattcgatt tcttggaaat cgatttccaa gaaatcgacc ccgcccctc gaggaggaaa    120 aactcgattt ccaagaaatc gaatgacatc atctttcgag gggactttcc tcgaagatca    180
aagggtcgaa gatcaaaggg tcgaggagga aaaactcgat ttccaagaaa tcgaatgagt    240
cacatcgagt ttttcctcct cgatttcttg gaaatcgaag ggggcgga atcgatttg      300 gcgctcgagt agagtctaga ctctacattt tgacacccccc at                    342

<210> SEQ ID NO 26
<211> LENGTH: 268
<212> TYPE: DNA
<213> ORGANISM: Artificial Sequence
<220> FEATURE:
<223> OTHER INFORMATION: Syn-iPro S1-14

<400> SEQUENCE: 26
ctgcttaggg ttaggcgttt tgcgctgctt cgcgatcgaa agatgatgtc attcgaatga     60
gtcacatcga tttggcgctc gagggggcgg ggtcgatttg gcgctcgaaa gatgatgtca    120
ttcgagtttt tcctcctcga ccctttgatc ttcgaagagg gggcggagat cgaaagatga    180
tgtcattcga atgagtcaca tcgatttcca agaaatcgat ttccaagaaa tcgagtagag    240
tctagactct acattttgac accccat                                       268

<210> SEQ ID NO 27
<211> LENGTH: 272
<212> TYPE: DNA
<213> ORGANISM: Artificial Sequence
<220> FEATURE:
<223> OTHER INFORMATION: Syn-iPro S1-16

<400> SEQUENCE: 27
ctgcttaggg ttaggcgttt tgcgctgctt cgcgatcgag gaggaaaaac tcgatttctt     60
ggaaatcgag gggactttcc tcgaaagatg atgtcattcg aagatcaaag ggtcgatgtg    120
actcattcga ggggactttc ctcgaggggg cggggtcgaa tgacatcatc tttcgagggg    180
actttcctcg aggggacttt cctcgaatga catcatcttt cgatttcttg gaaatcgagt    240
agagtctaga ctctacattt tgacacccccc at                                272

<210> SEQ ID NO 28
<211> LENGTH: 223
<212> TYPE: DNA
<213> ORGANISM: Artificial Sequence
<220> FEATURE:
<223> OTHER INFORMATION: Syn-iPro S1-19

<400> SEQUENCE: 28
```

```
ctgcttaggg ttaggcgttt tgcgctgctt cgcgatcgat ctccgccccc tcttcgagtt      60
tttcctcctc gatttcttgg aaatcgaaga tcaaagggtc gatttcttgg aaatcgaggg     120
gactttcctc gaggaaagtc ccctcgaggg gactttcctc gaggaggaaa aactcgattt     180
ggcgctcgag tagagtctag actctacatt ttgacacccc cat                       223
```

<210> SEQ ID NO 29
<211> LENGTH: 216
<212> TYPE: DNA
<213> ORGANISM: Artificial Sequence
<220> FEATURE:
<223> OTHER INFORMATION: Syn-iPro S1-26

<400> SEQUENCE: 29

```
ctgcttaggg ttaggcgttt tgcgctgctt cgcgatcgaa agatgatgtc attcgagttt      60
ttcctcctcg aaggaagttc gaggacgtga tcgaagaggg ggcggagatc gaatgagtca     120
catcgaagga agttcgagga aagtcccctc gaggaaagtc ccctcgaaga tcaaagggtc     180
gagtagagtc tagactctac attttgacac ccccat                               216
```

<210> SEQ ID NO 30
<211> LENGTH: 144
<212> TYPE: DNA
<213> ORGANISM: Artificial Sequence
<220> FEATURE:
<223> OTHER INFORMATION: Syn-iPro S1-65

<400> SEQUENCE: 30

```
ctgcttaggg ttaggcgttt tgcgctgctt cgcgatcgac cccgcccct cgagcgccaa       60 atcgagggga cttttcctcga ggggactttc ctcgagggga cttttcctcga gtagagtcta   120 gactctacat tttgacaccc ccat                                            144
```

<210> SEQ ID NO 31
<211> LENGTH: 235
<212> TYPE: DNA
<213> ORGANISM: Artificial Sequence
<220> FEATURE:
<223> OTHER INFORMATION: Syn-iPro S2-n1

<400> SEQUENCE: 31

```
ctgcttaggg ttaggcgttt tgcgctgctt cgcgatcgag ggggcggggt cgaatgacat      60
catctttcga ggaaagtccc ctcgaggaaa gtcccctcga ggaaagtccc ctcgatttcc     120
aagaaatcga ccctttgatc ttcgaagatc aaagggtcga tgtgactcat tcgaagatca     180
aagggtcgat tggcgctcg agtagagtct agactctaca ttttgacacc cccat           235
```

<210> SEQ ID NO 32
<211> LENGTH: 295
<212> TYPE: DNA
<213> ORGANISM: Artificial Sequence
<220> FEATURE:
<223> OTHER INFORMATION: Syn-iPro S4-n1

<400> SEQUENCE: 32

```
ctgcttaggg ttaggcgttt tgcgctgctt cgcgatcgag gaaagtcccc tcgagttttt      60
cctcctcgaa gaggggggcgg agatcgattt ccaaaaaact cgaatgacat catctttcga    120
agatcaaggg gtcgaagatc aaagggtcga tttccaagaa atcgatttct ggaaatcga     180 ggaaagtccc ctcgaccctt tgatcttcga tctccgcccc tcttcgaag atcaaagggt     240
```
cgaagagggg gcggagatcg agtagagtct agactctaca ttttgacacc cccat      295

<210> SEQ ID NO 33
<211> LENGTH: 308
<212> TYPE: DNA
<213> ORGANISM: Artificial Sequence
<220> FEATURE:
<223> OTHER INFORMATION: Syn-iPro S6-n1

<400> SEQUENCE: 33
ctgcttaggg ttaggcgttt tgcgctgctt cgcgatcgat ttccaagaaa tcgatttctt      60
ggaaatcgaa tgacatcatc tttcgagttt ttcctcctcg aagaggggc ggagatcgag     120
gaaagtcccc tcgatttcca agaaatcgaa cttccttcga aggaagttcg aggaggaaaa     180
actcgagggg gcgggtcga gttttcctc ctcgagggga cttcctcga ccccgcccc     240
tcgacccttt gatcttcgat ttccaagaaa tcgagtagag tctagactct acattttgac     300
accccccat                                                            308

<210> SEQ ID NO 34
<211> LENGTH: 435
<212> TYPE: DNA
<213> ORGANISM: Artificial Sequence
<220> FEATURE:
<223> OTHER INFORMATION: Syn-iPro S1-325

<400> SEQUENCE: 34
tcgaagatca aagggtcgat ttccaagaaa tcgatgtgac tcattcgatt tggcgctcga      60
ccccgcccc tcgaagaggg gcggagatc gaatgagtca catcgaggaa agtcccctcg     120
atttcttgga aatcgaggaa agtcccctcg agggactttt cctcgaggag gaaaaactcg     180
aatgacatca tctttcgaat gagtcacatc gatttcttgg aaatcgaggg acttttcctc     240
gaccccgccc cctcgaggtg acttcctcg aggggactttt cctcgatgtg actcattcga     300
ggggactttc ctcgagggga ctttcctcga ccctttgatc ttcgatttgg cgctcgaggg     360
gactttcctc gagggggactt ttcctcgaggg gactttcctc gagtagagtc tagactctac     420
attttgacac cccca                                                      435

<210> SEQ ID NO 35
<211> LENGTH: 354
<212> TYPE: DNA
<213> ORGANISM: Artificial Sequence
<220> FEATURE:
<223> OTHER INFORMATION: Syn-iPro S1-60

<400> SEQUENCE: 35
tcgaatgagt cacatcgatc tccgccccct cttcgagggg gcgggtcga ggaggaaaaa      60
ctcgaatgag tcacatcgac cctttgatct tcgaggggac tttccggggt ggagcaagcg     120
tgacaagtcc acgtatgacc cgaccgacga tatcgaagcc tacgcgctga acgcagcccc     180
cgatcgaccc cgcccctcg atttccaaga aatcgaatga catcatcttt cgaatgacat     240
catctttcga ggggactttc ctcgaacttc cttcgagggg actttcctcg aggggactttt     300
cctcgaggag gaaaaactcg agtagagtct agactctaca ttttgacacc ccca           354

<210> SEQ ID NO 36
<211> LENGTH: 416
<212> TYPE: DNA
<213> ORGANISM: Artificial Sequence
<220> FEATURE:
<223> OTHER INFORMATION: Syn-iPro S2-274

<400> SEQUENCE: 36

```
tcgaatgagt cacatcgatc tccgccccct cttcgagggg gcggggtcga ggaggaaaaa      60
ctcgaatgag tcacatcgac cctttgatct tcgaggggac tttccggggt ggagcaagcg     120
tgacaagtcc acgtatgacc cgaccgacga tatcgaagcc tacgcgctga acgccagccc     180
cgatcgaccc cgcccctcg atttccaaga aatcgaatga catcatcttt cgaatgacat      240
catctttcga ggggactttc ctcgaacttc cttcgagggg actttcctcg agggggacttt    300
cctcgagggg actttcctcg aggaggaaaa actcgaaaga tgatgtcatt cgagttttc     360
ctcctcgagg aggaaaaact cgagtagagt ctagactcta catttgaca cccca          416
```

<210> SEQ ID NO 37
<211> LENGTH: 369
<212> TYPE: DNA
<213> ORGANISM: Artificial Sequence
<220> FEATURE:
<223> OTHER INFORMATION: Syn-iPro S2-310

<400> SEQUENCE: 37

```
tcgaatgagt cacatcgatc tccgccccct cttcgagggg gcggggtcga ggaggaaaaa      60
ctcgaatgag tcacatcgac cctttgatct tcgaggggac tttccggggt ggagcaagcg     120
tgacaagtcc acgtatgacc cgaccgacga tatcgaagcc tacgcgctga acgccagccc     180
cgatcgaccc cgcccctcg atttccaaga aatcgaatga catcatcttt cgaatgacat      240
catctttcga ggggactttc ctcgaacttc cttcgagggg actttcctcg agggggacttt    300
cctcgagggg actttcctcg aggaggaaaa actcgagtag agtctagact ctacattttg    360
acacccca                                                              369
```

<210> SEQ ID NO 38
<211> LENGTH: 419
<212> TYPE: DNA
<213> ORGANISM: Artificial Sequence
<220> FEATURE:
<223> OTHER INFORMATION: Syn-iPro S1-367

<400> SEQUENCE: 38

```
tcgatttcca agaaatcgac cccgccccct cgaacttcct tcgatttctt ggaaatcgag      60
gaaagtcccc tcgatttctt ggaaatcgat ttcttggaaa tcgaatgaca tcatctttcg     120
atttcttgga aatcgaccct tgatcttcg aggaggaaaa actcgaatga catcatcttt      180
cgatcacgtc ctcgaagatc aaagggtcga gttttcctc ctcgaggaaa gtcccctcga      240
tgtgactcat tcgatttctt ggaaatcgag gggactttcc tcgagggac tttcctcgag     300
ttttcctcc tcgaggagga aaaactcgat tccaagaaa tcgaggggac tttcctcgac      360
cctttgatct tcgagcgcca aatcgagtag agtctagact ctacattttg acacccca     419
```

<210> SEQ ID NO 39
<211> LENGTH: 361
<212> TYPE: DNA
<213> ORGANISM: Artificial Sequence
<220> FEATURE:
<223> OTHER INFORMATION: Syn-iPro S1-7

<400> SEQUENCE: 39

```
tcgatttctt ggaaatcgat ttggcgctcg aaggaagttc gaggggggcgg ggtcgatttc     60
caagaaatcg agttttttcct cctcgagcgc caaatcgacc ctttgatctt cgatcacgtc   120
```

| | | | | | | |
|---|---|---|---|---|---|---|
| ctcgagcgcc | aaatcgagga | cgtgatcgaa | tgagtcacat | cgaatgagtc | acatcgaatg | 180 |
| agtcacatcg | atttggcgct | cgatcggggg | gcggggtcga | ggaaagtccc | ctcgaggaaa | 240 |
| gtccctcga | tttccaagaa | atcgatttgg | cgctcgatct | ccgcccctc | ttcgatctcc | 300 |
| gcccctctt | cgagttttc | ctcctcgagt | agagtctaga | ctctacattt | tgacaccccc | 360 |
| a | | | | | | 361 |

What is claimed is:

1. An isolated nucleic acid comprising a promoter comprising a transcription response element having a sequence with at least 98% sequence identity to the sequence as set forth in SEQ ID NO: 7.

2. The isolated nucleic acid of claim 1, wherein the transcription response element comprises a sequence having at least 99% sequence identity to the sequence as set forth in SEQ ID NO: 7.

3. The isolated nucleic acid of claim 1, wherein the transcription response element comprises the sequence as set forth in SEQ ID NO: 7.

4. The isolated nucleic acid of claim 1, wherein the promoter further comprises an IL2 minimal promoter.

5. The isolated nucleic acid of claim 1, wherein the isolated nucleic acid is operably linked to a sequence encoding a payload.

6. The isolated nucleic acid of claim 5, wherein the payload comprises CD122, CD127, CD360, caSTAT5, dnSHP1, or dnSHP2; PD1:MyD88, PD1:CD28, CD200:CD28, or miRNA155.

7. A vector comprising a nucleic acid comprising a promoter comprising a transcription response element having a sequence with at least 98% sequence identity to the sequence as set forth in SEQ ID NO: 7, wherein the nucleic acid is operably linked to a sequence encoding a payload.

8. The vector of claim 7, wherein the transcription response element comprises a sequence having at least 99% sequence identity to the sequence as set forth in SEQ ID NO: 7.

9. The vector of claim 7, wherein the transcription response element comprises the sequence as set forth in SEQ ID NO: 7.

10. The vector of claim 7, wherein the promoter further comprises a minimal IL2 promoter.

11. The vector of claim 7, wherein the vector comprises a viral vector, a transposase based minicircle, or a nanoplasmid.

12. The vector of claim 7, wherein the vector comprises a lentiviral vector.

13. The vector of claim 7, wherein the payload comprises CD122, CD127, CD360, caSTAT5, dnSHP1, or dnSHP2; PD1:MyD88, PD1:CD28, CD200:CD28, or miRNA155.

14. A cell comprising: the vector of claim 7.

15. The cell of claim 14, wherein the transcription response element comprises a sequence having at least 99% sequence identity to the sequence as set forth in SEQ ID NO: 7.

16. The cell of claim 14, wherein the transcription response element comprises the sequence as set forth in SEQ ID NO: 7.

17. The cell of claim 14, wherein the promoter further comprises a minimal IL2 promoter.

18. The cell of claim 14, wherein the cell is a T cell or a hematopoietic stem cell.

19. The cell of claim 18, wherein the T cell is a CD4+ T cell or a CD8+ T cell.

20. The cell of claim 14, wherein the cell further comprises a nucleic acid encoding a chimeric antigen receptor (CAR).

* * * * *

UNITED STATES PATENT AND TRADEMARK OFFICE
CERTIFICATE OF CORRECTION

| | | |
|---|---|---|
| PATENT NO. | : 11,851,649 B2 | Page 1 of 1 |
| APPLICATION NO. | : 16/613025 | |
| DATED | : December 26, 2023 | |
| INVENTOR(S) | : Jia Wei et al. | |

It is certified that error appears in the above-identified patent and that said Letters Patent is hereby corrected as shown below:

On the Title Page

Item (71), please change "Seattle Children's Hospital" to "Seattle Children's Hospital d/b/a Seattle Children's Research Institute".

Item (73), please change "Seattle Children's Hospital" to "Seattle Children's Hospital d/b/a Seattle Children's Research Institute".

Signed and Sealed this
Twenty-first Day of October, 2025

John A. Squires
*Director of the United States Patent and Trademark Office*